United States Patent [19]

Sugihara et al.

[11] Patent Number: 4,638,000
[45] Date of Patent: Jan. 20, 1987

[54] CONDENSED SEVEN-MEMBERED RING COMPOUNDS, THEIR PRODUCTION AND USE

[75] Inventors: Hirosada Sugihara, Osaka; Kohei Nishikawa, Kyoto; Katsumi Ito, Osaka, all of Japan

[73] Assignee: Takeda Chemical Industries, Ltd., Osaka, Japan

[21] Appl. No.: 691,005

[22] Filed: Jan. 14, 1985

Related U.S. Application Data

[63] Continuation-in-part of Ser. No. 637,620, Aug. 3, 1984, Pat. No. 4,548,932.

[30] Foreign Application Priority Data

Mar. 22, 1984 [WO] PCT Int'l Appl. .... PCT/JP84/00119
Apr. 6, 1984 [WO] PCT Int'l Appl. .... PCT/JP84/00172
Jul. 13, 1984 [WO] PCT Int'l Appl. .... PCT/JP84/00363

[51] Int. Cl.$^4$ ............... A61K 31/55; C07D 417/12
[52] U.S. Cl. ............................ 514/211; 546/227; 546/245; 560/51; 560/53; 560/174; 560/177; 560/226; 560/150; 560/10; 540/491
[58] Field of Search ................ 260/239.3 B; 514/211

[56] References Cited

U.S. PATENT DOCUMENTS 3,341,519 9/1967 Krapcho .................. 260/239.3 B
4,460,579 7/1984 Karanewsky ............ 260/239.3 B
4,477,464 10/1984 Slade et al. ............... 260/239.3 B
4,539,150 9/1985 Katakami et al. ........ 260/239.3 B

FOREIGN PATENT DOCUMENTS 51391 5/1982 European Pat. Off. ............. 560/28
57998 8/1982 European Pat. Off. ...... 260/239.3 B
68173 1/1983 European Pat. Off. ...... 260/239.3 B
58-29779 2/1983 Japan ............................ 260/239.3 B
2103614 2/1983 United Kingdom ......... 260/239.3 B

OTHER PUBLICATIONS

Chemical Abstracts vol. 94, p. 657 (1981), Registry No. 94: 156884t.
Central Patents Index, Basic Abstracts Journal, Section B: FARMDOC, 01015 E/01 B02 TANA 02.05.80 J56156-218 (Mar. 3, 1982).
Central Patents Index, Basic Abstracts Journal, Section B: FARMDOC, 82663 E/39 B02 NIPK 18.02.81 J57136-581 (Nov. 24, 1982).
Central Patents Index, Basic Abstracts Journal, Section B: FARMDOC, 01471 J/47 B02 HAMA 3.04.81 J57169-474 (Jan. 26, 1983).

Primary Examiner—Robert T. Bond
Attorney, Agent, or Firm—Wegner & Bretschneider

[57] ABSTRACT

Novel condensed seven-membered ring compounds of the formula:

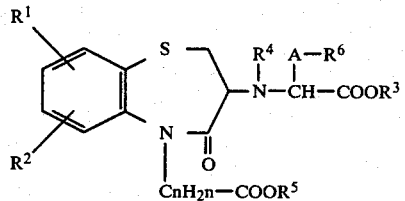

[wherein $R^1$ and $R^2$ are independently hydrogen, halogen, trifluoromethyl, lower alkyl or lower alkoxy, or both jointly form tri- or tetramethylene; $R^3$ and $R^5$ are independently hydrogen, lower alkyl or aralkyl; $R^4$ is hydrogen or lower alkyl; $R^6$ is a condensed or non-condensed hetero-alicyclic containing at least one atom of N, O and S as a ring-forming atom which may be substituted; A is an alkylene chain; n is 1 or 2] and salts thereof.

These compounds exhibit inhibitory activity on angiotensin converting enzyme and so forth, and are of value as an agent for diagnosis, prevention and treatment of circulatory diseases, such as hypertension, cardiopathy and cerebral apoploxy.

27 Claims, No Drawings

CONDENSED SEVEN-MEMBERED RING COMPOUNDS, THEIR PRODUCTION AND USE

This application is a continuation-in-part of application Ser. No. 637,620, filed Aug. 3, 1984, and now U.S. Pat. No. 4,548,932.

TECHNICAL FIELD

This invention relates to novel condensed seven-membered ring compounds useful as pharmaceuticals, and to a process for producing the same.

BACKGROUND ART

A variety of compounds having angiotensin converting enzyme inhibitory activities are known, but compounds having further condensed seven membered ring as a basic moiety are disclosed only in European Patent Publication of Application No. 72352.

The present inventors, after extensive search for compounds which exhibit inhibitory activity on angiotensin converting enzyme and are useful as a therapeutic agent for circulatory diseases such as hypertension, cardiopathy and cerebral apoplexy, succeeded in the production of condensed seven-membered ring compounds having excellent action, and have completed the present invention.

DISCLOSURE OF THE INVENTION

The present invention provides compounds represented by the formula:

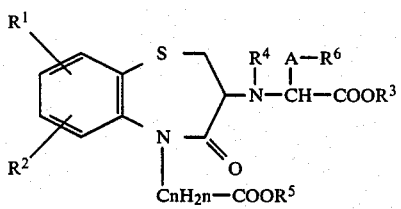

[wherein $R^1$ and $R^2$ are independently hydrogen, halogen, trifluoromethyl, lower alkyl or lower alkoxy, or both jointly form tri- or tetramethylene; $R^3$ and $R^5$ are independently hydrogen, lower alkyl, or aralkyl; $R^4$ is hydrogen or lower alkyl; $R^6$ is a condensed or non-condensed hetero-alicyclic group containing at least one atom of N, O and S as a ring-forming atom which may be sustituted; A is an alkylene chain; n is 1 or 2] and salts thereof, and a process for producing the same.

Referring to the above formula (I), the halogen represented by $R^1$ or $R^2$ includes, for example, fluorine, chlorine, bromine and iodine, and the lower alkoxy group represented by $R^1$ or $R^2$ includes alkoxy groups containing about 1 to 4 carbon atoms, such as methoxy, ethoxy, propoxy, isopropoxy, butoxy, isobutoxy, sec-butoxy and tert-butoxy. Also, $R^1$ and $R^2$ both may combine with each other to form an alkylene bridge, whose examples include those such as trimethylene and tetramethylene.

The lower alkyl group represented by $R^1$, $R^2$, $R^3$, $R^4$ or $R^5$ includes alkyl groups containing about 1 to 4 carbon atoms, such as methyl, ethyl, propyl, isopropyl, butyl, isobutyl, sec-butyl and tert-butyl.

The aralkyl group represented by $R^3$ or $R^5$ includes phenyl-lower-($C_{1-4}$)-alkyl groups containing 7 to 10 carbon atoms such as benzyl, phenethyl, 3-phenylpropyl, α-methylbenzyl, α-ethylbenzyl, α-methylphenethyl, β-methylphenethyl and β-ethylphenethyl.

The condensed or non-condensed hetero-alicyclic group containing at least one atom of N, O and S as a ring-forming atom, as represented by $R^6$, includes a saturated or partially saturated hereto ring or rings composed of 4 to 8 members, and may be hetero rings containing not less than two hetero atoms, in which the same or not less than two kinds of atoms may exist as the ring-forming atom. The hetero-alicyclic group includes hetero-monoor bi-alicyclic groups, such as oxetanyl, thietanyl, azetidinyl, tetrahydrofuryl, tetrahydrothienyl, pyrrolidinyl, oxanyl (3,4,5,6-tetrahydro-2H-pyranyl), thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiazinyl, oxathianyl, perhydrodiazepinyl, oxathiepanyl, dioxepanyl, dithiepanyl, perhydrooxazepinyl, perhydrothiazepinyl, perhydrooxazocinyl, perhydrothiazocinyl, oxathiocanyl, perhydrodiazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydrobenzo[b]thienyl, 1,3-dihydrobenzo[c]thienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, -1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiadinyl, 2,3-dihydro-1,4-benzoxathienyl, 3,4-dihydro-2H-1,5-benzoxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydroisoquinolyl, perhydro-1-thianaphthyl and perhydro-2-thianaphthyl.

The said condensed or non-condensed hetero-alicyclic group may have at any substitative position thereof a substituent or two substituents, for example, lower ($C_{1-4}$-alkyl (e.g. methyl, ethyl, propyl, butyl), oxo, acyl such as $C_{1-5}$ alkanoyl (e.g. acetyl, propionyl), benzoyl, phenyl-lower-($C_{1-4}$)-alkoxycarbonyl (e.g. benzyloxycarbonyl), and lower-($C_{1-4}$)-alkoxycarbony (e.g. tert-butoxycarbonyl), aryl such as phenyl and naphthyl, and phenyl-lower-($C_{1-4}$)-alkyl such as benzyl, phenethyl, α-methylphenethyl and β-methylphenthyl. The phenyl group in the aryl group or phenyl-lower-alkyl group as the said substituent may optionally be substituted by halogen, such as fluorine, chlorine and bromine, lower-($C_{1-4}$)-alkoxy, such as methoxy, ethoxy, propoxy and butoxy, or lower-($C_{1-4}$)-alkyl, such as methyl, ethyl, propyl and butyl. Such substituted condensed or non-condensed hetero-alicyclic group includes, for example, those such as 1-phenylpiperidyl, 1-benzylpiperidyl, 4-phenylpiperidyl, 4-benzylpiperidyl, 1-acetylpiperidyl, 1-benzoylpiperidyl, 4-phenylpiperazinyl, 4-acetylpiperazinyl, 4-benzoylpiperazinyl, 1-oxoisoindolinyl, 1,3-dioxoisoindolinyl, 1,2,3,4-tetrahydro-1-oxoisoquinolyl and 1,2,3,4-tetrahydro-3-oxoisoquinolyl.

The alkylene chain represented by A includes, for example, straight-chain or branched-chain alkylene chains containing about 1 to 16 carbon atoms, whose examples include divalent groups, such as methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, propylene, ethylmethylene, 4-propylhexamethylene, 3,3-dimethylhexamethylene, 5,5-diethylhexamethylene and 3,5-dimethylnonamethylene. The said alkylene chains may have in the chain an unsaturated bond or unsaturated bonds (e.g. double bond, triple bond).

The divalent group represented by $CnH_{2n}$ forms methylene, ethylene or ethylidene, depending upon the value of n.

Compounds of the present invention are specifically disclosed, for example, in Table A.

TABLE A

| No. | $CnH_{2n}$ | $R^1, R^2$ | $R^3$ | $R^4$ | $R^5$ | —A— | $R^6$ |
|---|---|---|---|---|---|---|---|
| 1 | $CH_2$ | H | H | H | H | $-(CH_2)_2-$ | tetrahydropyran-4-yl (O) |
| 2 | $CH_2$ | H | $C_2H_5$ | H | H | $-(CH_2)_2-$ | tetrahydropyran-4-yl (O) |
| 3 | $CH_2$ | H | H | H | H | $-(CH_2)_2-$ | tetrahydrothiopyran-4-yl (S) |
| 4 | $CH_2$ | H | $C_2H_5$ | H | H | $-(CH_2)_2-$ | tetrahydrothiopyran-4-yl (S) |
| 5 | $CH_2$ | H | H | H | H | $-(CH_2)_2-$ | piperidin-4-yl (NH) ent |
| 6 | $CH_2$ | H | $C_2H_5$ | H | H | $-(CH_2)_2-$ | piperidin-4-yl (NH) |
| 7 | $CH_2$ | H | $C_2H_5$ | H | H | $-(CH_2)_2-$ | 1-benzoylpiperidin-4-yl |
| 8 | $CH_2$ | H | $C_2H_5$ | H | H | $-(CH_2)_2-$ | 1-acetylpiperidin-4-yl |
| 9 | $CH_2$ | H | $C_2H_5$ | H | H | $-(CH_2)_2-$ | 1-benzylpiperidin-4-yl |

TABLE A-continued
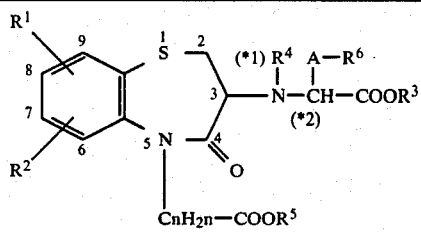
| No. | CnH2n | R¹,R² | R³ | R⁴ | R⁵ | —A— | R⁶ |
|---|---|---|---|---|---|---|---|
| 10 | CH₂ | H | C₂H₅ | H | H | —(CH₂)₂— | phthalimido |
| 11 | CH₂ | H | C₂H₅ | H | H | —(CH₂)₄— | phthalimido |
| 12 | CH₂ | H | C₂H₅ | H | H | —(CH₂)₆— | phthalimido |
| 13 | CH₂ | H | C₂H₅ | H | H | —(CH₂)₉— | phthalimido |
| 14 | CH₂ | H | C₂H₅ | H | H | —(CH₂)₂— | isoindolin-1-one |
| 15 | CH₂ | H | C₂H₅ | H | H | —(CH₂)₄ | isoindolin-1-one |
| 16 | CH₂ | H | H | H | H | —(CH₂)₄ | piperidin-1-yl |
| 17 | CH₂ | H | C₂H₅ | H | H | —(CH₂)₂— | 4-(benzyloxycarbonyl)piperidin-1-yl |
| 18 | CH₂ | H | C₂H₅ | CH₃ | H | —(CH₂)₂— | piperidin-3-yl |

TABLE A-continued

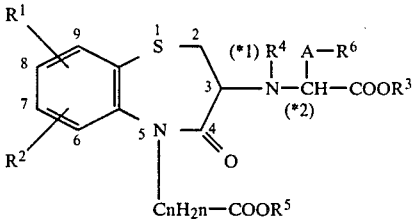

| No. | CnH2n | $R^1, R^2$ | $R^3$ | $R^4$ | $R^5$ | —A— | $R^6$ |
|---|---|---|---|---|---|---|---|
| 19 | —CH(CH3)— | H | $C_2H_5$ | H | H | $-(CH_2)_2-$ | tetrahydropyran-4-yl (O) |
| 20 | $CH_2$ | H | H | H | H | $-(CH_2)_4-$ | isoindolin-2-yl |
| 21 | $CH_2$ | 7-$CH_3$ | $C_2H_5$ | H | H | $-(CH_2)_2-$ | piperidin-4-yl (NH) |
| 22 | $CH_2$ | 7-$OCH_3$ | $C_2H_5$ | H | H | $-(CH_2)_2-$ | tetrahydrothiopyran-4-yl (S) |
| 23 | $CH_2$ | 7,8-$(CH_2)_3$ | $C_2H_5$ | H | H | $-(CH_2)_2-$ | tetrahydropyran-4-yl (O) |
| 24 | $CH_2$ | 7-Cl | $C_2H_5$ | H | H | $-(CH_2)_2-$ | tetrahydropyran-4-yl (O) |
| 25 | $CH_2$ | H | $(CH_2)_3-CH_3$ | H | H | $-(CH_2)_4-$ | phthalimido |
| 26 | $CH_2$ | H | H | H | H | $-(CH_2)_4-$ | piperazin-1-yl |
| 27 | $CH_2$ | H | H | H | H | $-(CH_2)_4-$ | 4-phenylpiperazin-1-yl |
| 28 | $CH_2$ | H | H | H | H | $-(CH_2)_4-$ | 4-(2-methoxyphenyl)piperazin-1-yl |

TABLE A-continued
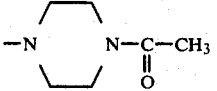
| No. | CnH2n | R¹,R² | R³ | R⁴ | R⁵ | —A— | R⁶ |
|-----|-------|-------|-----|-----|-----|------|-----|
| 29 | CH₂ | H | H | H | H | —(CH₂)₄— | 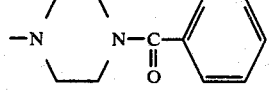 |
| 30 | CH₂ | H | H | H | H | —(CH₂)₄— | 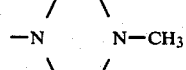 |
| 31 | CH₂ | H | H | H | H | —(CH₂)₄— | 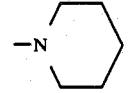 |
| 32 | CH₂ | H | C₂H₅ | H | C₂H₅ | —(CH₂)₄— | 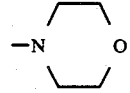 |
| 33 | CH₂ | H | H | H | H | —(CH₂)₄— | 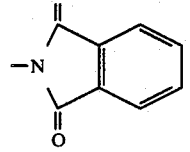 |
| 34 | CH₂ | H | C₂H₅ | H | H | —(CH₂)₃— | 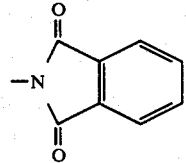 |
| 35 | CH₂ | H | C₂H₅ | H | H | —(CH₂)₅— | 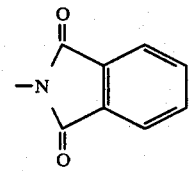 |
| 36 | CH₂ | H | C₂H₅ | H | H | —(CH₂)₇— | 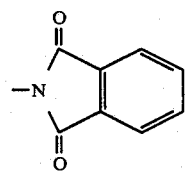 |
| 37 | CH₂ | H | C₂H₅ | H | H | —(CH₂)₈— | |

TABLE A-continued

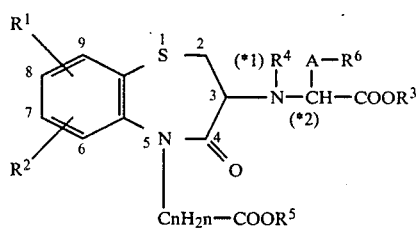

| No. | CnH2n | R¹,R² | R³ | R⁴ | R⁵ | —A— | R⁶ |
|---|---|---|---|---|---|---|---|
| 38 | CH₂ | H | H | H | H | —(CH₂)₄— | tetrahydroisoquinolinyl (N-linked) |
| 39 | CH₂ | H | H | H | H | —(CH₂)₂— | 1-oxo-tetrahydroisoquinolin-2-yl |
| 40 | CH₂ | H | C₂H₅ | H | C₂H₅ | —(CH₂)₂— | piperidin-4-yl (NH) |
| 41 | CH₂ | H | C₂H₅ | H | H | —(CH₂)₄— | piperidin-4-yl (NH) |
| 42 | CH₂ | H | H | H | H | —(CH₂)₄— | piperidin-4-yl (NH) |
| 43 | CH₂ | H | H | H | H | —(CH₂)₄— | 2,3,4,5-tetrahydro-1H-3-benzazepin-3-yl |
| 44 | CH₂ | H | H | H | H | —(CH₂)₄— | 4-benzylpiperidin-1-yl |
| 45 | CH₂ | 7-CF₃ | C₂H₅ | H | H | —(CH₂)₂— | tetrahydropyran-4-yl |
| 46 | CH₂ | H | H | H | H | —(CH₂)₆— | piperidin-1-yl |
| 47 | CH₂ | H | C₂H₅ | H | C₂H₅ | —(CH₂)₄— | phthalimid-2-yl |

TABLE A-continued

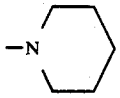

| No. | CnH2n | R¹,R² | R³ | R⁴ | R⁵ | —A— | R⁶ |
|-----|-------|-------|----|----|----|-----|-----|
| 48 | $CH_2$ | H | $C_2H_5$ | H | H | $-(CH_2)_4-$ | 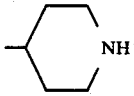 |
| 49 | $CH_2$ | H | H | H | H | $-(CH_2)_5-$ | 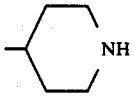 |
| 50 | $CH_2$ | H | H | H | H | $-(CH_2)_6-$ | 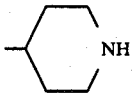 |
| 51 | $CH_2$ | H | H | H | H | $-(CH_2)_7$ | 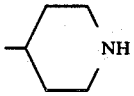 |
| 52 | $CH_2$ | H | H | H | H | $-(CH_2)_8-$ | 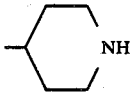 |
| 53 | $CH_2$ | H | H | H | H | $-(CH_2)_9-$ | 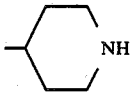 |
| 54 | $CH_2$ | H | H | H | H | $-(CH_2)_3-$ | 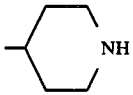 |
| 55 | $CH_2$ | H | $C_2H_5$ | H | H | $-(CH_2)_5-$ | |

The compound (I) of the present invention possesses asymmetric carbon in the molecule, and both stereoisomers of the R and S configurations are included in the scope of the present invention. Among others, the compound in which the carbon atom bearing the symbol (*1) has the absolute configuration of R and the carbon atom bearing the symbol (*2) has the absolute configuration of S is preferable.

Salts of the compounds (I) include pharmaceutically acceptable salts, such as salts with inorganic acids being exemplified by hydrochloride, hydrobromide, sulfate, nitrate, phosphate, etc. salts with organic acids being exemplified by acetate, tartarate, citrate, fumarate, maleate, toluenesulfonate and methanesulfonate, etc., metal salts being exemplified by sodium salts, potassium salts, calcium salts, aluminum salts, etc., and salts with bases being exemplified by triethylamine salts, guanidine salts, ammonium salts, hydrazine salts, quinine salts, cinchonine salts, etc. Preferred are the compounds of the formula

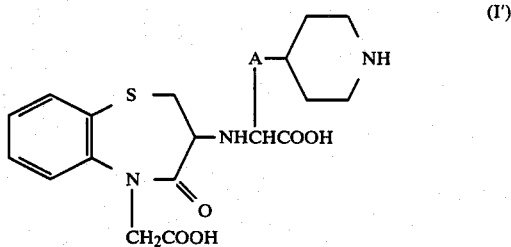

(I')

wherein A is C$_{2-9}$ alkylene, and their pharmacentucally acceptable salts.

The compound (I) of the present invention can be produced, for example, by subjecting a compound of the formula:

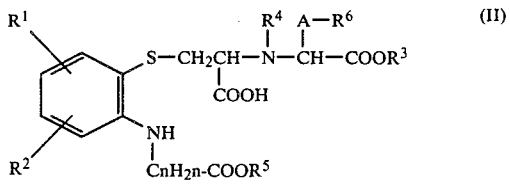

(II)

[wherein each of the symbols is as defiend hereinbefore] to a dehydrative ring-closure reaction. The said dehydrative ring-closure reaction can be carried out, for example, by means of an ordinary amide bond formation reaction in peptide synthesis. Thus, the reaction can be conducted by employing such a peptide forming reagent as dicyclohexylcarbodiimide, N,N'-carbonyldiimidazole, diphenylphosphorylazide and diethyl phosphorocyanidate solely or adding an ordinary inorganic acid (e.g. hydrogen chloride, sulfuric acid, nitric acid, hydrogen bromide) to allow protonation of the amino group of the compound (II) and then condensing the protonated compound with phenols, such as 2,4,5-trichlorophenol, pentachlorophenol, pentafluorophenol, 2-nitrophenol or 4-nitrophenol, or N-hydroxy compounds, such as N-hydroxysuccinimide, 1-hydroxybenzotriazole and N-hydroxypiperidine, in the presence of such a catalyst as dicyclohexylcarbodiimide to convert to the activated ester derivative, followed by cyclization. The cyclization reaction, whether the compound (II) is cyclized as such or after converting to its activated ester, can be promoted by adding preferably an organic base, for example, quaternary ammonium salt or tertiary amine (e.g. triethylamine, N-methylpiperidine). The reaction temperature is normally $-20°$ to $+50°$ C., preferably in the neighborhood of room temperature, and a solvent which is normally employed includes, for example, dioxane, tetrahydrofuran, acetonitrile, pyridine, N,N-dimethylformamide, N,N-dimethylacetamide, dimethylsulfoxide, N-methylpyrrolidone, chloroform, methylene chloride, etc., which may be used alone or as a mixture thereof.

The compound (I) of the present invention can also be produced, for example, by reacting a compound of the formula:

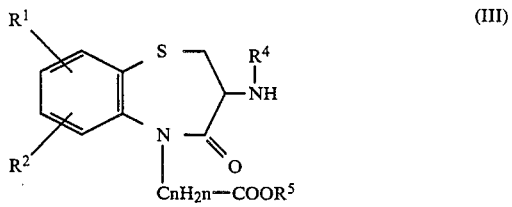

(III)

[wherein each of the symbols is as defined hereinbefore] with a compound of the formula:

(IV)

[herein W$^a$ is halogen or a group represented by the formula R$^a$SO$_2$—O— (wherein R$^a$ is lower-(C$_{1-4}$)-alkyl, trifluoromethyl, phenyl or p-tolyl); other symbols are as defined hereinbefore]. The reaction can be allowed to proceed by maintaining normally both of the compounds in the absence or presence of water or other organic solvent (e.g. acetonitrile, dimethylformamide, dimethylsulfoxide, tetrahydrofuran, benzene, toluene) solely or a mixture thereof within the temperature range of about $-20°$ to $+150°$ C. On this occasion, it is possible for the purpose of acceleration of the reaction rate to allow a base, such as potassium carbonate, sodium hydroxide, sodium hydrogencarbonate, pyridine and triethylamine, to coexist in the reaction system.

Also, the compound (I) of the present invention can be produced, for example, by reacting a compound of the formula:

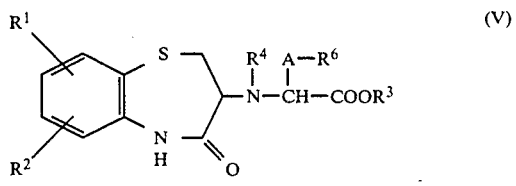

(V)

[wherein each of the symbols is as defined hereinbefore] with a compound of the formula:

(VI)

[wherein W$^b$ is halogen or a group represented by the formula R$^b$SO$_2$—O— (wherein R$^b$ is lower-(C$_{1-4}$)-alkyl, trifluormethyl, phenyl or p-tolyl); other symbols are as defined hereinbefore]. The reaction can be allowed to proceed by maintaining both of the compounds in water or other organic solvent (e.g. acetonitrile, dimethylformamide, dimethylsulfoxide, tetrahydrofuran, benzene, toluene) solely or a mixture thereof within the temperature range of about $-20°$ to $+150°$ C. On this occasion, it is possible to allow a base, such as potassium carbonate, sodium hydroxide and sodium hydride, to coexist in the reaction system.

The compound of the formula (I) wherein R$^4$ is hydrogen can be produced, for example, by subjecting a compound of the formula:

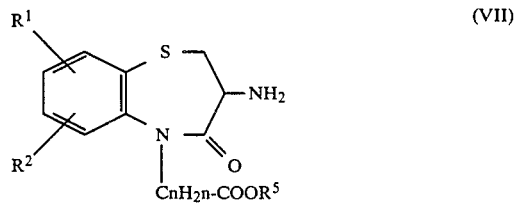

(VII)

[wherein each of the symbols is as defined hereinbefore] and a compound of the formula:

(VIII)

[wherein each of the symbols is as defined hereinbefore] to a condensation reaction under reductive conditions.

The said reductive conditions include reaction conditions of catalytic reduction using a metal, such as platinum, palladium and rhodium, or a mixture thereof with an aribitrary support as a catalyst; reduction with a metal hydride compound, such as lithium aluminum hydride, lithium borohydride, lithium cyanoborohydride, sodium borohydride and sodium cyanoborohydride; reduction with metallic sodium, metallic magnesium, etc. and alcohols; reduction with a metal, such as iron and zinc, and an acid such as hydrochloric acid and acetic acid; electrolytic reduction; reducing with a reducing enzyme, and so forth. The above reaction is normally carried out in the presence of water or an organic solvent (e.g. methanol, ethanol, ethyl ether, dioxane, methylene chloride, chloroform, benzene, toluene, acetic acid, dimethylformamide, dimethylacetamide), and the reaction temperature varies with means of reduction employed, but generally is preferably in the range of $-20°$ C. to $+100°$ C. The reaction can be conducted at atmospheric pressure to achieve the desired object satisfactorily but may also be carried out under pressure or under reduced pressure according to the circumstances.

Also, the compound of the formula (I) wherein $R^4$ is hydrogen can be produced, for example, by subjecting a compound of the formula:

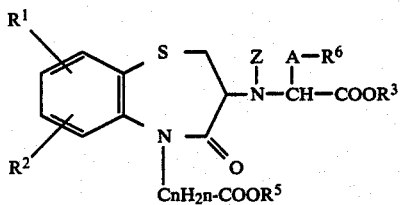

(IX)

[wherein Z is a protective group removable by hydrolysis or catalytic reduction; other symbols are as defined hereinbefore] to a hydrolysis or catalytic reduction reaction. As the protective group removable by hydrolysis as represented by Z in (IX), there are used all kinds of acyl groups and trityl groups, and benzyloxycarbonyl, tert-butoxycarbonyl, trifluoroacetyl trityl, etc., among others, are advantageous in the case of reactions under relatively mild reaction conditions. The protective group removable by catalytic reduction as represented by Z includes, for example, benzyl, diphenylmethyl, benzyloxycarbonyl, etc. The hydrolysis reaction in the said method is carried out in water or an organic solvent, such as methanol, ethanol, dioxane, pyridine, acetic acid, acetone and methylene chloride, or a mixture thereof, and for the purpose of accelerating the reaction rate, it can also be conducted by adding an acid (e.g. hydrogen chloride, hydrogen bromide, hydrogen iodide, hydrogen fluoride, sulfuric acid, methanesulfonic acid, p-toluenesulfonic acid, trifluoroacetic acid) or a base (e.g. sodium hydroxide, potassium hydroxide, potassium carbonate, sodium hydrogencarbonate, sodium acetate, triethylamine). The above reaction is carried out normally within the temperature range of $-20°$ to $+150°$ C. The catalytic reduction reaction in the said method is conducted in water or an organic solvent, such as methanol, ethanol, dioxane and tetrahydrofurane, or a mixture thereof in the presence of an appropriate catalyst, such as platinum and palladium-carbon. This reaction is carried out at atmospheric pressure or under pressure up to about 150 kg/cm$^2$ and at ordinary temperature or at a temperature up to $+150°$ C., but the reaction generally proceeds satisfactorily at ordinary temperature and at atmospheric pressure.

The compound of the formula (I) wherein $R^4$ is hydrogen can also be produced, for example, by subjecting the cyano group in the compound of the formula:

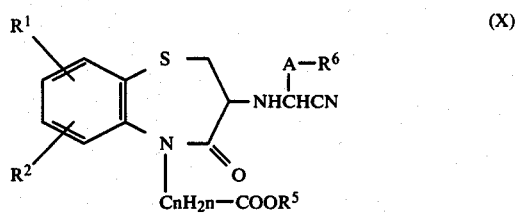

(X)

[wherein each of the symbols is as defined hereinbefore] to solvolysis.

The above solvolysis reaction is carried out in water or an organic solvent, such as methanol, ethanol, dioxane, pyridine, acetic acid, acetone and methylene chloride, or a mixture thereof, and can also be conducted by adding an acid (e.g. hydrogen chloride, hydrogen bromide, hydrogen iodide, hydrogen fluoride, sulfuric acid, methanesulfonic acid, p-toluenesulfonic acid, trifluoroacetic acid, acid resin) or a base (e.g. sodium hydroxide, potassium hydroxide, potassium carbonate, sodium hydrogencarbonate, sodium acetate, triethylamine) for the purpose of accelerating the reaction rate. The reaction is normally carried out at a temperature within the range of about $-20°$ to $+150°$ C.

The compound (I) of the present invention wherein the atom in the group $R^6$ being linked to the group A is a nitrogen atom can also be produced, for example, by allowing a compound of the formula:

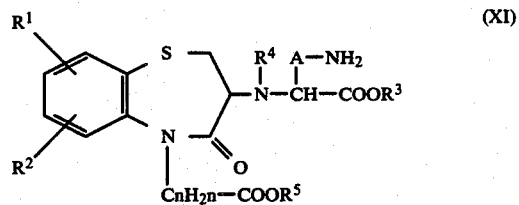

(XI)

[wherein each of the symbols is as defined hereinbefore] and a compound of the formula:

(XII)

[wherein X is a ring-forming atomic group and represents $R^6$ as the formula

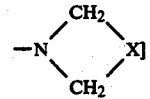

to undergo a condensation reaction under reductive conditions.

The said reductive conditions include reaction conditions of catalytic reduction using a metal, such as platinum, palladium and rhodium, or a mixture thereof with an arbitrary support as a catalyst; reduction with a metal hydride compound, such as lithium aluminum hydride, lithium borohydride, lithium cyanoborohydride, sodium borohydride and sodium cyanoborohydride; reduction with metallic sodium, metallic magnesium, etc. and alcohols; reduction with a metal, such as iron and zinc, and an acid, such as hydrochloric acid and acetic acid; electrolytic reduction; reduction with a reducing enzyme, and so forth. The above reaction is normally carried out in the presence of water or an organic solvent (e.g. methanol, ethanol, ethyl ether, dioxane, methylene chloride, chloroform, benzene, toluene, acetic acid, dimethylformamide, dimethylacetamide), and the reaction temperature varies with means of reduction employed, but generally is preferably in the range of $-20°$ C. to $+100°$ C. This reaction can be conducted at atmospheric pressure to achieve the desired object satisfactorily but may also be carried out under pressure or under reduced pressure according to the circumstances.

Also, the compound (I) of the present invention wherein the atom in the group being linked to the group A is a nitrogen atom can be produced, for example, by reacting a compound of (XI) with a compound of the formula:

   (XIII)

[wherein $W^c$ is halogen or a group represented by the formula $R^cSO_2$—O— (wherein $R^c$ is lower($C_{1-4}$)alkyl, trifluoromethyl, phenyl or p-tolyl); Y is a ring-forming atomic group and represents the group $R^6$ as

].

The reaction is allowed to proceed by maintaining both of the compounds in a suitable solvent or a mixture thereof within the temperature range of about $-20°$ to $+150°$ C. On this occasion, it is also possible for the purpose of accelerating the reaction rate to allow a base, such as potassium carbonate, sodium hydroxide, sodium hydrogencarbonate, pyridine and triethylamine, to coexist in the reaction system as a deacidifying agent.

The compound of the formula (I) wherein $R^3$ is hydrogen or/and $R^5$ is hydrogen can be produced by subjecting a compound of the formula (I) wherein $R^3$ is lower alkyl or/and $R^5$ is lower alkyl to a hydrolysis or elimination reaction, and also by subjecting the compound of the formula (I) wherein $R^3$ is benzyl or/and $R^5$ is benzyl to a catalytic reduction reaction. The hydrolysis or elimination reaction in the said method is carried out in water or an organic solvent, such as methanol, ethanol, ethyl acetate, chloroform, tetrahydrofuran, dioxane, pyridine, acetic acid, acetone and methylene chloride, or a mixture thereof, and can also be conducted by adding an acid (e.g. hydrogen chloride, hydrogen bromide, hydrogen fluoride, hydrogen iodide, sulfuric acid, methanesulfonic acid, p-toluenesulfonic acid, trifluoroacetic acid) or a base (e.g. sodium hydroxide, potassium hydroxide, potassium carbonate, sodium hydrogencarbonate, sodium carbonate, sodium acetate). The above reaction is normally carried out at a temperature within the range of $-20°$ to $+150°$ C. The catalytic reduction reaction in the said method is carried out in water or an organic solvent, such as methanol, ethanol, ethyl acetate, dioxane and tetrahydrofuran, or a mixture thereof in the presence of an appropriate catalyst, such as palladium-carbon. This reaction is conducted at atmospheric pressure or under pressure up to about 150 kg/cm² and at ordinary temperature or at a temperature up to $+150°$ C.

The compound of the formula (I) wherein $R^3$ is lower alkyl or aralkyl or/and $R^5$ is lower alkyl or aralkyl can be produced by allowing the compound of the formula (I) wherein $R^3$ is hdyrogen or/and $R^5$ is hydrogen to undergo a condensation reaction with a compound of the formula:

$$R^{3'}—OH \qquad (XIV)$$

or the formula:

$$R^{5'}—OH \qquad (XV)$$

[wherein $R^{3'}$ and $R^{5'}$ are independently lower alkyl or aralkyl]. The said condensation reaction conditions include, for example, reaction conditions involving the use of a condensing agent (e.g. dicyclohexylcarbodiimide, carbonyldiimidazole, diethyl phosphorocyanidate, diphenylphosphorylazide) or reaction conditions involving the use of an acid catalyst (e.g. hydrogen chloride, hydrogen bromide, p-toluenesulfonic acid). The reaction is allowed to proceed in a suitable solvent or a mixture thereof or in the absence of a solvent at a temperature within the range of about $-20°$ to $+150°$ C.

The compound of the formula (I) wherein $R^3$ is lower alkyl or aralkyl or/and $R^5$ is lower alkyl or aralkyl can also be produced by reacting the compound of the formula (I) wherein $R^3$ is hydrogen or/and $R^5$ is hydrogen with a compound of the formula:

$$R^{3''}—W^d \qquad (XVI)$$

or the formula:

$$R^{5''}—W^d \qquad (XVII)$$

[wherein $R^{3''}$ and $R^{5''}$ are lower alkyl or aralkyl; $W^d$ is halogen or a group represented by the formula $R^dSO_2$—O— (wherein $R^d$ is lower-($C_{1-4}$)-alkyl, trifluoromethyl, phenyl or p-tolyl)] The reaction is allowed to proceed in a suitable solvent at a temperature within the range of about $-20°$ to $+150°$ C. in the presence of a base (e.g. potassium carbonate, sodium carbonate, sodium hydrogencarbonate, potassium hydrogencarbonate).

The compound (I) of the present invention wherein the group $R^6$ contains an unsubstituted imino group can be produced by subjecting the compound of the formula (I) wherein the group $R^6$ contains a benzylimino or acylimino group to a catalytic reduction, elimination or solvolysis reaction.

The catalytic reduction reaction in the said method is carried out in water or an organic solvent, such as methanol, ethyl acetate, ethanol, dioxane and tetrahydrofuran, or a mixture thereof in the presence of an appropriate catalyst, such as palladium-carbon. This reaction is conducted at atmospheric pressure or under pressure up to about 150 kg/cm² and at ordinary temperature or at a temperature up to $+150°$ C.

The solvolysis or elimination reaction in the said method is carried out in water or an organic solvent, such as methanol, ethanol, ethyl acetate, chloroform, tetrahydrofuran, dioxane, pyridine, acetic acid, acetone and methylene chloride, or a mixture thereof, and can also be conducted by adding an acid (e.g. hydrogen chloride, hydrogen bromide, hydrogen fluoride, hydrogen iodide, sulfuric acid, methane-sulfonic acid, p-toluenesulfonic acid, trifluoroacetic acid) or a base (e.g. sodium hydroxide, potassium hydroxide, potassium carbonate, sodium hydrogencarbonate, sodium carbonate sodium acetate). The above reactions are normally carried out at a temperature within the range of $-20°$ to $+150°$ C.

The compound of the formula (I) wherein the group $R^6$ has therein an imino group substituted by lower-$(C_{1-4})$-alkyl, aralkyl or acyl can be obtained by reacting the compound of the formula (I) wherein the group $R^6$ has therein an unsubstituted imino group with a compound of the formula:

$$R^7-W^e \qquad (XVIII)$$

[wherein $R^7$ is lower alkyl, aralkyl or acyl; $W^e$ is halogen or a group represented by the formula $R^eSO_2-O-$ (wherein $R^e$ is lower $(C_{1-4})$ alkyl, trifluoromethyl, phenyl or p-tolyl)]. The reaction is allowed to proceed by maintaining both of the compounds in a suitable solvent within the temperature range of about $-20°$ to $+150°$ C. On this occasion, it is possible for the purpose of accelerating the reaction rate to allow a base, such as potassium carbonate, sodium hydroxide, sodium hydrogencarbonate, pyridine and triethylamine, to coexist in the reaction system as a deacidifying agent.

Also, the compound of the formula (I) wherein the group $R^6$ has therein an imino group substituted by lower-$(C_{1-4})$-alkyl or aralkyl can be obtained by allowing the compound of the formula (I) wherein the group $R^6$ has therein an unsubstituted imino group and a lower-$(C_{1-4})$-alkylaldehyde or aralkylaldehyde to undergo condensation under reductive conditions.

The said reductive conditions include reaction conditions of catalytic reduction using a metal, such as platinum, palladium and rhodium, or a mixture thereof with an arbitrary support as a catalyst; reduction with a metal hydride compound, such as lithium aluminum hydride, lithium borohydride, lithium cyanoborohydride, sodium borohydride and sodium cyanoborohydride; reduction with metallic sodium, metallic magnesium, etc. and alcohols; reduction with a metal, such as iron and zinc, and an acid, such as hydrochloric acid and acetic acid; electrolytic reduction; reduction with a reducing enzyme, and so forth. The above reaction is normally carried out in the presence of water or an organic solvent (e.g. methanol, ethanol, ethyl ether, dioxane, methylene chloride, chloroform, benzene, toluene, acetic acid, diemthylformamide, dimethylacetamide), and the reaction temperature varies with means of reduction, and generally is preferably in the range of $-20°$ C. to $+100°$ C. This reaction can be conducted at atmospheric pressure to achieve the desired object satisfactorily, but may be carried out under pressure or under reduced pressure depending on the circumstances.

The compound of the formula (I) wherein the group $R^6$ has therein an acylimino group can also be produced by reacting the compound of the formula (I) wherein the group $R^6$ has therein an unsubstituted imino group with a compound of the formula:

$$(R^{7'})_2O \qquad (XIX)$$

[wherein $R^{7'}$ is acyl].

The reaction is allowed to proceed by maintaining both of the compounds in water or a suitable solvent or a mixture thereof within the temperature range of about $-20°$ to $+150°$ C. On this occasion, it is possible for the purpose of accelrating the reaction rate to allow a base, such as potassium carbonate, sodium hydroxide, sodium hydrogencarbonate, pyridine, and triethylamine, to coexist in the reaction system as a deacidifying agent.

The compound of the formula (I) wherein $R^4$ is lower alkyl can also be produced by subjecting the compound of the formula (I) wherein $R^4$ is hydrogen to an alkylation reaction.

The above alkylation reaction includes, for example, a reductive alkylation reaction involving the reaction with a lower alkyl-$(C_{1-4})$-aldehyde under reductive conditions [the reductive conditions include reaction conditions of catalytic reduction using a metal, such as platinum, palladium and rhodium, or a mixture thereof with an arbitrary support as a catalyst; reduction with a metal hydride compound, such as lithium aluminum hydride, lithium borohydride, lithium cyanoborohydride, sodium borohydride and sodium cyanoborohydride; reduction with metallic sodium, metallic magnesium, etc. and alcohols; reduction with a metal, such as iron and zinc, and an acid, such as hydrochloric acid and acetic acid; electrolytic reduction; reduction with a reducing enzyme, and so forth. The reaction is normally carried out in the presence of water or an organic solvent (e.g. methanol, ethanol, ethyl ether, dioxane, methylene chloride, chloroform, benzene, toluene, acetic acid, dimethylformamide, dimethylacetamide), and the reaction temperature varies with means of reduction employed, and generally is preferably in the range of $-20°$ C. to $+100°$ C. This reaction can be conducted at atmospheric pressure to achieve the desired object satisfactorily, but may also be carried out under pressure or under reduced pressure according to the circumstances-]or an alkylation reaction (the reaction conditions include, for example, reaction conditions in which both of the compounds are maintained in a suitable solvent or a mixture thereof within the temperature range of $-20°$ to $+150°$ C. On this occasion, it is also possible for the purpose of accelerating the reaction rate to allow a base, such as potassium carbonate, sodium hydroxide, sodium hydrogencarbonate, pyridine,and triethylamine, to co-exist in the reaction system as a deacidifying agent) involving the reaction with a compound of the formula:

$$R^4-W^f \qquad (XX)$$

[wherein $W^f$ is halogen or a group represented by the formula $R^fSO_2-O-$ (wherein $R^f$ is lower$(C_{1-4})$ alkyl, trifluoromethyl, phenyl or p-tolyl); $R^4$ is as defined hereinbefore].

The salt of the compound (I) can be produced by the reaction per se for producing the compound (I), and if desired, it can also be produced by adding an acid, alkali or base to the compound (I).

The object compound (I) of the present invention thus obtained can be isolated from the reaction mixture by utilizing conventional separation and purification means, for example, means such as extraction, concentration, neutralization, filtration, recrystallization, column chromatography and thin layer chormatography.

The compound (I) can exist in at least four stereoisomers. These individual isomers and a mixture thereof, naturally, all fall within the scope of the present invention, and such isomers can be produced individually, if desired. For example, a single optical isomer of the compound (I) can be obtained by carrying out the above reaction using a single isomer each of the starting compounds (II), (III), (IV), (V), (VII), (IX), (X) and (XI), and when the product is a mixture of not less than two kinds of isomers, it can also be separated into individual isomers by separating means, such as methods of forming salts with optically active acids (e.g. camphorsulfonic acid, tartaric acid, dibenzoyltartaric acid, etc.) or optically active bases (e.g. cinchonine, cinchonidine, quinine, quinidine, α-methylbenzylamine, dehydroabiethylamine, etc.), a variety of chromatographic techniques and fractional recrystallization.

The compounds of the present invention, namely the condensed seven-membered ring compounds represented by the formula (I) and salts thereof, exhibit inhibitory activities on angiotensin converting enzyme and bradykinin decomposing enzyme (kininase), etc. in animals, in particular mammals (e.g. human, dog, cat, rabbit, guinea pig, rat), and are useful, for example, as drugs for diagnosis, prevention and treatment of hypertension and hypertension-induced circulatory diseases, such as cardiopathy and cerebral apoplexy. The compound of the present invention is of low toxicity, well adsorbed on oral administration, excellently long-lasting in effect and highly stable, and it, when being used as the abovementioned drugs, can therefore be safely administered orally or parenterally, per se or in admixture with suitable, pharmaceutically acceptable carriers, excipients or diluents in various pharmaceutical formulations, such as powders, granules, tablets, capsules and injectable solutions. While the dosage level varies depending upon the conditions of the diseases to be treated as well as the administration route used, in the case of administration to human adult for the purpose of treatment of renal or essential hypertension, for example, the compound may be desirably administered orally at a single dose of normally about 0.02 to 10 mg/kg, preferably about 0.02 to 2 mg/kg, more preferably about 0.04 to 0.8 mg/kg, or intravenously at a single dose of about 0.002 to 1 mg/kg, preferably about 0.02 to 1 mg/kg, more preferably about 0.02 to 0.2 mg/kg, about once to 3 times per day, preferably once to twice per day, according to the conditions.

The starting compounds (II), (III), (V), (VII), (IX), (X) and (XI) of the present invention can be easily prepared, for example, by the methods as illustrated in the following reaction schema.

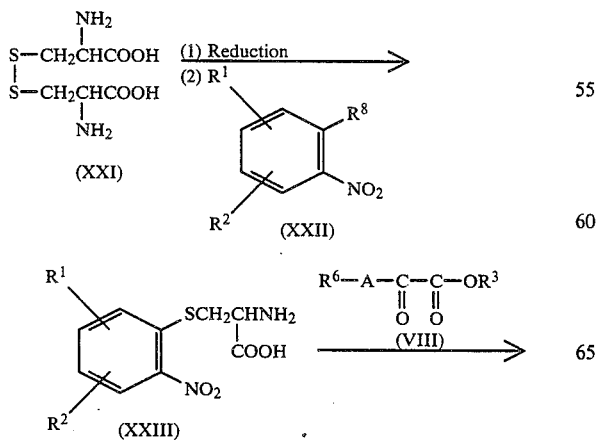

-continued
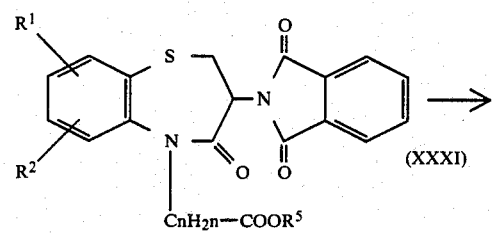
(XXXI)
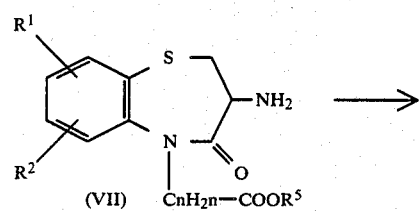
(VII)
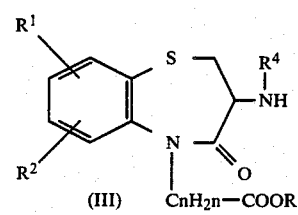
(III)
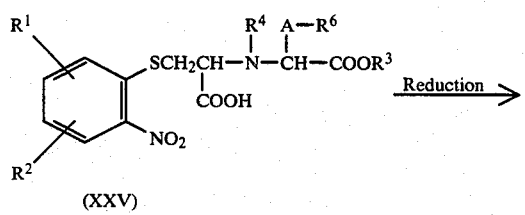
(XXV)
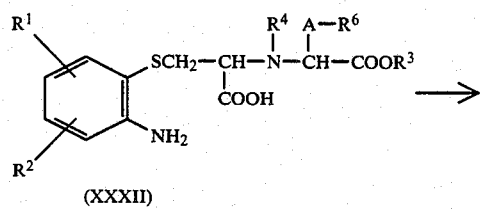
(XXXII)
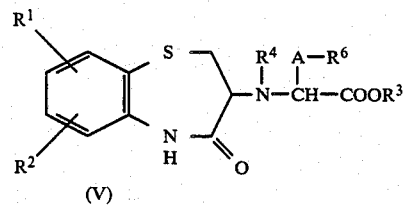
(V)
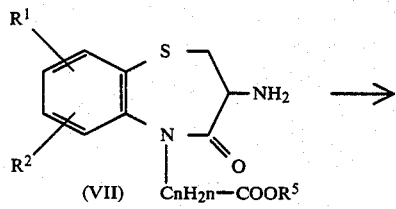
(VII)
-continued
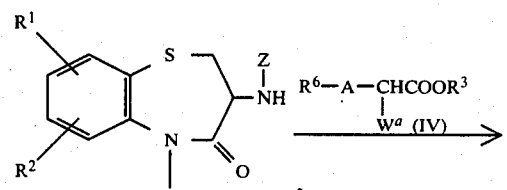
(XXXIII)
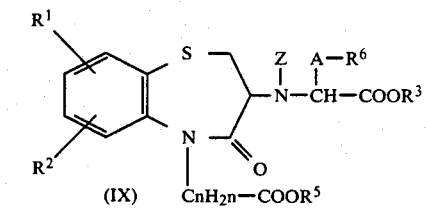
(IX)
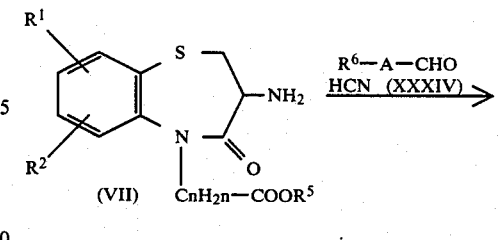
(VII)
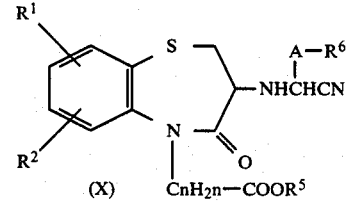
(X)
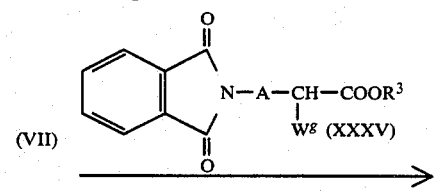
(VII)
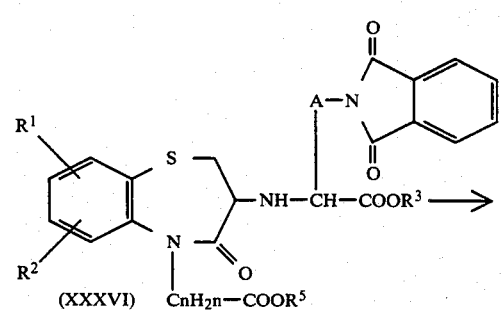
(XXXVI)

-continued

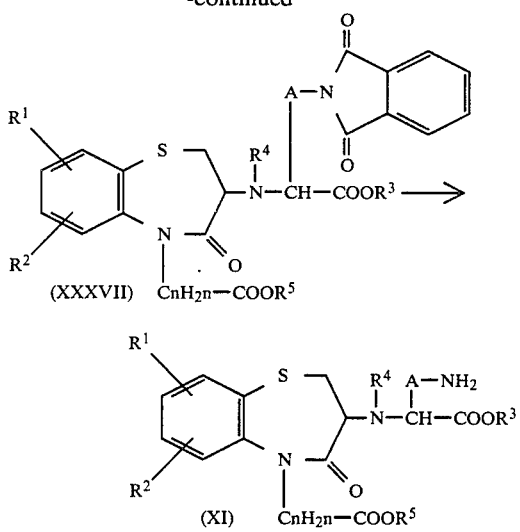

In the above reaction formulae, $R^8$ is halogen or a diazonium group; $W^g$ is halogen or a group represented by the formula $R^gSO_2$—O— (wherein $R^g$ is lower ($C_{1-4}$) alkyl, trifluoromethyl, phenyl or p-tolyl); and other symbols are as defined hereinbefore.

Referring in more particular to the process for producing the compound (II) as shown in the above reaction schema, cystine (XXI) used as a starting compound is derived into cysteine, which is reacted with the compound (XXII) to produce the compound (XXIII). The reaction of the compounds (XXIII) and (VIII) can be carried out in the same manner as the reaction between the compounds (VII) and (VIII). The reaction of (XXIV)→(XXV) is an ordinary alkylation reaction, and can be allowed to proceed, for example, by the reaction with a lower alkylaldehyde corresponding to the group $R^4$ under reductive conditions. The compound (XXV) is subjected to a conventional reduction reaction of the nitro group to the amino group, followed by an alkylation reaction to produce the compound (II).

In the method for producing the compounds (III) and (VII), the amino group of the compound (XXVI), in the first place, is protected with a suitable amino protecting group (e.g. phthaloyl group) to produce the compound (XXVIII). This reaction is allowed to proceed easily by condensation of the compound (XXVI) with the compound (XXVII) in the presence of a base (e.g. sodium carbonate, potassium carbonate, potassium hydrogencarbonate) normally at a temperature in the range of 0° to +100° C. The reaction of (XXVIII)→(XXIX) is a reduction reaction of the nitro group to the amino group, and conventionally known reduction techniques can be employed. The reduction techniques include catalytic reduction using as a catalyst for example palladium-carbon, palladium supported with barium sulfate, sulfided palladium, platinum, etc., reduction with a metal such as zinc, tin, stannous chloride and iron and an acid or alkali, and so forth. The dehydrative ring-closure reaction of the resultant compound (XXIX) to the compound (XXX) can be advantageously carried out in the presence of a conventionally known dehydrative coupling agent. Such dehydrative coupling agent includes, for example, dicyclohexylcarbodiimide, carbonyldiimidazole, diethyl phosphorocyanidate, etc. As a solvent, there are used, for example, dioxane, methylene chloride, acetonitrile, N,N-dimethylformamide, tetrahydrofuran,etc., and the reaction is normally carried out at a temperature in the range of −10° to +100° C. For the purpose of allowing the reaction to proceed advantageously, in such a case, it may also be possible to add such a base as triethylamine and pyridine to the reaction solution as a catalyst. The preparation of the compound (XXXI) through a condensation reaction between the compounds (XXX) and (VI) can be effected normally by condensation in a solvent such as N,N-dimethylformamide, dimethylsulfoxide and acetonitrile in the presence of such a base as sodium hydride and potassium carbonate at a temperature in the range of −10° to +100° C. Then, the reaction of (XXXI)→(VII) can be conducted by treatment with hydrazine hydrate in a solvent such as methanol, ethanol and dioxane at a temperature in the range of −10° to +100° C. to produce the compound (VII).

The reaction of (VII)→(III) is an ordinary alkylation reaction, and such an alkylation method includes, for example, a procedure of reacting with a lower alkylaldehyde corresponding to the group $R^4$ under reductive conditions and a procedure of reacting with the compound (XX) in a suitable solvent.

The compound (V) can be prepared by subjecting the compound (XXV) to an ordinary reduction reaction of the nitro group to the amino group, followed by a dehydrative ring-closure reaction.

In the process for producing the compound (IX), the compound (XXXIII) can be prepared by subjecting the compound (VII) to a per se known amino protecting reaction for amino acids. The reaction of (XXXIII)→(IX) is allowed to proceed by maintaining the compounds (XXXIII) and (IV) in a suitable solvent within the temperature range of −20° to +150° C. In such a case, it is also possible for the purpose of accelerating the reaction rate to allow such a base as potassium carbonate, sodium hydroxide, sodium hydrogencarbonate, pyridine and triethylamine to coexist in the reaction system as a deacidifying agent.

In the process for producing the compound (X), the compound (X) can be obtained from the compounds (VII) and (XXXIV) and hydrogen cyanide as starting compounds according to the Strecker reaction which is per se known.

In the process for producing the compound (XI), the compound (XXXVI) can be obtained by the reaction between the compounds (VII) and (XXXV). As a solvent, there are used acetonitrile, methyl ethyl ketone, acetone, tetrahydrofuran, methylene chloride, dimethylsulfoxide, dimethylformamide, etc., and the reaction is normally carried out at a temperature in the range of −10° to +150° C. In such a case, it is also possible for the purpose of allowing the reaction to proceed advantageously to add a base, such as triethylamine, pyridine, potassium carbonate and sodium carbonate, and potassium iodide, etc. The reaction of (XXXVI)→(XXXVII) can be carried out in the same manner as the reaction of (XXIV)→(XXV), while the reaction of (XXXVII)→(XI) can be conducted in the same manner as the reaction of (XXXI)→(VII).

The compounds (IV) and (VIII) which are used in the production of the compound (I) of the present invention can be readily produced, for example, by the process as shown in the following reaction schema.

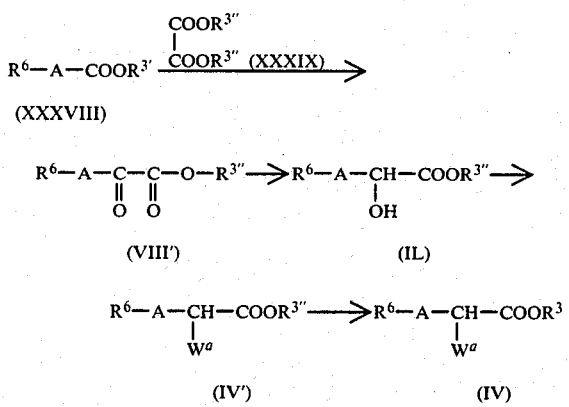

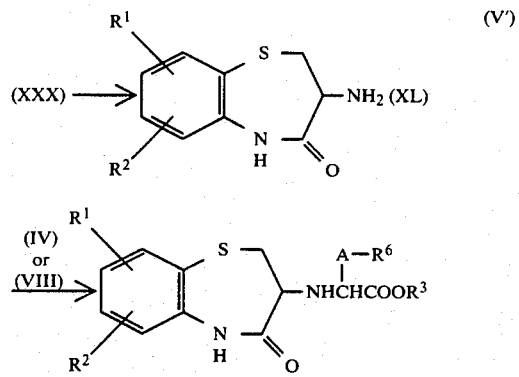

In the above reaction schema, R³' and R³" are independently lower alkyl or aralkyl corresponding to R³; other symbols are as defined hereinbefore.

The compound (VIII') can be prepared by allowing the compounds (XXXVIII) and (XXXIX) to undergo condensation in the presence of such a base as sodium ethoxide, followed by heating in the presence of aqueous dimethylsulfoxide, lithium chloride, etc. The compound (IV') can be produced by subjecting the compound (VIII') to a per se known reduction reaction and then subjecting the resulting compound (IL) to a per se known halogenation reaction or sulfonylation reaction.

The starting compound (XXXVIII) can be readily produced, for example, by subjecting a compound of the formula:

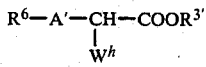

[wherein $W^h$ is halogen;

replaces A; other symbols are as defined hereinbefore] to a per se known reduction reaction.

When $R^6$ has therein a group which may interfere with the reaction, the reaction may be carried out by protecting the said group with a protective group, such as lower-($C_{1-5}$)-alkanoyl (e.g. acetyl), benzoyl, phenyl-lower-($C_{1-4}$)alkoxycarbonyl (e.g. benzyloxycarbonyl), lower-($C_{1-4}$)-alkoxycarbonyl (e.g. tert-butoxycarbonyl), etc.

The compounds of the formulae (VIII'), (IL) and (IV') wherein $R^3$ is hydrogen can be readily produced by subjecting the compounds (VIII'), (IL) and (IV') respectively to a hydrolysis reaction.

The compounds of the formulae (VIII) and (IV) wherein $R^6$ is 4-piperidyl which may be substituted are novel compounds, and the present invention provides the compounds of the formulae (IV) and (VIII) wherein $R^6$ is 4-piperidyl which may be substituted, which are industrially favored as an intermediate for the synthesis of the novel compound (I) being useful as a pharmaceutical.

The compound of the formula (V) wherein $R^4$ is hydrogen can also produced, for example, according to the following reaction scheme.

The reaction (XXX)→(XL) can be conducted under the same conditions as those of the reaction (XXXI)→(VII). The compounds (V') can be produced by reacting the compounds (XL) and (IV) or (VIII) under the same conditions as those of the reaction of the compounds (III) and (IV) or (VII) and (VIII).

In the above-mentioned processes for producing the compound (I) and its intermediates, the compounds to be used in the reactions may be employed in the form of salts, such as inorganic acid salts being exemplified by hydrochloride, hydrobromide, sulfate, nitrate, phosphate, etc., organic acid salts being exemplified by acetate, tartarate, citrate, fumarate, maleate, toluenesulfonate, methanesulfonate, etc., metal salts being exemplified by sodium salt, potassium salt, calcium salt, aluminum salt, etc., and salts with bases being exemplified by triethylamine salt, guanidine salt, ammonium salt, hydrazine salt, quinine salt, cinchonine salt, etc., so long as they do not interfere with such reactions.

The following Examples, Experiment Examples and Preparation Examples are further illustrative but by no means limitative of this invention.

EXAMPLE 1

In an aqueous solution (200 ml) of 1.4 g of sodium carbonate is dissolved 2.9 g of S-(o-nitrophenyl)-L-cysteine, and 3.5 g of N-ethoxycarbonylphthalimide is added to the solution under stirring. After the mixture is stirred at room temperature for 5 hours, the insoluble matter is removed by filtration, and the filtrate is made weakly acid with concentrated hydrochloric acid. The crystals which separate out are recovered by filtration, and recrystallized from 30 ml of ethanol to give 3.6 g of 3-(o-nitrophenyl)thio-2(R)-phthalimidopropionic acid as pale yellow needles, melting at 220°-222° C.

Elemental analysis, for $C_{17}H_{12}N_2O_6S$. Calcd.: C, 54.84; H, 3.25; N, 7.53. Found : C, 54.46; H, 3.26; N, 7.46.

$[\alpha]_D^{24} - 79°$ (c=0.9, in methanol).

EXAMPLE 2

In 300 ml of methanol is placed 10 g of 3-(o-nitrophenyl)thio-2(R)-phthalimidopropionic acid, which is catalytically reduced at ordinary temperature under atmospheric pressure, using 5% palladium-carbon as a catalyst. After the calculated amount of hydrogen is absorbed, the catalyst is removed, and the methanol is evaporated off under reduced pressure. Ether and petroleum ether are added to the residue, and the deposited yellowish crystalline powder is collected by filtration to give 8.4 g of 3-(o-aminophenyl)thio-2(R)- phthalimidopropionic acid. This product (8.4 g) is dissolved in 50 ml of dimethylformamide, and 5.5 g of diethyl phosphorocyanidate is added dropwise to the solution under ice-cooling with stirring. After the addition is completed, the mixture is stirred for 5 minutes, and 2.28 g of triethylamine is further added dropwise under ice-cooling. The mixture is stirred under ice-cooling for 30 minutes and then at room temperature for 1 hour. Water (200 ml) is added to the reaction solution, and the mixture is allowed to stand overnight. The deposited solid is collected by filtration and dried. This product is purified by silica-gel column chromatography (dichloromethane:ethyl acetate=2:1) to give 5.4 g of 3(R)-phthalimido-2,3-dihydro-1,5(5H)-benzothiazepine-4-one as colorless prisms, melting at 202°–205° C.

Elemental analysis, for $C_{17}H_{12}N_2O_3S$. Calcd.: C, 62.95; H, 3.73; N, 8.64. Found : C, 63.15; H, 4.02; N, 8.49.

$[\alpha]_D^{21} -164°$ (c=0.9, in methanol)

EXAMPLE 3

To 50 ml of dimethylformamide is added 0.5 g of sodium hydride (60% in oil), and the mixture is stirred under ice-cooling. 3(R)-Phthalimido-2,3-dihydro-1,5(5H)-benzothiazepine-4-one (4 g) as obtained in Example 2 is added to the mixture under ice-cooling, followed by stirring for 5 minutes. Tert-Butyl chloroacetate (2 g) is further added to the mixture under ice-cooling, and after stirring under ice-cooling for 15 mintues, ice-cold water (200 ml) is added to the reaction solution. The deposited crystals are collected by filtration, dried and purified by silica-gel column chromatography (hexane: ethyl acetate=3:1) to give 4 g of tert-Butyl 4-oxo-3(R)-phthalimido-2,3,4,5-tetrahydro-1,5-benzothiazepine-5-acetate as colorless crystals. Recrystallization from ethyl ether of a part of the compound yields colorless prisms, melting at 181°–184° C.

Elemental analysis, for $C_{23}H_{22}N_2O_5S$. Calcd.: C, 63.01; H, 5.06; N, 6.39. Found : C, 62.95; H, 5.10; N, 6.34.

$[\alpha]_D^{20} -156°$ (c=0.9, in chloroform).

EXAMPLE 4

To 100 ml of ethanol are added 4 g of tert-butyl 4-oxo-3(R)-phthalimido-2,3,4,5-tetrahydro-1,5-benzothiazepine-5-acetate as obtained in Example 3 and 1.4 g of hydrazine hydrate, and the mixture is heated under reflux for 1 hour with stirring. The reaction solution is concentrated under reduced pressure, and 300 ml of ethyl acetate and 100 ml of water are added to the residue, followed by shaking thoroughly. The ethyl acetate layer is washed with dilute aqueous sodium hydroxide solution and water, succesively, then dried over anhydrous magnesium sulfate and concentrated under reduced pressure. The resulting oily material is crystallized from a mixture of ether and petroleum ether to give 2 g of tert-butyl 3(R)-amino-4-oxo-2,3,4,5-tetrahydro-1,5-benzothiazepine-5-acetate as colorless prisms, melting at 86°–89° C.

Elemental analysis, for $C_{15}H_{20}N_2O_3S$. Calcd.: C, 58.42; H, 6.54; N, 9.08. Found : C, 58.73; H, 6.48; N, 9.13.

$[\alpha]_D^{20} -238°$ (c=1, in methanol).

EXAMPLES 5 to 9

Using substituted o-nitroaniline derivatives as a starting material, the reaction is carried out in the same manner as in the synthesis of the unsubstituted derivatives (R=H) to give the compounds as shown in Table 1.

TABLE 1

| Example No. | R | Config. *1 | Melting point, °C. | $[\alpha]_D$ in 1N hydrochloric acid |
|---|---|---|---|---|
| 5 | 4-CH₃ | R | 156–158 | +44° |
| 6 | 4-OCH₃ | R | 166–168 | +24° |
| 7 | 4,5-(CH₂)₃— | R | 157–158 | +33° |
| 8 | 4-Cl | R | 169–171 | +46° |
| 9 | 4-CF₃ | R | 181–183 | +53° |

EXAMPLES 10 to 13

In the same manner as Example 1, the S-(2-nitrophenyl)-L-cysteine derivatives as obtained in Examples 5 to 8 are reacted with N-ethoxycarbonylphthalimide to give the compounds as shown in Table 2.

TABLE 2

| Example No. | R | Config. *1 | Melting point, °C. | $[\alpha]_D$ in methanol |
|---|---|---|---|---|
| 10 | 4-CH₃ | R | Used in the subsequent reaction without being purified. | |
| 11 | 4-OCH₃ | R | 157–159 | −120° |
| 12 | 4,5-(CH₂)₃— | R | 219–222 | −149° |
| 13 | 4-Cl | R | 183–185 | −116° |

EXAMPLES 14 to 17

The phthalimide derivatives as obtained in Examples 10 to 13 are subejcted to a reaction similar to the reaction described in Example 2 to give the compounds as shown in Table 3.

TABLE 3

| Example No. | R | Config. *1 | Melting point, °C. | $[\alpha]_D$ |
|---|---|---|---|---|
| 14 | 7-CH₃ | R | 222–225 | −180° (in methanol) |
| 15 | 7-OCH₃ | R | 255–258 | −34° (in chloroform) |
| 16 | 7,8-(CH₂)₃— | R | 240–243 | −136° (in methanol) |

TABLE 3-continued

[Structure: benzothiazepine with phthalimide group, R substituent at position 6/7]

| Example No. | R | Config. *1 | Melting point, °C. | [α]_D |
|---|---|---|---|---|
| 17 | 7-Cl | R | 256-258 | -169° (in methanol) |

EXAMPLES 18 to 21

The phthalimidobenzothiazepine derivatives as obtained in Examples 14 to 17 are subjected to a rection similar to the reaction described in Example 3 to give the compounds as shown in Table 4.

TABLE 4

[Structure with CH₂COOC(CH₃)₃ on N]

| Example No. | R | Config. *1 | Melting point, °C. | [α]_D in methanol |
|---|---|---|---|---|
| 18 | 7-CH₃ | R | 140-143 | -151° |
| 19 | 7-OCH₃ | R | 155-157 | -139° |
| 20 | 7,8-(CH₂)₃— | R | 195-198 | -114° |
| 21 | 7-Cl | R | 182-184 | -148° |

EXAMPLES 22 to 25

The tert-butyl phthalimidobenzothiazepine acetate derivatives as obtained in Examples 18 to 21 are subjected to a reaction similar to the reaction described in Example 4 to give the compounds as shown in Table 5.

TABLE 5

[Structure with NH₂ and CH₂COOC(CH₃)₃]

| Example No. | R | Config. *1 | Melting point, °C. | [α]_D (in methanol) |
|---|---|---|---|---|
| 22 | 7-CH₃ | R | 159-160 (oxalate) | -146° |
| 23 | 7-OCH₃ | R | 175-178 (hydrochloride) | -147° |
| 24 | 7,8-(CH₂)₃— | R | Used in the subsequent reaction without being purified. | |
| 25 | 7-Cl | R | 158-160 (oxalate) | -102° |

EXAMPLE 26

To 67 ml of 0.25N aqueous sodium hydroxide solution is added 5.3 g of S-(2-nitro-4-trifluoromethyl-phenyl)-L-cysteine as obtained in Example 9, and after stirring at room temperature for 30 minutes, 2.7 ml of benzyloxycarbonyl chloride and 19 ml of 1N aqueous sodium hydroxide solution are simultaneously added dropwise to the mixture under ice-cooling over the period of 30 minutes, followed by stirring at room temperature for 2.5 hours. The reaction solution is extracted with ethyl ether, and the aqueous solution layer is made weakly acidified with 1N hydrochloric acid, and extracted with ethyl acetate. The extract is dried over anhydrous magnesium sulfate, and concentrated under reduced pressure, and ethyl ether is added to the resulting residue to deposit 5.5 g of S-(2-nitro-4-trifluoromethyl-phenyl)-N-benzyloxycarbonyl-L-cysteine as pale yellow crystals, melting at 150°-153° C.

$[α]_D + 20°$ (in methanol).

Elemental analysis, for $C_{18}H_{15}F_3N_2O_6S$. Calcd.: C, 48.65; H, 3.40; N, 6.30. Found : C, 48.68; H, 3.41; N, 6.27.

EXAMPLE 27

To a mixture of 50 ml of acetic acid and 50 ml of water are added 4.3 g of S-(2-nitro-4-trifluoromethyl-phenyl)-N-benzyloxycarbonyl-L-cysteine as obtained in Example 26 and 4 g of powdered zinc, followed by stirring at room temperature for 50 minutes. Water (150 ml) and 150 ml of ethyl acetate are added to the mixture, and the insoluble matter is filtered off. The aqueous layer is extracted further twice with 100 ml of ethyl acetate, and the ethyl acetate layers are combined, washed with water, dried over anhydrous magnesium sulfate and concentrated under reduced pressure. The residue is dissolved in 50 ml of ethyl ether, and 5 ml of hydrogen chloride-ethyl acetate solution (5N) is added to the solution to give 3.4 g of S-(2-amino-4-trifluoromethylphenyl)-N-benzyloxycarbonyl-L-cysteine hydrochloride as yellowish powder. This product is dissolved in 30 ml of dimethylformamide, and a solution of 0.78 g of triethylamine in 5 ml of dimethylformamide is added dropwise to the solution under ice-cooling with stirring over the period of 10 minutes, followed by adding dropwise a solution of 1.83 g of diethyl phosphorocyanidate in 5 ml of dimethylformamide over the period of 5 minutes and adding a solution of 0.78 g of triethylamine in 5 ml of dimethylformamide. The reaction solution is stirred under ice-cooling for 30 minutes and then at room temperature for 2.5 hours, followed by adding 200 ml of water. The mixture is extracted with ethyl acetate, and the extract is dried over anhydrous magnesium sulfate and concentrated under reduced pressure. The resulting oily material is purified by silica-gel column chromatography (hexane:ethyl acetate=4:1 to 2:1) to give 1.3 g of 3(R)-benzyloxycarbonylamino-7-trifluoromethyl-2,3-dihydro-1,5(5H)-benzothiazepine-4-one as colorless crystalline powder, melting at 120°-123° C.

$[α]_D - 161°$ (in methanol).

Elemental analysis, for $C_{18}H_{15}F_3N_2O_3S$. Calcd.: C, 54.54; H, 3.81; N, 7.07. Found : C, 54.79; H, 3.90; N, 7.09.

EXAMPLE 28

In 20 ml of dimethylformamide is dissolved 1.1 g of 3(R)-benzyloxycarbonylamino-7-trifluoromethyl-2,3-dihydro-1,5(5H)-benzothiazepine-4-one as obtained in Example 27, and 0.46 g of tert-butyl chloroacetate, 0.42 g of potassium carbonate and 0.1 g of potassium iodide are added to the solution, followed by stirring at room temperature for 4.5 hours. Water (100 ml) is added to the reaction solution, and the mixture is extracted with 100 ml of ethyl acetate. The extract is washed with 0.1N hydrochloric acid, aqueous sodium hydrogen-carbonate solution and water successively, dried over anhydrous magnesium sulfate and concentrated under reduced pressure to give 1.4 g of tert-butyl 3(R)-benzyloxycarbonylamino-4-oxo-7-trifluoromethyl-2,3,4,5-tetrahydro-1,5-benzothiazepine-5-acetate as a colorless viscous material.

IR$_{max}^{nujol}$ cm$^{-1}$: 1680 (amide), 1710 (urethane), 1740 (ester).

*IR: (stands for infrared absorption spectrum; the same shall apply thereafter).

EXAMPLE 29

In 5 ml of acetic acid is dissolved 1.4 g of tert-butyl 3(R)-benzyloxycarbonylamino-4-oxo-7-trifluoromethyl-2,3,4,5-tetrahydro-1,5-benzothiazepine-5-acetate, and 10 ml of 30% hydrogen bromide-acetic acid solution is added to the solution, followed by allowing the mixture to stand at room temperature for 4 hours. Petroleum ether (100 ml) is added to the reaction solution, and the mixture is thoroughly shaken, followed by decanting the supernatant. After petroleum ether is again added to repeat the same procedure, the residue is dissolved in a mixture of ethyl acetate and benzene, and the mixture is concentrated to dryness under reduced pressure. Petroleum ether is added to the residue to give 0.75 g of 3(R)-amino-4-oxo-7-trifluoromethyl-2,3,4,5-tetrahydro-1,5-benzothiazepine-5-acetic acid hydrobromide as crystals.

Melting point; 176°–180° C.

Elemental analysis, for $C_{12}H_{11}F_3N_2O_3S \cdot HBr \cdot H_2O$. Calcd.: C, 34.38; H, 3.37; N, 6.68. Found : C, 34.40; H, 3.60; N, 6.66.

EXAMPLE 30

In 20 ml of methanol is dissolved 1 g of tert-butyl 3(R)-amino-4-oxo-2,3,4,5-tetrahydro-1,5-benzothiazepine-5-acetate as obtained in Example 4, and 0.32 g of potassium cyanide, 1.1 g of N-(4-formylbutyl)phthalimide and 0.3 g of acetic acid are added to the solution, followed by stirring at room temperature overnight. The reaction solution is concentrated to dryness under reduced pressure to yield as a crude product tert-butyl 3(R)-(1-cyano-5-phthalimidopentyl)amino-4-oxo-2,3,4,5-tetrahydro-1,5-benzothiazepine-5-acetate. This product, without being purified, is used as a starting compound for Example 31.

EXAMPLE 31

To 2 g of tert-butyl 3(R)-(1-cyano-5-phthalimidopentyl)amino-4-oxo-2,3,4,5-tetrahydro-1,5-benzothiazepine-5-acetate is added 20 ml of ethanolic hydrochloric acid (11N), and the mixture is stirred under ice-cooling for 6 hours, followed by allowing it to stand at room temperature overnight. The ethanol is evaporated off under reduced pressure, and 50 ml of ethanol and 10 g of Amberlyst 15 ion exchange resin are added to the residue, followed by refluxing with stirring for 7 hours. After cooling, the resin portion is treated with 5% pyridine-ethanol solution, and the ethanol portions are combined and concentrated under reduced pressure. The resulting oily material is dissolved in 300 ml of ethyl acetate, and the solution is washed with 0.1N hydrochloric acid and water successively. The ethyl acetate layer is dried over anhydrous magnesium sulfate and concentrated under reduced pressure, and the residue is purified by silica-gel column chromatography (hexane:acetone=2:1) to give 0.9 g of ethyl 3(R)-(1-ethoxycarbonyl-5-phthalimidopentyl)amino-4-oxo-2,3,4,5-tetrahydro-1,5-benzothiazepine-5-acetate as a colorless oily material.

IR $\nu_{max}^{neat}$ cm$^{-1}$: 1770, 1740, 1720, 1710(phthalimide and ester) 1670(amide).

Mass spectrum (m/e): 567 (M+)

EXAMPLE 32

In 25 ml of dimethylformamide is dissolved 6.48 g of 3(R)-phthalimido-2,3-dihydro-1,5(5H)-benzothiazepine-4-one as obtained in Example 2, and 6.27 g of tert-butyl 2-bromopropionate, 5.5 g of potassium carbonate and 0.5 g of potassium iodide are added to the solution, followed by stirring at room temperature overnight. Water (200 ml) is added to the reaction solution, and the mixture is extracted with 300 ml of ethyl acetate. The extract is washed with 200 ml of 0.5N hydrochloric acid and 100 ml of saturated aqueous sodium hydrogencarbonate solution successively, then dried over anhydrous magnesium sulfate and concentrated under reduced pressure. The resulting oily material is purified by silica-gel column chromatography (hexane:ethyl acetate=3:1 to 2:1) to give 7.8 g of tert-butyl 3(R)-phthalimido-4-oxo-2,3,4,5-tetrahydro-1,5-benzothiazepine-5-α-methylacetate as a colorless powder.

IR $\nu_{max}^{neat}$ cm$^{-1}$: 1770, 1730, 1720, 1680(C=O).

Elemental analysis, for $C_{24}H_{24}N_2O_5S \cdot \frac{1}{2}H_2O$. Calcd.: C, 62.46; H, 5.46; N, 6.07. Found : C, 62.62; H, 5.14; N, 6.13.

EXAMPLE 33

In the same manner as Example 4, 7.6 g of tert-butyl 3(R)-phthalimido-4-oxo-2,3,4,5-tetrahydro-1,5-benzothiazepine5-α-methylacetate as obtained in Example 32 is treated with hydrazine hydrate to give 5.4 g of tert-butyl 3(R)-amino-4-oxo-2,3,4,5-tetrahydro-1,5-benzothiazepine-5-α-methylacetate as a pale yellow oil.

IR $\nu_{max}^{neat}$ cm$^{-1}$: 1735, 1670(C=O).

$[\alpha]_D$ −223° (c=0.5, in methanol).

Mass spectrum (m/e): 322 (M+)

EXAMPLE 34

In 20 ml of dimethylformamide is dissolved 3.08 g of tert-butyl 3(R)-amino-4-oxo-2,3,4,5-tetrahydro-1,5-benzothiazepine-5-acetate as obtained in Example 4, and 7.36 g of ethyl 2-bromo-6-phthalimidohexanoate, 2.76 g of potassium carbonate and 1.66 g of potassium iodide are added to the solution, followed by stirring at room temperature overnight. Furthermore, 3.68 g of the bromo ester and 1.38 g of potassium carbonate are additionally added to the mixture, followed by stirring for 3 days. Water (100 ml) and 300 ml of ethyl acetate are added to the reaction solution, followed by extraction. The extract is washed with water and concentrated under reduced pressure. Oxalic acid (5 g) and 30 ml of ethyl acetate are added to the resulting residue to bring into a solution, and 120 ml of petroleum ether is added to the solution, followed by shaking thoroughly. After allowing the mixture to stand, the supernatant is decanted, and the same procedure is repeated four times with the residue, followed by adding to the residue 100 ml of saturated aqueous sodium hydrogen-carbonate solution and then 300 ml of ethyl acetate, followed by extraction. The extract is dried over anhydrous magnesium sulfate and concentrated under reduced pressure. The resulting oily material is purified by silica-gel column chromatography (hexane:acetone=4:1) to give as the first fraction 1.75 g of tert-butyl 3(R)-[1(R)-ethoxycarbonyl-5-phthalimidopentyl]-amino-4-oxo-2,3,4,5-tetrahydro-1,5-benzothiazepine-5-acetate as an oily material.

IR $\nu_{max}^{neat}$ cm$^{-1}$: 3330(NH), 1780, 1740, 1720, 1680(C=O)

Mass spectrum (m/e): 595 (M+).

From the second fraction is obtained 2.5 g of tertbutyl 3(R)-[1(S)-ethoxycarbonyl-5-phthalimidopentyl]amino-4-oxo-2,3,4,5-tetrahydro-1,5-benzothiazepine-5-acetate as a colorless oil.

IR $\nu_{max}^{neat}$: 1770, 1740, 1720, 1680(C=O)

Mass spectrum (m/e): 595 (M+).

$[\alpha]_D$ −119° (c=0.3, in methanol).

EXAMPLE 35

In 5 ml of 5N hydrogen chloride-ethyl acetate solution is dissolved 0.2 g of tert-butyl 3(R)-[1(S)-ethoxycarbonyl-5-phthalimidopentyl]amino-4-oxo-2,3,4,5-tetrehydro-1,5-benzothiazepine-5-acetate as obtained in Example 34, and the solution is allowed to stand at room temperature for 3 hours. Ethyl ether(50 ml) is added to the reaction solution, and the deposited precipitate is washed with 100 ml of ethyl ether to give 0.13 g of 3(R)-[1(S)-ethoxycarbonyl-5-phthalimidopentyl]amino-4-oxo-2,3,4,5-tetrahydro-1,5-benzothiazepine-5-acetic acid.hydrochloride as a colorless powder.

Elemental analysis, for $C_{27}H_{29}N_3O_7S \cdot HCl \cdot \frac{1}{2}H_2O$. Calcd.: C, 55.42; H, 5.34; N, 7.18. Found : C, 55.09; H, 5.12; N, 7.15.

$[\alpha]_D$ −114° (c=0.5, in methanol).

EXAMPLE 36

In 20 ml of ethanol is dissolved 1.6 g of tert-butyl 3(R)-[1(R)-ethoxycarbonyl-5-phthalimidopentyl]amino-4-oxo-2,3,4,5-tetrahydro-1,5-benzothiazepine-5-acetate as obtained in Example 34, and 0.8 g of 85% hydrazine hydrate is added to the solution, followed by allowing the mixture to stand at room temperature overnight. Ethyl acetate (200 ml) and 200 ml of water are added to the reaction solution, followed by extraction. The ethyl acetate portion is washed with 0.1N aqueous sodium hydroxide solution and water successively to yield an ethyl acetate solution of tert-butyl 3(R)-[5-amino-1(R)-ethoxycarbonylpentyl]amino-4-oxo-2,3,4,5-tetrahydro-1,5-benzothiazepine-5-acetate. Sodium hydrogencarbonate (1.6 g) and 50 ml of water are added to this solution, and a solution of 0.9 g of di-tert-butyl dicarbonate in 5 ml of ethyl acetate is added dropwise to the mixture with stirring at room temperature. After stirring for 30 minutes, the ethyl acetate layer is separated and dried over anhydrous magnesium sulfate. After concentration under reduced pressure, the resulting oily material is purified by silica-gel column chromatography (hexane:acetone=4:1) to give 1.4 g of tert-butyl 3(R)-[5-tert-butoxycarbonylamino-1(R)-ethoxycarbonylpentyl]amino-4-oxo-2,3,4,5-tetrahydro-1,5-benzothiazepine-5-acetate as a colorless oily material.

IR $\nu_{max}^{neat}$ cm$^{-1}$: 3350(NH), 1740, 1710, 1680(C=O).

Mass spectrum (m/e): 565 (M+)

EXAMPLE 37

In the same manner as Example 36, 2.6 g of tert-butyl 3(R)-[1(S)-ethoxycarbonyl-5-phthalimidopentyl]amino-4-oxo-2,3,4,5-tetrahydro-1,5-benzbenzothiazepine-5-acetate as obtained in Example 34 is treated with hydrazine, and reacted with di-tert-butyl dicarbonate, followed by purification by silica-gel column chromatography to give 1.87 g of tert-butyl 3(R)-[5-tert-butoxycarbonylamino-1(S)-ethoxycarbonylpentyl]amino-4-oxo-2,3,4,5-tetrahydro-1,5-benzothiazepine-5-acetate as a colorless oily material.

IR $\nu_{max}^{neat}$ cm$^{-1}$: 3350(NH), 1740, 1710, 1670(C=O).

Mass spectrum (m/e): 565 (M+).

$[\alpha]_D$ −136° (C=0.8 in methanol).

EXAMPLE 38

In a mixture of 40 ml of methanol and 25 ml of 1N aqueous sodium hydroxide solution is dissolved 0.6 g of tert-butyl 3(R)-[5-tert-butoxycarbonylamino-1(S)-ethoxycarbonylpentyl]amino-4-oxo-2,3,4,5-tetrahydro-1,5-benzothiazepine-5-acetate as obtaiend in Example 37, and 10 ml of water is further added to the solution, followed by stirring at room temperature for 2 hours. The methanol is evaporated off under reduced pressure, and the residual solution is made weakly acidified with phosphoric acid and extracted with ethyl acetate. The extract is dried over anhydrous magnesium sulfate and concentrated under reduced pressure to give 0.37 g of tert-butyl 3(R)-[5-tert-butoxycarbonylamino-1(S)-carboxypentyl]amino-4-oxo-2,3,4,5-tetrahydro-1,5-benzothiazepine-5-acetate as a colorless viscous material. This product is treated with ethyl acetate to yield a colorless crystalline powder, melting at 134°–135° C.

Elemental analysis, for $C_{26}H_{39}N_3O_7S$. Cacld.: C, 58.08; H, 7.31; N, 7.82. Found : C, 58.11; H, 7.22; N, 7.73.

IR $\nu_{max}^{nujol}$ cm$^{-1}$: 3350(NH), 1730, 1700, 1680(C=O).

EXAMPLE 39

In 200 ml of acetonitrile dissolved 5 of tertbutyl 3(R)-amino-4-oxo-2,3,4,5-tetrahydro-1,5-benzothiazepine-5-acetate as obtained in Example 4 and 17.9 g of ethyl 2-bromo-6-phthalimidohexanoate, and the solution is refluxed for 45 hours. The acetonitrile is evaporated off under reduced pressure, and 200 ml of water and 300 ml of ethyl acetate are added to the residue, followed by extraction. The extract is washed with water, dried over anhydrous magnesium sulfate and concentrated under reduced pressure. The resulting oily material is purified by silica-gel column chromatography (hexane:acetone=4:1) to give as a colorless oily material 3.9 g of tert-butyl 3(R)-[1-(R)-ethoxycarbonyl-5-phthalimidopentyl]amino-4-oxo-2,3,4,5-tetrahydro-1,5-benzothiazepine-5-acetate and 4.1 g of tert-butyl 3(R)-[1(S)-ethoxycarbonyl-5-phthalimidopentyl]amino-4-oxo-2,3,4,5-tetrahydro-1,5-benzothiazepine-5-acetate, which are the same products as those obtained in Example 34.

EXAMPLES 40 to 42

Tert-Butyl 3(R)-amino-4-oxo-2,3,4,5-tetrahydro-1,5-benzothiazepine-5-acetate is reacted with the α-bromo esters shown in Table 6 in the same manner as Example 39 to give the following benzothiazepine derivatives.

TABLE 6

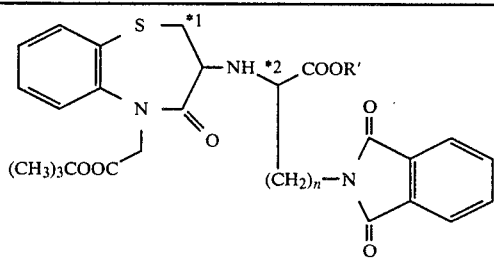

| Example No. | α-Bromo ester used | R' | n | Config. *1 | Config. *2 | IR $\nu_{max}^{neat}$ cm$^{-1}$ |
|---|---|---|---|---|---|---|
| 40 | (structure: N—(CH₂)₄CHCOO(CH₂)₃CH₃ with Br, phthalimide) | (CH₂)₃CH₃ | 4 | R | S | 3330, 1770. 1740, 1710 1675 |
|  |  |  |  | R | S | 3320, 1770, 1740, 1710, 1670 |
| 41 | (structure: N—(CH₂)₂CHCOOC₂H₅ with Br, phthalimide) | C₂H₅ | 2 | R | RS* | 3320, 1770, 1740, 1710, 1670 |
| 42 | (structure: N—(CH₂)₆CHCOOC₂H₅ with Br, phthalimide) | C₂H₅ | 6 | R | RS* | 3320, 1770, 1730, 1710, 1670 |

*mixture of diastereomers

EXAMPLES 43 to 45

The benzothiazepine derivatives as obtained in Examples 40 to 42 are treated with hydrogen chloride-ethyl acetate solution in the same manner as Example 35 to give the compounds as shown in Table 7.

TABLE 7

(structure of benzothiazepine derivative · HCl with COOR", (CH₂)ₙ—N-phthalimide, and HOOC-CH₂-N substituent)

| Example No. | R" | n | Config. *1 | Config. *2 | [α]_D in methanol |
|---|---|---|---|---|---|
| 43 | (CH₂)₃CH₃ | 4 | R | S | −106° (c = 0.6) |
| 44 | C₂H₅ | 2 | R | RS* | −133° (c = 0.5) |
| 45 | C₂H₅ | 6 | R | RS* | −105° (c = 0.5) |

*mixture of diastereomers

EXAMPLES 46 to 48

The benzothiazepine derivatives as otbained in Examples 40 to 42 are treated with hydrazine in the same manner as Example 36, followed by reaction with di-tert-butyl dicarbonate to give the compounds as shown in Table 3.

TABLE 8

(structure of benzothiazepine derivative with COOR''', (CH₂)ₙNHCOOC(CH₃)₃, and (CH₃)₃COOC-CH₂-N substituent)

| Example No. | R''' | n | Config. *1 | Config. *2 | IR $\nu_{max}^{neat}$ cm$^{-1}$ |
|---|---|---|---|---|---|
| 46 | (CH₂)₃CH₃ | 4 | R | S | 3350, 1730, 1710, 1670 |
| 47 | C₂H₅ | 2 | R | RS* | 3400, 1740, 1710, 1670 |
| 48 | C₂H₅ | 6 | R | RS* | 3350, 1730, 1710, 1670 |

*Mixture of diastereomers

EXAMPLE 49

In 20 ml of ethanol is dissolved 0.7 g of ethyl 3(R)-(1-ethoxycarbonyl-5-phthalimidopentyl)amino-4-oxo-2,3,4,5-tetrahydro-1,5-benzothiazepine-5-acetate as obtained in Example 31, and 0.3 g of 85% hydrazine hydrate is added to the solution. Hydrazine hydrate(0.3 g, 85 %)is additionally added to the reaction mixture 1 hour and 2 hours later, respectively, and the mixture is allowed to stand overnight. Ethanol is evporated off under reduced pressure, and 50 ml of water is added to the residue. Sodium chloride is added to the mixture to saturate the aqueous phase, followed by extraction with three 100 ml portions of ethyl acetate. The extract is wahsed with 50 ml of 0.1N aqueous sodium hydroxide solution and 100 ml of water successively, and dried over anhydrous magnesium sulfate. Hydrogen chloride ethyl acetate solution(5N, 0.5 ml) is added to the resulting ethyl acetate solution, and the mixture is concentrated under reduced pressure. Ethyl ether is added to the residue to give 0.13 g of ethyl 3(R)-(5-amino-1-ethoxycarbonylpentyl)amino-4-oxo-2,3,4,5-tetrahydro-1,5-benzothiazepine-5-acetate.dihydrochloride as a colorless powder.

Elemental analysis, for $C_{21}H_{31}N_3O_5S.2HCl.H_2O$. Calcd.: C, 47.73; H, 6.67; N, 7.95. Found: C, 47.81; H, 6.53; N, 7.83.

Mass spectrum (m/e): 437 (M+)

EXAMPLE 50

In a mixture of 30 ml of ethyl acetate and 10 ml of water is dissolved 50 mg of ethyl 3(R)-(5-amino-1-ethoxycarbonylpentyl)amino-4-oxo-2,3,4,5-tetrahydro-1,5-benzothiazepine-5-acetate.dihydrochloride as obtained in Example 49, and 0.15 ml of benzyloxycarbonyl chloride and 0.3 g of sodium hdyrogencarbonate are added to the solution, followed by stirring at room temperature for 2.5 hours. The ethyl acetate layer is washed with water, dired over anhydrous magnesium sulfate and concentrated under reduced pressure. The resulting residue is dissolved in a mixture of 20 ml of ethyl ether and 20 ml of petroleum ether, and 0.2 ml of 5N hydrogen chloride-ethyl acetate solution is added to the solution to give 55 mg of ethyl 3(R)-(5-benzyloxycarbonyl-amino-1-ethoxycarbonylpentyl)amino-4-oxo-2,3,4,5-tetrahydro-1,5-benzothiazepine-5-acetate.-hydrochloride as a colorless powder.

Mass spectrum (m/e): 571 (M+).

EXAMPLE 51

In a mixture of 3 ml of ethanol and 2 ml of 1N aqueous sodium hydroxide solution is dissolved 55 mg of ethyl 3(R)-(5-benzyloxycarbonylamino-1-ethoxycarbonylpentyl)amino-4-oxo-2,3,4,5-tetrahydro-1,5-benzothiazepine-5-acetate. hydrochloride as obtained in Example 50, and the solution is allowed to stand at room temperature for 1 hour. Water (50 ml) is added to the reaction solution, and after the mixture is extracted with 20 ml of ethyl ether, the aqueous layer is adjusted to pH 4 with 1N hydrochloric acid. Ammonium chloride is added to the solution until it becomes saturated, and the aqueous layer is extracted ten times with 20 ml of ethyl acetate. The extract is washed with a small amount of water, dried over anhydrous magnesium sulfate and concentrated under reduced pressure to give 40 mg of 3(R)-(5-benzyloxycarbonyl-amino-1-carboxypentyl-)amino-4-oxo-2,3,4,5-tetrahydro-1,5-benzothiazepine-5-acetic acid as a colorless powder.

Mass spectrum (m/e): 515 (M+).

EXAMPLE 52

In 1 ml of acetic acid is dissolved 40 mg of 3(R)-(5-benzyloxycarbonylamino-1-carboxypentyl)amino-4-oxo-2,3,4,5-tetrahydro-1,5-benzothiazepine-5-acetic acid as obtained in Example 51, and 1 ml of 30% hydrogen bromide-acetic acid solution is added to the solution, followed by stirring at room temperature for 1 hour. Ethyl ether (80 ml)and 20 ml of petroleum ether are added to the reaction solution, and the mixture is shaken and allowed to stand. The supernatant is decanted, and the precipitate is collected and dried to give 33 mg of 3(R)-(5-amino-1-carboxypentyl)amino-4-oxo-2,3,4,5-tetrahydro-1,5-benzothiazepine-5-acetic acid.-dihydrobromide as a colorless powder.

SIMS spectrum (m/e): 382 (MH+); addition of KI 420 (M+K)+.

EXAMPLES 53 and 54

The benzothiazepine derivatives as obtained in Examples 36 and 37 are treated with hydogen chloride in the same manner as Example 35 to give the compounds as shown in Table 9 as colorless crystals.

TABLE 9

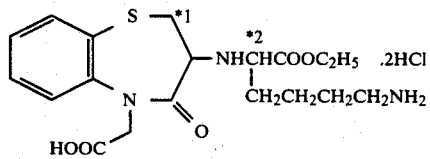

| Example No. | Config. *1 | *2 | $[\alpha]_D$ (in methanol) |
|---|---|---|---|
| 53 | R | R | −161° (c = 0.7) |
| 54 | R | S | −128° (c = 0.5) |

EXAMPLE 55

To 4 ml of 1N aqueous sodium hydroxide solution is added 0.2 g of 3(R)-[5-amino-1(S)-ethoxycarbonylpentyl]amino-4-oxo-2,3,4,5-tetrahydro-1,5-benzothiazepine-5-acetic acid, dihydrochloride as obtained in Example 54, and the mixture is stirred at room temperature for 1.5 hours. Acetic acid (1 ml) is added to the raction solution to make the solution weakly acidified, followed by purification by Amberlite XAD-2 column chromatography (methanol:water=3:7). The eluent is concentrated under reduced pressure, and the residue is lyophilized to give 0.1 g of 3(R)-[5-amino-1(S)-carboxypentyl]-amino-4-oxo-2,3,4,5-tetrahydro-1,5-benzothiazepine-5-acetic acid as a colorless powder.

Elemental analysis, for $C_{17}H_{23}N_3O_5S.H_2O$. Calcd.: C, 51.12; H, 6.31; N, 10.52. Found: C, 50.87; H, 5.83; N, 10.34.

$[\alpha]_D$ −149° (c=0.3, in 1N hydrochloric acid).

SIMS spectrum (m/e): 382 (MH+); addition of KI 420 (M+K)+.

EXAMPLE 56

In the same manner as Example 35, 0.32 g of tert-butyl 3(R)-[5-tert-butoxycarbonylamino-1(S)-carboxypentyl]amino-4-oxo-2,3,4,5-tetrahydro-1,5-benzothiazepine-5-acetate as obtained in Example 38 is treated with hydrogen chloride to give 0.26 g of 3(R)-[5-amino-1(S)-carboxypentyl]amino-4-oxo-2,3,4,5-tetrahydro-1,5-benzothiazepine-5-acetic acid.dihydrochloride as a colorless crystalline powder.

Elemental analysis, for $C_{17}H_{23}N_3O_5S.2HCl.CH_3COOC_2H_5$. Calcd.: C, 46.49; H, 6.13; N, 7.75. Found: C, 46.12; H, 6.16; N, 7.52.

This product (0.15 g) is dissolved in 2 ml of water, and 0.5 ml of 1N aqueous sodium hydroxide solution and then 0.5 ml of acetic acid are added to the solution, which is purified with Amberlite XAD-2 in the same manner as Example 55 to give 0.096 g of the free derivative which is the same compound as the one obtained in Example 55.

the corresponding α-keto ester derivatives, respectively.

TABLE 11

| Example No. | Starting compound | Keto ester derivative obtained bp (mmHg) |
|---|---|---|
| 61 | O⟨ ⟩—CH₂CH₂COOC₂H₅ | O⟨ ⟩—CH₂CH₂COCOOC₂H₅  115–125° C. (2) |
| 62 | S⟨ ⟩—CH₂CH₂COOC₂H₅ | S⟨ ⟩—CH₂CH₂COCOOC₂H₅  148–151° C. (3) |

EXAMPLES 57 to 59

The benzothiazepine derivatives as obtained in Examples 46 to 48 are treated with hydrogen chloride-ethyl acetate solution in the same manner as Example 35 to give the compounds as shown in Table 10.

TABLE 10

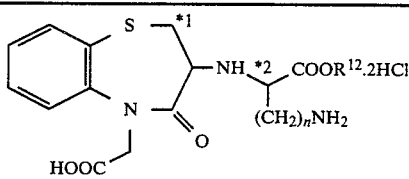

| Example No. | $R^{12}$ | n | Config. *1 | *2 | $[\alpha]_D$ in methanol |
|---|---|---|---|---|---|
| 57 | $(CH_2)_3CH_3$ | 4 | R | S | −123° (c = 0.4) |
| 58 | $C_2H_5$ | 2 | R | RS* | −144° (c = 0.4) |
| 59 | $C_2H_5$ | 6 | R | RS* | −118° (c = 0.4) |

*Mixture of diastereomers

EXAMPLE 60

In 10 ml of ethanol is dissolved 0.43 g of sodium, and 5 g of ethyl 3-(1-benzyloxycarbonyl-4-piperidyl)propionate and 2.75 g of diethyl oxalate are added to the solution. The solvent is evaporated off under reduced pressure, while heating on a warm-water bath at 60° to 70° C. for 45 minutes. After cooling, the resulting brown viscous material is treated with 200 ml of water, and the mixture is made weakly acidified with concentrated hydrochloric acid. The mixture is extracted with 300 ml of ethyl acetate, and the extract is dried over anhydrous magnesium sulfate, and concentrated under reduced pressure. Ten (10) % aqueous dimethylformamide (50 ml) and 0.73 g of lithium chloride are added to the resulting yellow oily material, followed by stirring at 100° C. for 30 minutes, at 120° to 130° C. for 30 minutes and then at 140° C. for 45 minutes. After cooling, 300 ml of water is added to the reaction solution, and the mixture is extracted with 300 ml of ethyl acetate. The extract is washed with water, dried over anhydrous magnesium sulfate, and concentrated under reduced pressure to give 4.5 g of ethyl 4-(1-benzyloxycarbonyl-4-piperidyl)-2-oxobutyrate as a pale brown oil.

IR $\nu_{max}^{neat}$cm$^{-1}$: 1730, 1700(C=O).

Mass spectrum (m/e): 347 (M+).

EXAMPLES 61, 62

Using the ethyl propionate derivatives as shown in Table 11 as starting compound, the reaction corresponding to the one of Example 60 is carried out to give

EXAMPLE 63

In 50 ml of ethanol is dissolved 2 g of tert-butyl 3(R)-amino-4-oxo-2,3,4,5-tetrahydro-1,5-benzothiazepine-5-acetate, and 0.43 g of acetic acid, 4.5 g of ethyl 4-(1-benzyloxycarbonyl-4-piperidyl)-2-oxobutyrate as obtained in Example 60 and 10 g of Molecular sieve 3A are added to the solution. The mixture is stirred at room temperature for 1 hour, and a solution of 0.4 g of sodium cyanoborohydride in 30 ml of ethanol is added dropwise to the mixture at room temperature with stirring over the period of 2.5 hours. A solution of 0.5 g of sodium cyanoborohydride in 20 ml of ethanol is further added dropwise to the mixture over the period of 3 hours. The reaction solution is allowed to stand overnight, and concentrated under reduced pressure, and 300 ml of water and 300 ml of ethyl acetate are added to the residue, followed by shaking. The insoluble matter is filtered off, and the ethyl acetate layer is dried over anhydrous magnesium sulfate and concentrated under reduced pressure. Ethyl ether (50 ml) is added to the residue, to which a solution of 1 g of oxalic acid in 50 ml of ethyl ether is added. Petroleum ether (200 ml) is added, followed by shaking thoroughly, and the mixture is allowed to stand. The supernatant is decanted, and 100 ml of petroleum ether is again added to the precipitate portion, which is then shaken. The petroleum ether layer is removed by decantation, and 50 ml of water and 200 ml of ethyl acetate are added to the precipitate portion, followed by adding excess sodium hydrogencarbonate to the mixture with stirring to effect neutralization. The ethyl acetate layer is washed with water, dried over anhydrous magnesium sulfate and concentrated under reduced pressure to give an oily material. This product is separated and purified by silica-gel column chromatography (hexane:ethyl acetate=2:1 to 4:3) to give as the first fraction 0.6 g of tert-butyl 3(R)-[3-(1-benzyloxycarbonyl-4-piperidyl)-1(R)-ethoxycarbonylpropyl]amino-4-oxo-2,3,4,5-tetrahydro-1,5-benzothiazepine-5-acetate as a colorless oily material.

IR $\nu_{max}^{neat}$cm$^{-1}$: 3320(NH), 1740, 1700, 1680(C=O).

Mass spectrum (m/e): 639 (M+).

From the subsequent fracion, 1.3 g of tert-butyl 3(R)[3-(1-benzyloxycarbonyl-4-piperidyl)-1(S)-ethoxycarbonylpropyl]-amino-4-oxo-2,3,4,5-tetrahydro-1,5-benzothiazepine-5-acetate is obtained as a colorless oily material.

IR $\nu_{max}^{neat}$cm$^{-1}$: 3320(NH), 1740, 1700, 1690, 1670(C=O).

Mass spectrum (m/e): 639 (M+).

EXAMPLES 64, 65

The α-keto esters as obtained in Examples 61 and 62 are reacted with tert-butyl 3(R)-amino-4-oxo-2,3,4,5-tetrahydro-1,5-benzothiazepine-5-acetate in the same manner as Example 63 to give the compounds shown in Table 12 as an oily material.

TABLE 12

| Example No. | R | Config. *1 *2 | [α]$_D$ in methanol | Mass spectrum (m/e) M+ |
|---|---|---|---|---|
| 64 | ⟨O⟩ | R R<br>R S | —<br>−137° (c = 0.6) | 506<br>506 |
| 65 | ⟨S⟩ | R R<br>R S | −96° (c = 0.3)<br>−82° (c = 0.6) | 522<br>522 |

EXAMPLE 66

In 20 ml of 5N hydrogen chloride-ethyl acetate solution is dissolved 0.3 g of tert-butyl 3(R)-[3-(1-benzyloxycarbonyl-4-piperidyl)-1(S)-ethoxycarbonylpropyl]amino-4-oxo-2,3,4,5-tetrahydro-1,5-benzothiazepine-5-acetate as obtained in Example 63, and the solution is allowed to stand at room temperature for 3 hours. Petroleum ether (200 ml) is added to the reaction solution to deposit 3(R)-[3-(1-benzyloxycarbonyl-4-piperidyl)-1(S)-ethoxycarbonylpropyl]amino-4-oxo-2,3,4,5-tetrahydro-1,5-benzothiazepine-5-acetic acid.hydrochloride. The supernantant liquid is decanted, followed by drying to give 0.22 g of a colorless powder.

Elemental analysis, for $C_{30}H_{37}N_3O_7S.HCl.H_2O$. Calcd.: C, 56.46; H, 6.32; N, 6.58. Found: C, 56.29; H, 6.31; N, 6.57.

[α]$_D$ −91° (c=0.6, in methanol).

EXAMPLES 67 to 70

The benzothiazepine derivatives as obtained in Examples 64 and 65 are treated with hydrogen chloride in the same manner as Example 66 to give the compounds shown in Table 13.

TABLE 13

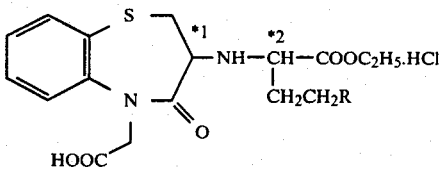

| Example No. | R | Config. *1 *2 | [α]$_D$ (c = 0.6) in methanol |
|---|---|---|---|
| 67 | ⟨O⟩ | R R | −151° |
| 68 | ⟨O⟩ | R S | −119° |
| 69 | ⟨S⟩ | R R | −144° |
| 70 | ⟨S⟩ | R S | −108° |

EXAMPLE 71

In 2 ml of acetic acid is dissolved 0.6 g of tert-butyl 3(R)-[3-(1-benzyloxycarbonyl-4-piperidyl)-1(R)-ethoxycarbonylpropyl]amino-4-oxo-2,3,4,5-tetrahydro-1,5-benzothiazepine-5-acetate as obtained in Example 63, and 2 ml of 30% hydrogen bromide-acetic acid solution is added to the solution, followed by allowing the mixture to stand at room temperature for 1 hour. Ethyl ether (150 ml) is added to the reaction solution, and the mixture is allowed to stand. Then, the supernatant is decanted, and the precipitate is washed with ethyl ether, and dried to give 0.5 g of 3(R)-[1(R)-ethoxycarbonyl-3-(4-piperidyl)propyl]amino-4-oxo-2,3,4,5-tetrahydro-1,5-benzothiazepine-5-acetic acid.dihydrobromide as a colorless powder.

Elemental analysis, for $C_{22}H_{31}N_3O_5S.2HBr.H_2O$. Calcd.: C, 41.98; H, 5.60; N, 6.68. Found: C, 41.43; H, 5.39; N, 6.30.

[α]$_D^{22}$ −106° (c=0.6, in methanol).

EXAMPLE 72

In the same manner as Example 71, 0.4 g of tert-butyl 3(R)-[3-(1-benzyloxycarbonyl-4-piperidyl)-1(S)-ethoxycarbonylpropyl]amino-4-oxo-2,3,4,5-tetrahydro-1,5-benzothiazepine-5-acetate as obtained in Example 63 is treated with hydrogen bromide to give 0.35 g of 3(R)-[1(S)-ethoxycarbonyl-3-(4piperidyl)propyl]amino-4-oxo-2,3,4,5-tetrahydro-1,5-benzothiazepine-5-acetic acid.dihydrobromide as a colorless powder.

Elemental analysis, for $C_{22}H_{31}N_3O_5S.2HBr.H_2O$. Calcd.: C, 40.81; H, 5.76; N, 6.49. Found: C, 40.47; H, 5.32; N, 6.28.

[α]$_D$ −86° (c=0.6, in methanol).

EXAMPLE 73

In 4 ml of 0.1N aqueous sodium hydroxide solution is dissolved 0.15 g of 3(R)-[1(S)-ethoxycarbonyl-3-(4-piperidyl)propyl]amino-4-oxo-2,3,4,5-tetrahydro-1,5-benzothiazepine-5-acetic acid.dihydrobromide as obtained in Example 72, and the solution is allowed to stand at room temperature for 2 hours. The solution is made weakly acidified with 1 ml of acetic acid, and purified by Amberlite XAD-2 column chromatography (methanol:water=1:1). The eluate is concentrated under reduced pressure, and the residue is lyophilized to give 0.06 g of 3(R)-[1(S)-carboxy-3-(4-piperidyl)propyl]amino-4-oxo-2,3,4,5-tetrahydro-1,5-benzothiazepine-5-acetic acid as a colorless powder.

Elemental analysis, for $C_{20}H_{27}N_3O_5S.H_2O$. Calcd.: C, 54.65; H, 6.65; N, 9.56. Found: C, 54.05; H, 6.17; N, 9.21.

Mass spectrum (m/e): 422 (MH+): addition of KI, 460 (M+K)+.

$[\alpha]_D - 128°$ (c=0.1, in methanol-water).

EXAMPLES 74, 75

The benzothiazepine derivatives as obtained in Examples 68 and 70 are hydrolyzed with 1N aqueous sodium hydroxide solution in the same manner as Example 73, followed by purification by Amberlite XAD-2 column chromatography to give the compounds as shown in Table 14 as a colorless powder.

TABLE 14

Structure: benzothiazepine with substituents, –NHCHCOOH, CH$_2$CH$_2$–R, with stereocenters *1 and *2, and HOOC– group on N.

| Example No. | R | Config. *1 | *2 | $[\alpha]_D$ |
|---|---|---|---|---|
| 74 | (tetrahydropyranyl, O) | R | S | −140° (c = 0.6) in methanol |
| 75 | (tetrahydrothiopyranyl, S) | R | S | −106° (c = 0.2) in methanol + 1N HCl |

EXAMPLE 76

In 10 ml of ethanol is dissolved 0.25 g of 3(R)-[1(S)-ethoxycarbonyl-3-(4-piperidyl)propyl]amino-4-oxo-2,3,4,5-tetrahydro-1,5-benzothiazepine-5-acetic acid.-dihydrobromide as obtained in Example 72, and 67 mg of sodium acetate and 52 mg of benzaldehyde are added to the solution. A solution of 31 mg of sodium cyanoborohydride in 10 ml of ethanol is added dropwise to the mixture over the period of 30 minutes. The ethanol is evaporated off under reduced pressure and 50 ml of water is added to the residue. The mixture is made weakly acidified with acetic acid, and extracted three times with 50 ml of dichloromethane. The extract is washed with a small amount of water and concentrated under reduced pressure. The resulting oily material is dissolved in 1 ml of dichloromethane, and 0.5 ml of 5N hydrogen chloride-acetic acid solution is added to the solution. The deposited colorless powder is washed with ethyl ether, and dried to give 157 mg of 3(R)-[3-(1-benzyl-4-piperidyl)-1(S)-ethoxycarbonylpropyl]amino-4-oxo-2,3,4,5-tetrahydro-1,5-benzothiazepine-5-acetic acid.dihydrochloride.

Elemental analysis, for $C_{29}H_{37}N_3O_5S.2HCl.H_2O$. Calcd.: C, 55.23; H, 6.55; N, 6.66. Found: C, 54.92; H, 6.74; N, 6.14.

$[\alpha]_D - 76°$ (c=0.4, in methanol).

EXAMPLE 77

In 5 ml of ethyl acetate is dissolved 0.1 g of 3(R)-[1(S)-ethoxycarbonyl-3-(4-piperidyl)propyl]amino-4-oxo-2,3,4,5-tetrahydro-1,5-benzothiazepine-5-acetic acid.dihydrobromide as obtained in Example 72, and 66.2 mg of triethylamine is added to the solution. A solution of 23 mg of benzoyl chloride in 2 ml of ethyl acetate is added dropwise to the mixture under ice-cooling with stirring over the period of 2 minutes. The reaction solution is stirred at room temperature for 50 minutes, and 20 ml of petroleum ether is added, followed by extracting 6 times with 20 ml of saturated aqueous sodium hydrogencarbonate solution. The aqueous layer is made weekly acidified with hydrochloric acid, and extracted three times with 30 ml of dichloromethane. The extract is dried over anhydrous magnesium sulfate, and concentrated under reduced pressure. The resulting oily material is dissolved in 1 ml of ethyl acetate, and 0.3 ml of 5N hydrogen chloride-ethyl acetate solution is added to the solution, which is then diluted with ethyl ether. The deposited precipitate is washed with ethyl ether and dried to give 28 mg of 3(R)-[3-(1-benzoyl-4-piperidyl)-1(S)-ethoxycarbonylpropyl]-amino-4-oxo-2,3,4,5-tetrahydro-1,5-benzothiazepine-5-acetic acid.hydrochloride as a colorless powder.

Elemental analysis, for $C_{29}H_{35}N_3O_6S.HCl.H_2O$. Calcd.: C, 57.27; H, 6.30; N, 6.91. Found: C, 56.98; H, 5.99; N, 7.01.

EXAMPLE 78

In the same manner as Example 77, 0.12 g of 3(R)-[1(S)-ethoxycarbonyl-3-(4-piperidyl)propyl]amino-4-oxo-2,3,4,5-tetrahydro-1,5-benzothiazepine-5-acetic acid.dihydrobromide as obtained in Example 72 is reacted with acetyl chloride to give 77 mg of 3(R)-[3-(1-acetyl-4-piperidyl)-1(S)-ethoxycarbonylpropyl]amino-4-oxo-2,3,4,5-tetrahydro-1,5-benzothiazepine-b 5-acetic acid.hydrochloride as a colorless powder.

$[\alpha]_D - Y°$ (c=0.8, in methanol).

EXAMPLE 79

In 5 ml of ethanol is dissolved 60 mg of ethyl 3(R)-(5-amino-1-ethoxycarbonylpentyl)amino-4-oxo-2,3,4,5-tetrahydro-1,5-benzothiazepine-5-acetate dihydrochloride, and 0.5 g of 25% aqueous glutaraldehyde solution and 0.3 g of sodium cyanoborohydride are added to the solution, followed by stirring at room temperature for 2 hours. Water (50 ml) is added to the reaction solution, followed by adding sodium chloride to saturate the solution. The solution is extracted twice with 30 ml of ethyl acetate, and the extract is washed with water, dried over anhydrous magnesium sulfate and concentrated under reduced pressure. The resulting oily material is dissolved in a small amount of ethyl ether, and 0.2 ml of 5N hydrogen chloride-ethyl acetate solution is added to the solution to give 50 mg of ethyl 3(R)-(1- ethoxycarbonyl-5-piperidinopentyl)amino-4-oxo-2,3,4,5-tetrahydro-1,5-benzothiazepine-5-acetate.dihydrochloride as a colorless powder.

Mass spectrum (m/e): 505 (M+).

EXAMPLE 80

In a mixture of 1 ml of methanol and 1 ml of 1N aqueous sodium hydroxide solution is dissolved 30 mg of ethyl 3(R)-(1-ethoxycarbonyl-5-piperidinopentyl)amino-4-oxo-2,3,4,5-tetrahydro-1,5-benzothiazepine-5-acetate.dihydrochloride as obtained in Example 79, and the solution is allowed to stand at room temperature for 1 hour. After methanol is evaporated off under reduced pressure, 2 ml of water and 0.5 ml of acetic acid are added to the residue, followed by purification by Amberlite XAD-2 column chromatography (acetone:water=2:1). The eluate is concentrated under reduced pressure, and the residue is lyophilized to give 17 mg of 3(R)-(1-carboxy-5-piperidinopentyl)amino-4-oxo-2,3,4,5-tetrahydro-1,5-benzothiazepine-5-acetic acid as a colorless powder.

SIMS spectrum (m/e): 450 (MH+); addition of KI: 488 (M+K)+.

EXAMPLE 81

In 10 ml of ethanol is dissolved 0.4 g of 3(R)-[5-amino-1(S)-ethoxycarbonylpentyl]amino-4-oxo-2,3,4,5-tetrahydro-1,5-benzothiazepine-5-acetic acid.dihydrochloride as obtained in Example 58, and 1.2 g of aqueous glutaraldehyde solution (25%) and 0.4 g of sodium cyanoborohydride are added to the solution, followed by stirring at room temperature for 1 hour. Water (50 ml) is added to the mixture, which is made acidic with 1N hydrochloric acid and extracted twice with 30 ml of ethyl acetate. The aqueous layer is neutralized with sodium hydrogencarbonate, and extracted twice with 30 ml of ethyl acetate. The aqueous layer is purified by Amberlite XAD-2 column chromatography (acetone:water=2:1), and the eluent is concentrated under reduced pressure and lyophilized to give 0.3 g of 3(R)-[1(S)-ethoxycarbonyl-5-piperidinopentyl]amino-4-oxo-2,3,4,5-tetrahydro-1,5-benzothiazepine-5-acetic acid as a colorless powder.

$[\alpha]_D$ −139° (c=0.4, in methanol).

SIMS spectrum (m/e): 478 (MH+).

Elemental analysis, for $C_{24}H_{35}N_3O_5S.H_2O$. Calcd.: C, 58.16; H, 7.53; N, 8.49. Found: C, 58.47; H, 7.55; N, 8.52.

EXAMPLE 82

In 5 ml of water is dissolved 0.23 g of 3(R)-[1(S)-ethoxycarbonyl-5-piperidinopentyl]amino-4-oxo-2,3,4,5-tetrahydro-1,5-benzothiazepine-5-acetic acid as obtained in Example 81, and 4 ml of 1N aqueous sodium hydroxide solution is added to the solution, followed by allowing the mixture to stand at room tmeperature for 1.5 hours. Acetic acid (1 ml) is added to the reaction solution, which then purified by Amberlite XAD-2 column chromatography to give a colorless powder. This product is dissolved in methanol, and the solution is concentrated under reduced pressure to give an agar-like material. The material is treated with 5 ml of ethanol and collected by filtration to gove 0.09 g of 3(R)-[1(S)-carboxy-5-piperidinopentyl]amino-4-oxo-2,3,4,5-tetrahydro-1,5-benzothiazepine-5-acetic acid as a colorless powder.

$[\alpha]_D$ −117° (c=0.2, in methanol).

SIMS spectrum (m/e): 450(MH+).

EXAMPLE 83

A 1.8 g quantity of tert-butyl 3(R)-[1-ethoxycarbonyl-3-phthalimidopropyl]amino-4-oxo-2,3,4,5-tetrahydro-1,5-benzothiazepine-5-acetate as obtained in Example 44 is separated and purified by silica-gel column chromatography (hexane:ethyl acetate=2:1) to give from the first fraction 0.8 g of tert-butyl 3(R)-[1(R)-ethoxycarbonyl-3-phthalimidopropyl]amino-4-oxo-2,3,4,5-tetrahydro-1,5-benzothiazepine-5-acetate is obtained as a colorless oily material.

IR $\nu_{max}^{neat}$cm$^{-1}$: 3320(NH), 1770, 1740, 1710, 1670(C=O).

$[\alpha]_D$ −142° (c=0.4, in methanol).

From the second fraction, 0.9 g of tert-butyl 3(R)-[1(S)-ethoxycarbonyl-3-phthalimidopropyl]amino-4-oxo-2,3,4,5-tetrahydro-1,5-benzothiazepine-5-acetate is obtained as a colorless oily material.

IR $\nu_{max}^{neat}$cm$^{-1}$: 3330(NH), 1770, 1740, 1720, 1680(C=O).

$[\alpha]_D$ −134° (c=0.4, in methanol).

EXAMPLE 84

In hydrogen chloride-ethyl acetate solution (5N, 5 ml) is dissolved 0.2 g of tert-butyl 3(R)-[1(S)-ethoxycarbonyl-3-phthalimidopropyl]amino-4-oxo-2,3,4,5-tetrahydro-1,5-benzothiazepine-5-acetate, and the solution is allowed to stand at room temperature for 4 hours. Petroleum ether (100 ml) is added to the reaction solution, and the deposited precipitate is collected by filtration to give 0.18 g of 3(R)-[1(S)-ethoxycarbonyl-3-phthalimidopropyl]amino-4-oxo-2,3,4,5-tetrahydro-1,5-benzothiazepine-5-acetic acid.hydrochloride as a colorless powder.

$[\alpha]_D$ −102° (c=0.3, in methanol).

EXAMPLE 85

In the same manner as Example 39, 2 g of tert-butyl 3(R)-amino-4-oxo-2,3,4,5-tetrahydro-1,5-benzothiazepine-5acetate is reacted with 7.1 g of 2-bromo-11-phthalimidoundecanate. The resulting product is separated and purified by silica-gel column chromatography (hexane:ethyl acetate=3:1) to give from the first fraction 1.2 g of tert-butyl 3(R)-[1(R)-ethoxycarbonyl-10-phthalimidodecyl]amino-4-oxo-2,3,4,5-tetrahydro-1,5-benzothiazepine-5-acetate as a colorless oily material.

IR $\nu_{max}^{neat}$cm$^{-1}$: 3320(MH), 1770, 1740, 1710, 1680(C=O).

$[\alpha]_D$ −104° (c=0.5, in methanol).

From the second fraction, there is obtained 1.2 g of tert-butyl 3(R)-[1(S)-ethoxycarbonyl-10-phthalimidodecyl]amino-4-oxo-2,3,4,5-tetrahydro-1,5-benzothiazepine-5-acetate as a colorless oily material.

IR $\nu_{max}^{neat}$cm$^{-1}$: 3320(NH), 1770, 1740, 1710, 1670(C=O).

$[\alpha]_D$ −113° (c=0.5, in methanol).

EXAMPLE 86

In the same manner as Example 84, 0.25 g of tert-butyl 3(R)-[1(S)-ethoxycarbonyl-10-phthalimidodecyl]amino-4-oxo-2,3,4,5-tetrahydro-1,5-benzothiazepine-5-acetate as obtained in Example 85 is treated with hydrogen chloride-ethyl acetate solution (5N) to give 0.23 g of 3(R)-[1(S)-ethoxycarbonyl-10-phthalimidodecyl]amino-4-oxo-2,3,4,5-tetrahydro-1,5-benzothiazepine-5-acetic acid.hydrochloride as a colorless powder.

$[\alpha]_D$ −101° (c=0.4, in methanol).

EXAMPLE 87

A mixture of 0.4 g of tert-butyl 3(R)-amino-4-oxo-2,3,4,5-tetrahydro-1,5-benzothiazepine-5-acetate, 1 g of ethyl 4-(1-benzyloxycarbonyl-4-piperidyl)-2-chlorobutyrate, 0.2 g of triethylamine, 0.9 g of potassium iodide and 50 ml of acetonitrile is heated under reflux for 2 days. After cooling, the reaction solution is concentrated under reduced pressure, and the residue is purified by silica-gel column chromatography (hexane:ethyl acetate=2:1) to give 0.15 g of tert-butyl 3(R)-[3-(1-benzyloxycarbonyl-4-piperidyl)-1(R)-ethoxycarbonylpropyl]amino-4-oxo-2,3,4,5-tetrahydro-1,5-benzothiazepine-5-acetate and 0.25 g of tert-butyl 3(R)-[3-(1-benzyloxycarbonyl-4-piperidyl)-1(S)-ethoxycarbonylpropyl]amino-4-oxy-2,3,4,5-tetrahydro-1,5-benzothiazepine-5-acetate as a colorless oily material, respectively.

EXAMPLE 88

In 30 ml of ethanol is dissolved 2.1 g of tert-butyl 3(R)-amino-4-oxo-2,3,4,5-tetrahydro-1,5-benzothiazepine-5acetate, and 0.4 g of acetic acid, 2.5 g of ethyl 5-(1-benzyloxycarbonyl-4-piperidyl)-2-oxovalerate and 10 g of Molecular sieve 3A are added to the solution. The mixture is stirred at room temperature for 20 minutes, and a solution of 0.4 g of sodium cyanoborohydride in 50 ml of ethanol is added dropwise to the mixture at room temperature with stirring over the period of 3 hours. The reaction solution is allowed to stand at room temperature overnight, and concentrated under reduced pressure, and 300 ml of water and 300 ml of ethyl acetate are added to the residue, followed by shaking. The insoluble matter is removed by filtration, and the ethyl acetate layer is dried over anhydrous magnesium sulfate and concentrated under reduced pressure. Ethyl acetate (20 ml) and 2 g of oxalic acid are added to the residue, and the mixture is shaken thoroughly and admixed with 300 ml of petroleum ether, followed by allowing the mixture to stand. The solution portion is removed by decantation, and 100 ml of water and 200 ml of ethyl acetate are added to the precipitate portion, followed by adding excess sodium hydrogencarbonate to conduct neutralization. The ethyl acetate layer is dried over anhydrous magnesium sulfate and concentrated under reduced pressure to give an oily material. This product is separated and purified by silica-gel column chromatography (hexane:ethyl acetate=2:1) to give from the first fraction 0.4 g of tert-butyl 3(R)-[4-(1-benzyloxycarbonyl-4-piperidyl)-1(R)-ethoxycarbonylbutyl]amino-4-oxo-2,3,4,5-tetrahydro-1,5-benzothiazepine-5-acetate as a colorless oily material.

IR $\nu_{max}^{neat}$cm$^{-1}$: 3310(NH), 1730, 1680(C=O).

Mass spectrum (m/e): 653 (M+).

From the subsequent fraction there is obtained 0.8 g of tert-butyl 3(R)-[4-(1-benzyloxycarbonyl-4-piperidyl)-1(S)ethoxycarbonylbutyl]amino-4-oxo-2,3,4,5-tetrahydro-1,5-benzothiazepine-5-acetate as a colorless oily material.

IR $\nu_{max}^{neat}$cm$^{-1}$: 3320(NH), 1730, 1690(C=O).

Mass spectrum (m/e): 653 (M+).

EXAMPLE 89

In 2 ml of acetic acid is dissolved 0.4 g of tert-butyl 3(R)-[4-(1-benzyloxycarbonyl-4-piperidyl)-1(R)-ethoxycarbonylbutyl]amino-4-oxo-2,3,4,5-tetrahydro-1,5-benzothiazepine-5-acetate, and 2 ml of 30% hydrogen bromide-acetic acid solution is added to the solution, followed by allowing the mixture to stand at room temperature for 1.5 hours. Ethyl ether (50 ml) is added to the reaction solution, which is then allowed to stand. The supernatant is decanted, and the precipitate is washed with ethyl ether and dried to give 0.4 g of 3(R)-[1(R)-ethoxycarbonyl-4-(4-piperidyl)butyl]amino-4-oxo-2,3,4,5-tetrahydro-1,5-benzothiazepine-5-acetic acid.dihydrobromide as a colorless powder.

Elemental analysis, for $C_{23}H_{33}N_3O_5S.2HBr. 2H_2O$. Calcd.: C, 41.76; H, 5.94; N, 6.35. Found: C, 42.07; H, 6.16; N, 6.09.

$[\alpha]_D -111°$ (in methanol).

Mass spectrum (m/e): 463 (M+).

EXAMPLE 90

In 2 ml of acetic acid is dissolved 0.8 g of tert-butyl 3(R)-[4-(1-benzyloxycarbonyl-4-piperidyl)-1(S)-ethoxycarbonylbutyl]amino-4-oxo-2,3,4,5-tetrahydro-1,5-benzothiazepine-5acetate, and 3 ml of 30% hydrogen bromide-acetic acid solution is added to the solution, followed by allowing the mixture to stand at room temperature for 1.5 hours. Ethyl ether (50 ml) is added to the reaction solution, which is then allowed to stand, The supernatant is decanted, and the precipitate is washed with ethyl ether and dried to give 0.75 g of 3(R)-[1(S)-ethoxycarbonyl-4-(4-piperidyl)butyl]-amino-4-oxo-2,3,4,5-tetrahydro-1,5-berzothiazepine-5-acetic acid.dihydrobromide as a colorless powder.

Elemental analysis, for $C_{23}H_{33}N_3O_5S.2HBr.3/2H_2O$. Calcd.: C, 42.34; H, 5.87; N, 6.44. Found: C, 42.35; H, 6.03; N, 6.12.

$[\alpha]_D -89°$ (in methanol).

Mass spectrum (m/e): 463 (M+).

EXAMPLE 91

In 12 ml of 1N aqueous sodium hydroxide solution is dissolved 0.5 g of 3(R)-[1(S)-ethoxycarbonyl-4-(4-piperidyl)butyl]amino-4-oxo-2,3,4,5-tetrahydro-1,5-benzothiazepine-5-acetic acid.dihydrobromide, and the solution is allowed to stand at room temprature fof 30 minutes. The solution is neutralized with 2 ml of acetic acid, and purified by MCI-gel (CHP 20P, 150 to 300μ, Mitsubishi Chemical Industries, Japan) column chormatography (water:methanol=2:1). The eluent is concentrated under reduced pressure, and the residue is lyophilized to give 0.3 g of 3(R)-[1(S)-carboxy-4-(4-piperidyl)butyl]amino-4-oxo-2,3,4,5-tetrahydro-1,5-benzothiazepine-5-acetic acid as a colorless powder.

Elemental analysis, for $C_{21}H_{29}N_3O_5S.2H_2O$. Calcd.: C, 53.49; H, 7.05; N, 8.91. Found: C, 53.77; H, 7.11; N, 8.96.

$[\alpha]_D -117°$ (in methanol-water).

SIMS spectrum (m/e): 436 (MH+).

EXAMPLE 92

In 30 ml of ethanol is dissolved 3 g of tert-butyl 3(R)-amino-4-oxo-2,3,4,5-tetrahydro-1,5-benzothiazepine-5-acetate, and 0.58 g of acetic acid, 4.4 g of ethyl 6-(1-benzyloxycarbonyl-4-piperidyl)-2-oxohexanoate and 10 g of Molecular sieve 3A are added to the solution. The mixture is stirred at room temperature for 15 minutes, and a solution of 0.61 g of sodium cyanoborohydride in 50 ml of ethanol is added dropwise to the mixture at room temperature with stirring over the period of 3 hours.

The reaction is allowed to stand at room temperature overnight and then concentrated under reduced pressure, and 100 ml of water and 200 ml of ethyl acetate are added to the residue, followed by shaking thoroughly. The insoluble matter is removed by filtration, and the ethyl acetate layer is washed with 10% aqueous phosphoric acid solution, 0.1N aqueous sodium hydroxide solution and water successively, dried over anhydrous magnesium sulfate and concentrated under reduced pressure. The residue is separated and purified by silicagel column chromatography (hexane:ethyl acetate=2:1) to give from the first fraction 0.45 g of tert-butyl 3(R)-[5-(1-benzyloxycarbonyl-4-piperidyl)-1(R)-ethoxycarbonylpentyl]-amino-4-oxo-2,3,4,5-tetrahydro-1,5-benzothiazepine-5-acetate as a colorless oily material.

IR $\nu_{max}^{neat}$cm$^{-1}$: 3330(NH), 1740, 1700(C=O).
Mass spectrum (m/e): 667 (M+).

From the subsequent fraction, 0.8 g of tert-butyl 3(R)-[5-(1-benzyloxycarbonyl-4-piperidyl)-1(S)-ethoxycarbonylpentyl]-amino-4-oxo-2,3,4,5-tetrahydro-1,5-benzothiazepine-5-acetate is obtained as a colorless oily material.

IR $\nu_{max}^{neat}$cm$^{-1}$: 3320(NH), 1740, 1690(C=O).
Mass spectrum (m/e): 667 (M+).

EXAMPLE 93

In 1 ml of acetic acid is dissolved 0.45 g of tert-butyl 3(R)-[5-(1-benzyloxycarbonyl-4-piperidyl)-1(R)-ethoxycarbonylpentyl]amino-4-oxo-2,3,4,5-tetrahydro-1,5-benzothiazepine-5-acetate, and 1 ml of 30% hydrogen bromide-acetic acid solution is added to the solution, followed by allowing the mixture to stand at room temperature for 1.5 hours. Ethyl ether (200 ml) is added to the reaction solution, which is then allowed to stand. The supernatant liquid is decanted, and the precipitate is washed with ethyl ether and dried to give 0.3 g of 3(R)-[1(R)-ethoxycarbonyl-5-(4-piperidyl)pentyl]-amino-4-oxo-2,3,4,5-tetrahydro-1,5-benzothiazepine-5-acetic acid.dihydrobromide as a colorless powder.

Elemental analysis, for $C_{24}H_{35}N_3O_5S.2HBr.H_2O$. Calcd.: C, 43.85; H, 5.98; N, 6.39. Found: C, 43.95; H, 6.29; N, 6.47.

$[\alpha]_D$ −108° (in methanol).
Mass spectrum (m/e): 477 (M+).

EXAMPLE 94

In 1 ml of acetic acid is dissolved 0.75 g of tertbutyl 3(R)-[5-(1-benzyloxycarbonyl-4-piperidyl)-1(S)-ethoxycarbonylpentyl]amino-4-oxo-2,3,4,5-tetrahydro-1,5-benzothiazepine-5-acetate, and 2 ml of 30% hydrogen bromide-acetic acid solution is added to the solution, followed by allowing the mixture to stand at room temperature for 1.5 hours. Ethyl ether (200 ml) is added to the reaction solution, which is then allowed to stand. The supernatant liquid is decanted, and the precipitate is washed with ethyl ether and dried to give 0.6 g of 3(R)-[1(S)-ethoxycarbonyl-5-(4-piperidyl)pentyl]amino-4-oxo-2,3,4,5-tetrahydro-1,5-benzothiazepine-5-acetic acid.dihydrobromide as a colorless powder.

$[\alpha]_D$ −89° (in methanol).
Mass spectrum (m/e): 477 (M+).

EXAMPLE 95

In 10 ml of 1N aqueous sodium hdyroxide solution is dissolved 0.45 g of 3(R)-[1(S)-ethoxycarbonyl-5-(4-piperidyl)pentyl]amino-4-oxo-2,3,4,5-tetrahydro-1,5-benzothiazepine-5acetic acid.dihydrobromide, and the solution is allowed to stand at room temperature for 30 minutes. The reaction solution is neutralized with 2 ml of acetic acid and purified by MCI gel column chromatography (water:methanol=2:1). The eluent is concentrated under reduced pressure and the residue is lyophilized to give 0.3 g of 3(R)-[1(S)-carboxy-5-(4-piperidyl)-pentyl]amino-4-oxo-2,3,4,5-tetrahydro-1,5-benzothiazepine-5-acetic acid as a colorless powder.

Elemental analysis, for $C_{22}H_{31}N_3O_5S.2H_2O$. Calcd.: C, 54.42; H, 7.27; N, 8.66. Found: C, 54.84; H, 7.38; N, 8.61.

$[\alpha]_D$ −131° (in methanol-water).
SIMS spectrum (m/e): 450 (MH+).

EXAMPLE 96

In 30 ml of ethanol is dissolved 2.5 g of tert-butyl 3(R)-amino-4-oxo-2,3,4,5-tetrahydro-1,5-benzothiazepine-5acetate, and 0.5 g of acetic acid, 3.2 g of ethyl 7-(1-benzyloxycarbonyl-4-piperidyl)-2-oxoheptanoate and 10 g of Molecular sieve 3A are added to the solution. The mixture is stirred at room temperature for 10 minutes, and a solution of 0.51 g of sodium cyanoborohydride in 50 ml of ethanol is added dropwise to the mixture at room temperature with stirring over the period of 3 hours.

The reaction solution is allowed to stand at room temperature dvernight, and concentrated under reduced pressure, and 50 ml of water and 200 ml of ethyl acetate are added to the residue, followed by shaking thoroughly. The insoluble matter is removed by filtration, and the ethyl acetate layer is washed with 0.1N hydrochloric acid, 0.1N aqueous sodium hydroxide solution and water successively, dried over anhydrous magnesium sulfate and concentrated uhder reduced pressure. The residue is separated and purified by silicagel column chromatography (hexane:ethyl acetate=2:1) to give from the first fraction 0.5 g of tert-butyl 3(R)-[6-(1-benzyloxycarbonyl-4-piperidyl)-1(R)-ethoxycarbonylhexyl]amino-4-oxo-2,3,4,5-tetrahydro-1,5-benzothiazepine-5-acetate as a colorless oily material.

IR $\nu_{max}^{neat}$cm$^{-1}$: 3320(NH), 1730, 1680(C=O).
Mass spectrum (m/e): 681 (M+).

From the subsequent fraction, 0.9 g of tert-butyl 3(R)-[6-(1-benzyloxycarbonyl-4-piperidyl)-1(S)-ethoxycarbonylhexyl]amino-4-oxo-2,3,4,5-tetrahydro-1,5-benzothiazepine-5-acetate is obtained as a colorless oily material.

IR $\nu_{max}^{neat}$cm$^{-1}$: 3330(NH), 1730, 1690(C=O).
Mass spectrum (m/e): 681 (M+).

EXAMPLE 97

In 1 ml of acetic acid is dissolved 0.5 g of tert-butyl 3(R)-[6-(1-benzyloxycarbonyl-4-piperidyl)-1(R)-ethoxycarbonylhexyl]amino-4-oxo-2,3,4,5-tetrahydro-1,5-benzothiazepine-5-acetate, and 2 ml of 30% hydrogen bromide-acetic acid solution is added to the solution, followed by allowing the mixture to stand at room temperature for 1 hour. Ethyl ether (200 ml) is added to the reaction solution, which is then allowed to stand. The supernatant liquid is decanted, and the precipitate is dissolved in 20 ml of 1N aqueous sodium hydroxide solution, followed by allowing the solution to stand at room temperature for 30 minutes. The solution is neutralized by adding 2 ml of acetic acid, and purified by MCI-gel column chromatography (water:methanol=1:2). The eluent is concentrated under reduced pressure, and the residue is lyophilized to give 0.23 g of 3(R)-[1(R)-carboxy-6-(4-piperidyl)hexyl]amino-4-oxo-2,3,4,5-tetrahydro-1,5-benzothiazepine-5-acetic acid as a colorless powder.

$[\alpha]_D$ −144° (in water).

EXAMPLE 98

In 1 ml of acetic acid is dissolved 0.9 g of tert-butyl 3(R)-[6-(1-benzyloxycarbonyl-4-piperidyl)-1(S)-ethoxycarbonylhexyl]amino-4-oxo-2,3,4,5-tetrahydro-1,5-benzothiazepine-5-acetate, and 2 ml of 30% hydrogen bromide-acetic acid solution is added to the solution, followed by allowing the mixture to stand at room temperature for 1.5 hours. Ethyl ether (200 ml) is added to the reaction solution, which is then allowed to stand. The supenatant liquid is decanted, and the precipitate is dissolved in 30 ml of 1N aqueous sodium hydroxide solution, followed by allowing the solution to stand at room temperature for 30 minutes. The solution is neutralized by adding 3 ml of acetic acid, and purified by MCI-gel chromatography (water:methanol=1:2). The eluent is concentrated under reduced pressure, and the residue is lyophilized to give 0.43 g of 3(R)-[1(S)-carboxy-6-(4-piperidyl)hexyl]amino-4-oxo-2,3,4,5-tetrahydro-1,5-benzothiazepine-5-acetic acid as a colorless powder.

$[\alpha]_D - 121°$ (in water).
SIMS spectrum (m/e): 464 (MH+).

EXAMPLE 99

In 30 ml of ethanol is dissolved 2 g of tert-butyl 3(R)-amino-4-oxo-2,3,4,5-tetrahydro-1,5-benzothiazepine-5-acetate, and 0.47 g of acetic acid, 3 g of ethyl 8-(1-benzyloxycarbonyl-4-piperidyl)-2-oxooctanoate and 10 g of Molecular sieve 3A are added to the solution. The mixture is stirred at room temperature for 10 minutes, and a solution of 0.45 g of sodium cyanoborohydride in 40 ml of ethanol is added to the mixture at room temperature with stirring over the period of 3 hours.

The reaction solution is allowed to stand at room temperature overnight, and then concentrated under reduced pressure, and 100 ml of water and 200 ml of ethyl acetate are added to the residue, followed by shaking. The insoluble matter is removed by filtration, and the ethyl acetate layer is washed with water, dried over anhydrous magnesium sulfate and concentrated under reduced pressure. The residue is separated and purified by silica-gel column chromatography (hexane:ethyl acetate=3:1 to 2:1) to give 0.3 g of tert-butyl 3(R)-[7-(1-benzyloxycarbonyl-4-piperidyl)-1(S)-ethoxycarbonylheptyl]amino-4-oxo-2,3,4,5-tetrahydro-1,5-benzothiazepine-5-acetate as a colorless oily material.

IR $\nu_{max}^{neat}$cm$^{-1}$: 3320(N-H), 1730, 1690(C=O).
Mass spectrum (m/e): 695(M+).

EXAMPLE 100

In 1.5 ml of acetic acid is dissolved 0.3 g of tertbutyl 3(R)-[7-(1-benzyloxycarbonyl-4-piperidyl)-1(S)-ethoxycarbonylheptyl]amino-4-oxo-2,3,4,5-tetrahydro-1,5-benzothiazepine-5-acetate, and 1 ml of 30% hydrogen-bromide acetic acid solution is added to the solution, followed by allowing the mixture to stand at room temperature for 0.5 hour. Ethyl ether (80 ml) is added to the reaction solution, which is then allowed to stand. The supernatant liquid is decanted, and the precipitate is dissolved in 10 ml of 1N aqueous sodium hydroxide solution, followed by allowing the solution to stand at room temperature for 30 minutes. The solution is neutralized with 2 ml of acetic acid, and purified by XAD-2 column chromatography (water:methanol=1:1). The eluent is concentrated under reduced pressure, and the residue is lyophilized to give 0.1 g of 3(R)-[1(S)-carboxy-7-(4-piperidyl)heptyl]amino-4-oxo-2,3,4,5-tetrahydro-1,5-benzothiazepine-5-acetic acid as a colorless powder.

$[\alpha]_D - 116°$ (in water).
SIMS spectrum (m/e): 478 (MH+).

EXAMPLE 101

A mixture consisting of 25 g of isonicotine aldehyde, 82 g of ethyl (triphenylphosphoranilidene)acetate and 300 ml of toluene is stirred at 100° C. for 3 hours. After cooling, the deposited crystals are removed by filtration, and the filtrate is concentrated under reduced pressure. A mixture of ethyl acetate and petorleum ether (1:1, 400 ml) is added to the residue, and the mixture is extracted with 500 ml of 5% hydrochloric acid. The aqueous solution portion is extracted with 50 ml of ethyl acetate, followed by neutralization with potassium carbonate and cooling. The deposited crystals are collected by filtration and dried to give 34 g of 3-(4-pyridyl)acrylate as colorless prisms.

m.p. 64°-66° C.

EXAMPLE 102

In 300 ml of acetic acid is dissolved 28 g of ethyl 3-(4-pyridyl)acrylate, and a catalytic reduction reaction is carried out at ordinary temperature and at atmospheric pressure using 1 g of platinum oxide as a catalyst. After absorption of hydrogen stops, the catalyst is removed by filtration, and the filtrate is concentrated under reduced pressure. Water (500 ml) and 300 ml of ethyl acetate are added to the residue, and sodium hydrogencarbonate is added to the mixture under stirring until no foaming is observed. Benzyloxycarbonyl chloride (5 ml) is added to the resulting mixture, followed by stirring at room temperature for 1 hour, and 20 ml of benzyloxycarbonyl chloride is further added. Sodium hydrogencarbonate (30 mg) is added portionwise to the reaction solution at room temperature with stirring, and after the mixture is stirred at room temperature for 2 hours, the ethyl acetate layer is separated, washed with water, dried over anhydrous magnesium sulfate and concentrated under reduced pressure. The resulting oily material is purified by silica-gel column chromatography (hexane:ethyl acetate=2:1) to give 37 g of ethyl 3-(1-benzyloxycarbonyl-4-piperidyl)propionate as a colorless oily material.

IR $\nu_{max}^{neat}$cm$^{-1}$: 1730, 1700(C=O).

EXAMPLE 103

In 30 ml of ethanol is dissolved 17 g of ethyl 4-(1-benzyloxycarbonyl-4-piperidyl)-2-oxobutyrate, and 4.5 g of acetic acid is added to the solution. Sodium cyanoborohydride (3 g) is added to the mixture at room temperature with stirring, followed by stirring at room temperature for 3 hours, and 500 ml of water is added to the reaction mixture, which is extracted with methylene chloride. The extract is dried over anhydrous magnesium sulfate and concentrated under reduced pressure, and the resulting residue is purified by silica-gel column chromatography (hexane:ethyl acetate=2:1 to 1:1) to give 11.5 g of ethyl 4-(1-benzyloxycarbonyl-4-piperidyl)-2-hydroxybutyrate as a colorless oily material.

IR $\nu_{max}^{neat}$cm$^{-1}$: 3430(OH), 1730, 1690(C=O).
NMR spectrum (in CDCl$_3$+D$_2$O)δ: 7.3(5H), 5.1(2H), 3.9-4.4 (5H), 2.5-3.1(2H), 1.0-2.0(12H).

EXAMPLE 104

In a mixture of 200 ml of ethyl acetate and 12 g of pyridine is dissolved 11.5 g of ethyl 4-(1-benzyloxycarbonyl-4-piperidyl)-2-hydroxybutyrate, and 5 ml of thionyl chloride is added to the solution, followed by refluxing with stirring for 1 hour. After cooling, 500 ml of ethyl acetate of water and 100 ml are added to the reaction solution, followed by extraction. The extract is washed with 0.1N hydrochloric acid and water successively, dried over anhydrous magnesium sulfate and treated with activated carbon. The ethyl acetate is evaporated off to give 10.5 g of ethyl 4-(1-benzyloxycarbonyl-4-piperidyl)-2-chlorobutyrate pale yellow oil.

IR$\nu_{max}^{neat}$cm$^{-1}$:1740, 1690(C=O).

EXAMPLE 105

In 20 ml of ethanol is dissolved 10.5 g of ethyl 4-(1-benzyloxycarbonyl -4-piperidyl)-2-chlorobutyrate, and a catalytic reduction reaction is carried out at ordinary temperature and at atmosphereic pressure using 5 g of 10% palladium-carbon (50% in water ) as a catalyst. After absorption of hydrogen stops, the catalyst is removed by filtration, and the filtrate is concentrated under reduced pressure to give ethyl 4-(4-piperidyl)butyrate. This product is dissolved in a mixture of 200 ml of ethyl acetate and 100 ml of water, 6 g of sodium hydrogencarbonate is added to the solution, followed by stirring at room temperature. Benzyloxycarbonyl chloride (6 ml) is added dropwise to the mixture, and after the addition is completed, the mixture is stirred at room temperature for 1.5 hours. The ethyl acetate layer is separated, dried over anhydrous magnesium sulfate and concentrated under reduced pressure. The residue is purified by silica-gel column chromatography (hexane:ethyl acetate=3:1) to give 5.3 g of ethyl 4-(1-benzyloxycarbonyl-4-piperidyl)butyrate as a colorless oily material.

IR$\nu_{max}^{neat}$cm$^{-1}$:1730, 1700(C=O).

EXAMPLE 106

In 10 ml of ethanol is dissolved 0.48 g of sodium, and 5.3 g of ethyl 4-(1-benzyloxycarbonyl-4-piperidyl)butyrate and 2.8 g of diethyl oxalate are added to the solution, followed by evaporation under reduced pressure at 60° to 70° C. to remove the low-boiling substance. After cooling, the resulting brown viscous material is treated with 300 ml of water, and the mixture is made acidic with 1N hydrochloric acid and extracted twice with 100 ml of ethyl acetate. The extract is dried over anhydrous magnesium sulfate and concentrated under reduced pressure. Dimethylsulfoxide (45 ml), 5 ml of water and 0.8 g of lithium chloride are added to the resulting oily material, and the mixture is stirred at 135° to 140° C. for 1.5 hours and further at 140° to 145° C. for 30 minutes. After cooling, 500 ml of water is added to the reaction solution, and the mixture is extracted with 300 ml of ethyl acetate. The extract is dried over anhydrous magnesium sulfate and concentrated under reduced pressure to give 5 g of ethyl 5-(1-benzyloxycarbonyl-4-piperidyl)-2-oxovalerate as an oily material.

IR$\nu_{max}^{neat}$cm$^{-1}$:1730, 1700(C=O).

Mass spectrum (m/e): 361 (M+).

EXAMPLE 107

A solution of 84 g of 3-(4-piperidyl)propanol and 65 g of triethylamine in 100 ml of methylene chloride, simultaneously with 100 g of benzyloxycarbonyl chloride, is added dropwise to a mixture of 400 ml of methylene chloride and 40 ml of water at room temperature with stirring over the period of 45 minutes. After the addition is completed, the reaction solution is stirred at room temperature for 1 hour. The methylene chloride layer is separated, washed with water, dried over anhydrous magnesium sulfate and concentrated under reduced pressure. The resulting oily material is distilled under vacuo to remove the fraction of b.p. 50° to 60° C./5 mmHg, to give 110 g of 3-(1-benzyloxycarbonyl-4-piperidyl) as pale yellow oil.

IR$\nu_{max}^{neat}$cm$^{-1}$:3400(OH), 1680(C=O).

EXAMPLE 108

A mixture of 110 g of 3-(1-benzyloxycarbonyl-4-piperidyl)propanol and 500 ml of pyridine is stirred under ice-cooling, and 100 g of tosyl chloride is added portionwise to the mixture over the period of 2 hours. The reaction solution is further stirred under ice-cooling for 1 hour, and 1 l of ice cold water is added dropwise to the solution.

Successively, 500 ml of conc. hydrochloric acid is added dropwise to the reaction mixture under ice-cooling, followed by extraction with 1 l of ethyl acetate. The extract is washed with dilute hydrochloric acid and water successively, dried over anhydrous magnesium sulfate and concentrated under reduced pressure. Ethanol is added to the resulting oily material, and the mixture is allowed to stand to give 99 g of 3-(1-benzyloxycarbonyl-4-piperidyl)propyl p-toluenesulfonate as colorless crystals, melting at 59°–60° C.

Elemental analysis, for $C_{23}H_{29}NO_5S$. Calcd.: C, 64.01; H, 6.77; N, 3.25. Found: C, 64.25; H, 6.78; N, 3.26.

EXAMPLE 109

In 300 ml of ethanol is dissolved 5.8 g of sodium, and 40 g of diethyl malonate is added to the solution, followed by stirring. 3-(1-Benzyloxycarbonyl-4-piperidyl)-propyl p-toluenesulfonate (90.5 g) is added to this mixture followed by refluxing with stirring for 2 hours. After cooling, 1 l of water is added to the reaction solution, which is then extracted with 500 ml of ethyl acetate. The extract is dried over anhydrous magnesium sulfate and concentrated under reduced pressure to give ethyl 5-(1-benzyloxycarbonyl-4-piperidy)-2-ethoxycarbonylvalearate as an oily material. This product is dissolved in 200 ml of ethanol, and a solution of 34 g of sodium hydroxide in 200 ml of water is added dropwise to the solution with stirring. After the addition is completed, 300 ml of water is added to the reaction solution, which is then extracted with a mixture of ether and petroleum ether (1:1, 300 ml). The aqeuous layer is made acidic with conc. hydrochloric acid, followed by extraction with 500 ml of ethyl acetate. The extract is washed with water, dried over anhydrous magnesium sulfate and concentrated under reduced pressure to give 5-(1-benzyloxycarbonyl-4-piperidyl)-2-carboxyvaleric acid as an oily material. This product is heated at 160° to 170° C. with stirring for 45 minutes to give 50 g of 5-(1-benzyloxycarbonyl-4-piperidyl)valeric acid as an oily material.

IR$\nu_{max}^{neat}$ cm$^{-1}$: 1730, 1700(C=O).

EXAMPLE 110

A mixture of 54.8 g of 5-(1-benzyloxycarbonyl-4-piperidyl)valeric acid, 29 g of sodium hydrogencarbonate, 21 ml of ethyl iodide and 150 ml of N,N-dimethylformamide is heated at 70° to 80° C. with stirring for 3 hours. Ethyl iodide (10 ml) is additionally added to the reaction solution, followed by heating at 90° to 100° C. for 3 hours. After cooling, 1 l of water is added to the reaction solution, and the mixture is extracted with 1 l of ethyl acetate. The extract is washed with water, 1N hydrochloric acid and dilute aqueous sodium hydrogencarbonate solution successively, dried over anhydrous magnesium sulfate and concentrated under reduced pressure to give 58 g of ethyl 5-(1-benzyloxycarbonyl-4-piperidyl)valerate as pale yellow oil.

IR$\nu_{max}^{neat}$cm$^{-1}$: 1730, 1700(C=O).

NMR spectrum (in CDCl$_3$)δ: 7.3(5H), 5.1(2H), 3.9–4.4(4H), 2.5–3.1(2H), 2.1–2.5(2H), 1.0–1.9(14H).

EXAMPLE 111

In 50 ml of ethanol is dissolved 2.2 g of sodium, and 30 g of ethyl 5-(1-benzyloxycarbonyl-4-piperidyl)valerate and 14 g of diethyl oxalate are added to the solution, followed by evaporation under reduced pressure at 60° C. for 1 hour and at 60° to 70° C. for 30 minutes to remove a low boiling substance. After cooling, 500 ml of water is added to the resulting brown viscous material, and the mixture is made acidic with hydrochloric acid and extracted with 300 ml of ethyl acetate. The extract is dried over anhydrous magnesium sulfate and concentrated under reduced pressure. Dimethylsulfoxide (150 ml), 15 ml of water and 5 g of lithium chloride are added to the resulting oily material, followed by stirring at 150° to 155° C. for 35 minutes. After cooling, 500 ml of water is added to the reaction, and the mixture is extracted with 300 ml of ethyl acetate. The extract is dried over anhydrous magnesium sulfate and concentrated under reduced pressure to give 26 g of ethyl 6-(1-benzyloxycarbonyl -4-piperidyl)-2-oxohexanoate as an oily material.

IR$\nu_{max}^{neat}$cm$^{-1}$: 1730, 1690(C=O).

Mass spectrum (m/e): 375 (M+).

EXAMPLE 112

In 40 ml of ethanol is dissolved 26 g of ethyl 6-(1-benzyloxycarbonyl-4-piperidyl)-2-oxohexanoate, and 6.2 g of acetic acid is added to the solution. Sodium cyanoborohydride (4.4 g) is added to the mixture under ice-cooling, and the mixture is stirred for 1 hour and allowed to stand at room temperature overnight. Water (500 ml) is added to the reaction solution, followed by extraction with methylene chloride. The extract is dried over anhydrous magnesium sulfate and concentrated under reduced pressure. The resulting brown viscous material is purified by silica-gel column chromatography (hexane:ethyl acetate=2:1) to give 16 g of ethyl 6-(1-benzyloxycarbonyl-4-piperidyl)-2-hydroxyhexanoate as a colorless oily material.

IR$\nu_{max}^{neat}$cm$^{-1}$: 3450(OH), 1730, 1690(C=O).

EXAMPLE 113

In a mixture of 120 ml of ethyl acetate and 13 g of pyridine is dissolved 12.8 g of ethyl 6-(1-benzyloxycarbonyl -4-piperidyl)-2-hydroxyhexanoate, and 5.1 ml of thionyl chloride is added to the solution, followed by refluxing with stirring for 45 minutes. After cooling, 500 ml of water and 200 ml of ethyl acetate are added to the reaction solution, and extraction is carried out. The extract is washed with 0.1 N hydrochloric acid and water successively, dried over anhydrous magnesium sulfate and concentrated under reduced pressure. The resulting oily material is purified by silica gel column chromatography (hexane:ethyl acetate=4:1) to give 10 g of ethyl 6-(1-benzyloxycarbonyl-4-piperidyl)-2-chlorohexanoate as a colorless oily material.

IR$\nu_{max}^{neat}$cm$^{-1}$: 1740, 1690(C=O).

EXAMPLE 114

In 200 ml of ethanol is dissolved 10 g of ethyl 6-(1-benzyloxycarbonyl-4-piperidyl)-2-chlorohexanoate, and a catalytic reduction reaction is carried out at ordinary temperature and at atmospheric pressure using 5 g of 10% palladium-carbon (50% in water) as a catalyst. After absorption of hydrogen stops, the catalyst is removed by filtration, and the filtrate is concentrated under reduced pressure to give ethyl 6-(4-piperidyl)hexanoate. Water (100 ml) and 200 ml of ethyl acetate are added to this product, and 10 g of sodium hydrogencarbonate is added to the mixture, followed by stirring. Benzyloxycarbonyl chloride (7.2 ml) is added dropwise to the mixture at room temperature, followed by stirring overnight. The ethyl acetate layer is separated, dried over anhydrous magnesium sulfate and concentrated under reduced pressure. The residue is purified by silica-gel column chromatography (hexane:ethyl acetate=4:1) to give 7.7 g of ethyl 6-(1-benzyloxycarbonyl-4-piperidyl)hexanoate as a colorless oily material.

IR$\nu_{max}^{neat}$cm$^{-1}$: 1730, 1690(C=O).

EXAMPLE 115

In 20 ml of ethanol is dissolved 0.56 g of sodium, and 7.3 g of ethyl 6-(1-benzyloxycarbonyl-4-piperidyl)hexanoate and 3.5 g of diethyl oxalate are added to the solution, followed by evaporation under reduced pressure at 60° to 70° C. for 20 minutes and at 75° C. for 20 minutes to remove a low-boiling substance. After cooling, 100 ml of water is added to the resulting brown viscous material, and the mixture is made acidic with hydrochloric acid and extracted with 300 ml of ethyl acetate. The extract is dried over anhydrous magnesium sulfate and concentrated under reduced pressure. Dimethylsulfoxide (50 ml), 5 ml of water and 1.5 g of lithium chloride are added to the resulting oily material, followed by stirring at 140° to 160° C. for 40 minutes. After cooling, 300 ml of water is added to the reaction solution, which is then extracted with 300 ml of ethyl acetate. The extract is dried over anhydrous magnesium sulfate and concentrated under reduced pressure to give 6.5 g of ethyl 7-(1-benzyloxycarbonyl-4-piperidyl)-2-oxoheptanoate as an oily material.

IR$\nu_{max}^{neat}$cm$^{-1}$: 1720, 1690(C=O).

Mass spectrum (m/e): 389 (M+).

EXAMPLE 116

In 200 ml of tetrahydrofuran is dissolved 26.8 g of ethyl 5-(1-benzyloxycarbonyl-4-piperidyl)valerate, and 13.4 g of sodium borohydride is added to the solution. Methanol (40 ml) is added dropwise to the mixture at 70° to 80° C. with stirring over the period of 1.5 hours, and after the addition is completed, refluxing is effected for another 2 hours. The reaction solution is concentrated under reduced pressure, and 300 ml of water is added to the residue, followed by extraction with 300 ml of ethyl acetate. The extract is washed with 50 ml of 1 N hydrochloric acid and 50 ml of water successively, dried over anhydrous magnesium sulfate and concentrated under reduced pressure to give 23 g of 5-(1-benzyloxycarbonyl-4-piperidyl)pentanol as a colorless oily material.

IR$\nu_{max}^{neat}$cm$^{-1}$: 3400(OH), 1690(C=O).

NMR spectrum (in CDCl$_3$)δ: 7.3(5H), 5.1(2H), 3.9–4.4(2H), 3.5–3.8(2H), 2.4–3.0(3H), 1.0–1.9(13H).

EXAMPLE 117

A mixture of 18 g of 5-(1-benzyloxycarbonyl-4-piperidy)pentanol and 150 ml of pyridine is stirred under ice-cooling, and 14.6 g of tosyl chloride is added portionwise to the mixture over the period of 30 minutes. After stirring for another 1 hour under ice-cooling, 2 ml of ice-cold water is added dropwise. Ethyl acetate (500 ml) is added to the reaction solution, which is then washed with 500 ml of 2 N-hydrochloric acid and 500 ml of 1 N hydrochloric acid successively, further with dilute aqueous sodium hydrogen-carbonate solution and water successively, dried over anhydrous magnesium sulfate and concentrated under reduced pressure. The resulting oily material is purified by silica-gel column chromatography to give 18 g of 5-(1-benzyloxycarbonyl-4-piperidyl)pentyl p-toluenesulfonate as an oily material.

IR$\nu_{max}^{neat}$cm$^{-1}$: 1700(C=O).

EXAMPLE 118

In 80 ml of ethanol is dissolved 0.95 g of sodium, and 7.2 g of diethyl malonate is added to the solution, followed by stirring. 5-(1-Benzyloxycarbonyl-4-piperidyl)pentyl p-toluenesulfonate (13.7 g) is added to the mixture, followed by refluxing with stirring for 2 hours. Further, a mixture of 0.25 g of sodium, 25 ml of ethanol and 1.8 g of diethyl malonate is added, and the reaction solution is refluxed with stirring for 2 hours. Ethanol is evaporated off under reduced pressure, and 200 ml of water is added to the residue, which is then extracted with 300 ml of ethyl acetate. The extract is dried over anhydrous magnesium sulfate and concentrated under reduced pressure to give ethyl 7-(1-benzyloxycarbonyl-4-piperidyl)-2-ethoxycarbonylheptanoate as an oily material. This product is dissolved in 30 ml of ethanol, and a solution of 6 g of sodium hydroxide in 50 ml of water is added dropwise to the solution with stirring. After the addition is completed, 150 ml of water is added to the reaction solution, which is then extracted with a mixture of ether and petroleum ether (1:1, 150 ml). The aqueous layer is made acidic with conc. hydrochloric acid and extracted with 300 ml of ethyl acetate, and the extract is washed with water, dried over anhydrous magnesium sulfate and concentrated under reduced pressure to give 7-(1-benzyloxycarbonyl-4-piperidyl)-2-carboxyheptanoic acid as an oily material. This product is heated at 160° to 165° C. with stirring for 1 hour, and the resulting oily material is purified by silica-gel column chromatography (hexane:ethyl acetate=3:1 to 1:1) to give 6.4 g of 7-(1-benzyloxycarbonyl-4-piperidyl)heptanoic acid as an oily material.

IR$\nu_{max}^{neat}$cm$^{-1}$: 1730, 1710(C=O).

EXAMPLE 119

A mixture of 6.4 g of 7-(1-benzyloxycarbonyl-4-piperidyl)heptanoic acid, 3.1 g of sodium hydrogencarbonate, 8.6 g of ethyl iodide and 20 ml of N,N-dimethylformamide is heated at 100° C. with stirring for 3 hours. Further, 2.9 g of ethyl iodide and 1 g of sodium hydrogencarbonate are added to the reaction solution, followed by heating at 100° C. for 2.5 hours. After cooling, 200 ml of water is added to the reaction solution, and the mixture is extracted with 300 ml of ethyl acetate. The extract is washed with water, 0.1 N hydrochloric acid and dilute aqueous sodium hydrogen-carbonate solution successively, dried over anhydrous magnesium sulfate and concentrated under reduced pressure to give 5 g of ethyl 7-(1-benzyloxycarbonyl-4piperidyl)heptanoate as an oily material.

IR$\nu_{max}^{neat}$cm$^{-1}$: 1730, 1700(C=O ).

NMR spectrum (in CDCl$_3$)δ: 7.3(5H), 5.1(2H), 4.0–4.3(4H), 2.5–3.0(2H), 2.1–2.4(2H), 1.0–1.9(18H).

EXAMPLE 120

In 30 ml of ethanol is dissolved 0.48 g of sodium, and 6.5 g of ethyl -7-(1-benzyloxycarbonyl-4-piperidyl)heptanoate and 3 g of diethyl oxalate are added to the solution, followed by evaporation under reduced pressure at 60° to 70° C. for 1 hour to remove a low-boiling substance. After cooling, 150 ml of water is added to the resulting viscous material, and the mixture is made acidic with hydrochloric acid and extracted with 300 ml of ethyl acetate. The extract is dried over anhydrous magnesium sulfate and concentrated under reduced pressure. Dimethylsulfoxide (54 ml), 6 ml of water and 1 g of lithium chloride are added to the resulting oily material, followed by stirring at 140° C. for 1 hour. After cooling, 150 ml of water is added to the reaction solution, and the mixture is extracted with 300 ml of ethyl acetate. The extract is washed with water, dried over anhydrous magnesium sulfate and concentrated under reduced pressure to give 6 g of ethyl 8-(1-benzyloxycarbonyl-4-piperidyl)-2-oxooctanoate as an oily material.

IR$\nu_{max}^{neat}$cm$^{-1}$: 1730, 1700(C=O).

Mass spectrum (m/e): 403 (M+).

EXAMPLE 121

A mixture of 13.2 g of 4-(3,4,5,6-tetrahydro-2H-pyrane)carbaldehyde, 44 g of ethyl (triphenylphosphoranilidene)acetate and 200 ml of toluene is stirred at 100° C. for 3 hours. Toluene is evaporated off under reduced pressure, and 200 ml of petroleum ether is added. The insoluble matter is removed by filtration, and the filtrate is concentrated under reduced pressure. The residue is distilled under vacuum to give 17 g of ethyl 3-(3,4,5,6-tetrahydro-2H-pyran-4-yl)acrylate (bp 132-134°/16 mmHg) as an oily material.

IR$\nu_{max}^{neat}$cm$^{-1}$: 1720(C=O), 1650(C=C).

NMR (in CDCl$_3$)δ: 6.6–7.1(1H), 5.6–6.9(1H), 3.7–4.4(4H), 3.2–3.7(2H), 2.0–2.7(1H), 1.1–1.9(7H).

EXAMPLE 122

In 200 ml of ethanol is dissolved 17 g of ethyl 3-(3,4,5,6-tetrahydro-2H-pyran -4-yl)acrylate, and a catalytic reduction reaction is carried out at ordinary temperature and at atmospheric pressure using 4 g of 10% palladium-carbon (50% in water) as a catalyst. After absorption of hydrogen stops, the catalyst is removed by filtration, and the filtrate is concentrated under reduced pressure. The residue is distilled under vacuum to give 15 g (bp 121–123°/16 mmHg)of ethyl 3-(3,4,5,6-tetrahydro-2H-pyran -4-yl)propionate as an oily material.

IR$\nu_{max}^{neat}$cm$^{-1}$: 1740(C=O).

NMR (in CDCl$_3$)δ: 3.7–4.4(4H), 3.0–3.7(2H), 2.1–2.7(2H), 1.0–1.9(10H).

EXAMPLE 123

A solution of 10.2 ml of oxalyl chloride in 200 ml of methylene chloride is cooled to −65° C., and a solution of 18.2 ml of dimethylsulfoxide in 50 ml of methylene chloride is added dropwise over the period of 10 minutes, followed by stirring for 10 minutes. A solution of 14.1 g of 4-thianylmethanol in 100 ml of methylene chloride is added dropwise over the period of 10 minutes, followed by stirring for 20 minutes, and 74 ml of triethylamine is added dropwise over the period of 10 minutes, followed by stirring for 15 minutes. After a cooling bath is removed and stirring is effected at room temperature for 10 minutes, 215 ml of 3 N hydrochloric acid is added, followed by stirring at room temperature for another 1 hour. The methylene chloride layer is separated, washed with water, dried over anhydrous magnesium sulfate and concentrated under reduced pressure to give 11 g of 4-thianylcarbaldehyde as a pale yellow liquid.

IR$\nu_{max}^{neat}$cm$^{-1}$: 1730(C=O).

NMR(in CDCl$_3$)$\delta$: 9.5(1H), 3.0–4.5(1H), 2.5–3.0(4H), 1.0–2.5(4H).

EXAMPLE 124

A mixture of 11 g of 4-thianylcarbaldehyde, 32.3 g of ethyl (triphenylphosphoranilidene)acetate and 200 ml of toluene is stirred at 100° C. for 4 hours. Toluene is evaporated off under reduced pressure, and 200 ml of petroleum ether is added. The insoluble matter is removed by filtration, and the filtrate is concentrated under reduced pressure. The residue is distilled under vacuum to give 10.4 g (bp 155°–157° C./15 mmHg of ethyl 3-(4-thianyl)acrylate as an oily material.

IR$\nu_{max}^{neat}$cm$^{-1}$: 1720(C=O), 1650(C=C).

NMR (in CDCl$_3$)$\delta$: 6.6–7.1(1H), 5.6–6.0(1H), 4.0–4.4(2H), 2.6–2.9(4H), 1.5–2.4(5H), 1.2–1.5(3H).

EXAMPLE 125

In 150 ml of ethanol is dissolved 10 g of ethyl 3-(4-thianyl)acrylate, and a catalytic reduction reaction is carried out at ordinary temperature and at atmospheric pressure using 9 g of 10% palladium-carbon (50% in water) as a catalyst. The reaction mixture is stirred at room temperature for 20 minutes and at 50° C. for 8 hours, and the catalyst is removed by filtration. Nine (9) g of 10% palladium-carbon (50% in water) is added anew to the filtrate, followed by stirring at 50° C. for one day. The catalyst is removed by filtration, and the filtrate is concentrated under reduced pressure to give 9.1 g of ethyl 3-(4-thianyl)propionate as an oily material.

IR$\nu_{max}^{neat}$cm$^{-1}$:1740(C=O).

NMR(in CDCl$_3$)$\delta$: 3.9–4.3(2H), 2.4–2.8(4H), 1.8–2.4(4H), 1.0–1.8(8H).

EXAMPLE 126

A mixture of tert-butyl 3(R)-amino-4-oxo-2,3,4,5-tetrahydro-1,5-benzothiazepine-5-acetate (3.0 g), acetonitrile (100 ml), ethyl 6-(1-benzyloxycarbonyl-4-piperidyl)-2-chlorohexanoate (4.0 g), triethylamine (1.0 g) and potassium iodide (1.6 g) is stirred for 3 days at 80° C. Ethyl 6-(1-benzyloxycarbonyl-4-piperidyl)-2-chlorohexanoate (2.0 g) and potassium iodide (0.8 g) are added, and the stirring is continued for further 1 day at 80° C. The mixture is concentrated in vacuo, diluted with water (100 ml) and extracted with ethyl acetate (300 ml). The extract is washed with water, dried over anhydrous magnesium sulfate and evaporated in vacuo. Purification of the residual oil by silicagel column chromatography (hexane:ethyl acetate=2:1) gives tert-butyl 3(R)-[5-(1-benzyloxy-carbonyl-4-piperidyl)-1(R)-ethoxycarbonylpentyl]amino-4-oxo-2,3,4,5-tetrahydro-1,5-benzoth iazepine-5-acetate (3.1 g) as a colorless oil and tert-butyl 3(R)-[5-(1-benzyloxy-carbonyl-4-piperidyl)-1(S)-ethoxycarbonylpentyl]amino-4-oxo-2,3,4,5-tetrahydro-1,5-benzothiazepine-5-acetate (2.1 g) as a colorless oil.

EXAMPLE 127

To a stirred solution of ethyl 6-(1-benzyloxy-carbonyl-4-piperidyl)-2-hydroxyhexanoate (5 g) in methanol (10 ml) is added dropwise a solution of sodium hydroxide (2.6 g) in water (20 ml) at room temperature. After completing addition, the mixture is stirred for 30 minutes, diluted with water (300 ml) and extracted with ethyl ether (50 ml). The aqueous layer is acidified with concentrated hydrochloric acid and extracted with: ethyl acetate (200 ml). The extract is washed with water, dried over anhydrous magnesium sulfate and evaporated in vacuo to give 6-(1-benzyloxycarbonyl-4-piperidyl)-2-hydroxyhexanoic acid (3.5 g) as a colorless oil.

IR$\nu_{max}^{neat}$cm$^{-1}$: 3400 (OH), 1670 (C=O).

EXAMPLE 128

To a stirred solution of ethyl 6-(1-benzyloxycarbonyl-4-piperidyl)-2-hydroxyhexanoate (1.0 g) in pyridine (10 ml) is added dropwise methanesulfonyl chloride (0.92 g) at ice-bath temperature. After stirring for 1 hour at ice-bath temperature, the mixture is stirred for 30 minutes at room temperature, and then cooled. After addition of water (1 ml), the mixture is stirred for 30 minutes at ice-bath temperature, and ice bath is removed. The mixture is stirred for 30 minutes at room temperature, diluted with water (50 ml) and extracted with ethyl acetate (50 ml). The extract is washed successively with 10% hydrochloric acid, water, 0.1N sodium hydroxide solution and water, dried over anhydrous magnesium sulfate and evaporated in vacuo to yield ethyl 6-(1-benzyloxycarbonyl-4-piperidyl)-2-methanesulfonyloxyhexanoate (1.1 g) as a colorless oil.

IR$\nu_{max}^{neat}$cm$^{-1}$: 1750, 1690 (C=O).

NMR spectrum (in CDCl$_3$)$\delta$: 7.3 (5H), 4.9–5.1 (3H), 3.9–4.5 (4H), 3.1 (3H), 1.0–3.1 (18H).

EXAMPLE 129

A mixture of tert-butyl 3(R)-amino-4-oxo-2,3,4,5-tetrahydro-1,5-benzothiazepine-5-acetate (2.05 g) and ethyl 6-(1-benzyloxycarbonyl-4-piperidyl)-2-methanesulfonyloxyhexanoate (1.5 g) is heated at 90° C. for 1 day. After cooling, ethyl acetate (300 ml) is added to the mixture, and the resulting solution is washed with 5% phosphoric acid solution (30 ml×2) and water (20 ml) successively. The organic layer is dried over anhydrous magnesium sulfate and evaporated in vacuo to yield an oily residue, which is purified by silicagel column chromatography (hexane:ethyl acetate=2:1) to give tert-butyl 3(R)-[5-(1-benzyloxy- carbonyl-4-piperidyl)-1(R)-ethoxycarbonylpentyl]amino-4-oxo-2,3,4,5-tetrahydro-1,5-benzothiazepine-5-acetate (0.7 g) as a colorless oil. From the subsequent fraction, tert-butyl 3(R)-[5-(1-benzyloxycarbonyl-4-piperidyl)-1(S)-ethoxycarbonylpentyl]amino-4-oxo-2,3,4,5-tetrahydro-1,5-benzothiazepine-5-acetate (0.55 g) is obtained as a colorless oil.

EXAMPLE 130

6-(1-Benzyloxycarbonyl-4-piperidyl)-2-hydroxyhexanoic acid (4.7 g) and quinine (4.4 g) are dissolved in hot acetone (150 ml). After removal of the insoluble substance by filtration, the solution is allowed to stand in a refrigerator. The precipitating crystals are collected by filtration and recrystallized three times from acetone to yield quinine salt (1.9 g) as colorless crystals. This salt (1.2 g) is added to a mixture of ethyl acetate (200 ml) and 1 N hydrochloric acid (50 ml), and the resulting mixture is agitated throughly. The ethyl acetate layer is washed with 1 N hydrochloric acid (30 ml, 20 ml) and water successively, dried over anhydrous magnesium sulfate and evaporated in vacuo. To the oily residue (0.6 g) are added toluene (50 ml), ethanol (10 ml) and p-toluenesufonic acid (0.05 g). The resulting mixture is stirred for 3 hours at 100° C., cooled, diluted with ethyl acetate, washed with water (50 ml×2) and dried over anhydrous magnesium sulfate. Evaporation of the solvent gives ethyl ester (0.6 g) as a colorless oil, which is dissolved in pyridine (5 ml). To the stirred solution is added dropwise methane-sulfonyl chloride (0.5 ml) at ice-bath temperature. After stirring for 2 hours at ice-bath temperature, the mixture is stirred at room temperature for 30 minutes and cooled again by ice-bath. Water (0.5 ml) is added and the mixture is stirred at ice-bath temperature for 30 minutes and then at room temperature for 30 minutes. The mixture is diluted with water (20 ml) and extracted with ethyl acetate (50 ml). The extract is washed by 10% hydrochloric acid, water, 0.1 N sodium hydroxide solution and water successively, dried over anhydrous magnesium sulfate and evaporated in vacuo to yield ethyl 6-(1-benzyloxycarbonyl-4-piperidyl)-2-methanesulfonyloxyhexanoate(0.6 g: $[\alpha]_D$ —12.8° in methanol) as a colorless oil. The mixture of this sulfonate (0.5 g) and tert-butyl 3(R)-amino-4-oxo-2,3,4,5-tetrahydro-1,5-benzothiazepine-5-acetate (0.71 g) is heated at 80°–100° C. for 1 day. After cooling, ethyl acetate (200 ml) is added, and the resulting solution is washed with 5% phosphoric acid solution (30 ml, 20 ml) and water successively, dried over anhydrous magnesium sulfate and evaporated in vacuo to yield a yellow oil, which is purified by silicagel colum chromatography (hexane:ethyl acetate=2:1). From the first fraction is obtained tert-butyl 3(R)-[5-(1-benzyloxycarbonyl-4-piperidyl-1(R)-ethoxycarbonylpentyl]amino-4-oxo-2,3,4,5-tetrahydro-1,5-benzothiazepine-5-acetate (0.45 g) as a colorless oil. From the second fraction, tert-butyl 3(R)-[5-(1-benzyloxycarbonyl-4-piperidyl)-1(S)-ethoxycarbonylpentyl]amino-4-oxo-2,3,4,5-tetrahydro-1,5-benzothiazepine-5-acetate (0.09 g) is obtained as a colorless oil from the second fraction.

EXAMPLE 131

6-(1-Benzyloxycarbonyl-4-piperidyl)-2-hydroxyhexanoic acid (5 g) and cinchonidine (4.2 g) are dissolved in hot acetone (50 ml). After cooling, the solution is diluted with ethyl ether (50 ml) and allowed to stand in a refrigerator. The precipitates are removed by filtration, and the filtrate is concentrated in vacuo. The residue is dissolved in acetone (5 ml) and the resulting solution is diluted with ethyl ether (35 ml). After standing in a refrigerator, the resulting precipitates are collected by filtration to give cinchonidine salt (1.4 g). This salt (1.3 g) is added to a mixture of ethyl acetate (200 ml) and 1 N hydrochloric acid (50 ml), and the resulting mixture is agitated throughly. The ethyl acetate layer is washed with 1 N hydrochloric acid (50 ml) and water (50 ml) successively, dried over anhydrous magnesium sulfate and evaporated in vacuo to yield an oily residue, which is dissolved in a mixture of toluene (30 ml), ethanol (3 ml) and p-toluenesulfonic acid (0.05 g). The solution is stirred for 1 hour at 90°–100° C., cooled, diluted with ethyl acetate (200 ml) and washed with water (50 ml×2). The organic layer is dried over anhydrous magnesium sulfate and evaporated in vacuo to yield the ethyl ester as a colorless oil, which is dissolved in pyridine (5 ml). To the stirred solution is added dropwise methanesulfonyl chloride (0.4 ml) at ice-bath temperature. After stirring for 30 minutes, water (1 ml) is added to the mixture, and the resulting mixture is stirred for 30 minutes at ice-bath temperature and diluted with ethyl acetate (150 ml). The organic layer is washed with 1 N hydrochloric acid (50 ml×2), sodium bicarbonate solution (50 ml) and water successively, dried over anhydrous magnesium sulfate and evaporated in vacuo to give ethyl 6-(1-benzyloxycarbonyl-4-piperidyl)-2-methanesulfonyloxyhexanoate (0.8 g: $[\alpha]_D$ +13.7° in methanol) as a colorless oil. A mixture of this mesylate (0.72 g) and tert-butyl 3(R)-amino-4-oxo-2,3,4,5-tetrahydro-1,5-benzothiazepine-5-acetate (1.46 g) is stirred overnight at 90°–100° C. After cooling, the reaction mixture is dissolved in ethyl acetate (200 ml) and the solution is washed by 5% phosphoric acid solution (30 ml×2) and water successively, dried over anhydrous magnesium sulfate and evaporated in vacuo to give a yellow oil, which is purified by silica gel column chromatography (hexane:ethyl acetate=2:1). t-Butyl 3(R)-[5-(1-benzyloxycarbonyl-4-piperidyl)-1(R)-ethoxycarbonylpentyl]amino-4-oxo-2,3,4,5-tetrahydro-1,5-benzothiazepine-5-acetate (0.12 g) is obtained as a colorless oil from the first fraction. The second fraction gives t-butyl 3(R)-[5-(1-benzyloxycarbonyl-4-piperidyl)-1(S)-ethoxycarbonylpentyl]amino-4-oxo-2,3,4,5-tetrahydro1,5-benzothiazepine-5-acetate (0.52 g) as a colorless oil.

EXAMPLE 132

A mixture of 3(R)-phthalimido-2,3-dihydro-1,5-(5H)-benzothiazepin-4-one (10 g), ethanol (500 ml) and hydrazine hydrate (6.2 g) is refluxed for 1 hour. After ethanol is removed by evaporation under reduced pressure, water (300 ml) is added, and the mixture is extracted with ethyl acetate (400 ml). The extract is washed with 0.1 N sodium hydroxide solution (100 ml×2) and water (100 ml) successively, dried over anhydrous magnesium sulfate and concentrated in vacuo to give 3(R)-amino-2,3-dihydro-1,5(5H)-benzothiazepin-4-one (3.75 g) as colorless leaflets.

mp. 170°–173° C.

$[\alpha]_D$ —367° (in methanol).

Elemental analysis for $C_9H_{10}N_2OS$. Calcd: C,55.65; H,5.19; N,14.42. Found: C,55.73; H,5.09; N,14.51.

EXAMPLE 133

A mixture of 3(R)-amino-2,3-dihydro-1,5-(5H)-benzothiazepin-4-one (1.0 g), ethyl 6-(1-benzyloxycarbonyl-4-piperidyl)-2-oxohexanoate (6.0 g), acetic acid (0.37 g), molecular sieves 3A (3.0 g) and ethanol (25 ml) is stirred at room temperature for 20 minutes. To the stirred mixture is added dropwise a solution of sodium cyanoborohydride (0.66 g) in ethanol (20 ml) over a period of 5 hours. After the reaction mixture is concentrated under reduced pressure, the residue is diluted with a mixture of ethyl acetate (80 ml) and water (100 ml). After the insoluble substance is removed by filtration, the ethyl acetate layer is washed with diluted hydrochloric acid, water and sodium bicarbonate solution successively, dried over anhydrous sodium sulfate and concentrated in vacuo. The residue is purified by silica gel column chromatography (hexane:ethyl acetate=2:1) to yield 3(R)-[5-(1-benzyl-oxycarbonyl-4-piperidyl)-1-ethoxycarbonylpentyl]amino-2,3-dihydro-1,5(5H)-benzothiazepin-4-one (1.1 g) as a colorless oil.

$IR\nu_{max}^{neat}cm^{-1}$: 3230 (NH); 1730, 1700, 1680 (C=O).

NMR (in CDCl$_3$)δ: 7.3(5H), 7.0–7.7(4H), 5.1(2H), 3.9–4.3(5H), 2.4–3.7(7H), 1.0–1.8(16H).

Mass spectrum (m/e): 553 (M+).

EXAMPLE 134

A mixture of 3(R)-amino-2,3-dihydro-1,5(5H)-benzothiazepin-4-one (2.7 g) and ethyl 6-(1-benzyloxycarbonyl-4-piperidyl)-2-methanesulfonyloxyhexanoate (5.4 g) is heated at 100°–130° C. for 3 hours. After cooling, the mixture is dissolved in ethylacetate (200 ml) and the solution is washed with water, dried over anhydrous magnesium sulfate and concentrated in vacuo. The residue is purified by silica gel column chromatography (hexane:ethyl acetate=2:1) to give 3(R)-[5-(1-benzyloxycarbonyl-4-piperidyl)-1-ethoxycarbonylpentyl]amino-2,3-dihydro-1,5(5H)-benzothiazepin-4-one (2.9 g) as a colorless oil.

EXAMPLE 135

A mixture of 3(R)-[5-(1-benzyloxycarbonyl-4-piperidyl)-1-ethoxycarbonylpentyl]amino-2,3-dihydro-1,5(5H)-benzothiazepin-4-one (1.0 g), tert-butyl chloroacetate (0.27 g), potassium iodide (0.3 g), potassium carbonate (0.24 g) and N,N-dimethylformamide (10 ml) is stirred for 15 hours at room temperature. The mixture is poured into water (50 ml) and extracted with ethyl acetate (40 ml). The extract is washed with diluted hydrochloric acid, sodium bicarbonate solution and water successively, dried over anhydrous sodium sulfate and concentrated in vacuo. The residue is purified by silica gel column chromatography (hexane:ethyl acetate=2:1) to give firstly tert-butyl 3(R)-[5-(1-benzyloxycarbonyl-4-piperidyl)-1(R)-ethoxycarbonylpentyl]amino-4-oxo-2,3,4,5-tetrahydro-1,5-benzothiazepine-5-acetate (0.45 g) as a colorless oil.

From the second fraction is obtained tert-butyl 3(R)-[5-(1-benzyloxycarbonyl-4-piperidyl)-1(S)-ethoxycarbonylpentyl]amino-4-oxo-2,3,4,5-tetrahydro-1,5-benzothiazepine-5-acetate (0.42 g) as a colorless oil.

EXAMPLE 136

In 10 ml of acetic acid is dissolved 5.2 g of tert-butyl 3(R)-[5-(1-benzyloxycarbonylpiperidyl)-1(S)-ethoxycarbonylpentyl]amino-4-oxo-2,3,4,5-tetrahydro-1,5-benzothiazepine-5-acetate, and 10 ml of 30% hydrogen bromide-acetic acid is added to the solution. After the mixture is left standing at room temperature for 1.5 hours, 200 ml of ethyl ether is added to the mixture and the resulting mixture is left standing. The supernatant liquid is removed by decantation and the precipitate is dissolved in 90 ml of 1 N aqueous sodium hydroxide solution. After the mixture is left standing at room temperature for 1.5 hours, the mixture is neutralized with 10 ml of acetic acid and purified by MCI gel column chromatography (water:methanol=1:1). The eluate is concentrated under reduced pressure to a volume of about 10 ml, and the deposited crystals are collected by filtration and dried to give 2.1 g of 3(R)-[1(S)-carboxy-5-(4-piperidyl) pentyl]amino-4-oxo-2,3,4,5-tetrahydro-1,5-benzothiazepine-5-acetic acid as a colorless crystalline powder, melting at a temperature higher than 270° C. (decomposition).

$[\alpha]_D$ −130° (in water).

Elemental analysis for C$_{22}$H$_{31}$N$_3$O$_5$S. Calcd.: C, 58.78; H, 6.95; N, 9.35. Found: C, 58.59; H, 6.99; N, 9.37.

$IR\nu_{max}^{KBr}cm^{-1}$: 1670 (amide), 1635, 1610 (carboxylate).

EXAMPLE 137

To a mixture of 5.4 g of 9-phthalimidononanoic acid, 1.1 g of red phosphorus and 25 ml of carbon tetrachloride is added 2.8 ml of bromine dropwise for the period of 30 minutes and the mixture is stirred for 15 minutes. Further, 2.8 ml of bromine is added dropwise for the period of 15 minutes and the resulting mixture is heated at 80° C. for 30 minutes and at 100° C. for 4.5 hours. After cooling, the mixture is poured into 150 ml of water and extracted with 150 ml of ether. The ether layer is extracted with 350 ml of saturated sodium bicarbonate solution and the aqueous layer is acidified with conc. hydrochloric acid. The deposited crystals are collected by filtration, washed with water and dried to give 6.8 g of 2-bromo-9-phthalimidononanoic acid, melting at 97°–98° C. (recrystallized from petroleum ether and ether).

$IR\nu_{max}^{KBr}cm^{-1}$: 1770, 1710 (C=O).

EXAMPLE 138

In 50 ml of ethanol is dissolved 6.8 g of 2-bromo-9-phthalimidononanoic acid, and 5 ml of conc. sulfuric acid is added to the solution. After the solution is left standing overnight, the solution is diluted with 100 ml of water and extracted with 200 ml of ethyl acetate. The ethyl acetate layer is washed with 50 ml of aqueous sodium bicarbonate solution and 50 ml of water, dried over anhydrous magnesium sulfate and concentrated under reduced pressure. The resulting oily substance is purified by silicagel column chromatography (hexane:ethyl acetate=6:1) to give 6.3 g of ethyl 2-bromo-9-phthalimidononanoate as a colorless oil.

$IR\nu_{max}^{neat}cm^{-1}$: 1770, 1735, 1710 (C=O).

NMR (in CDCl$_3$)δ: 7.6–8.1(m,4H), 4.1–4.5(m,3H), 3.6–4.0 (t,2H), 1.4(t,3H), 1.2–2.4(m,12H).

EXAMPLE 139

In 100 ml of acetonitrile are dissolved 2 g of tert-butyl 3(R)-amino-4-oxo-2,3,4,5-tetrahydro-1,5-benzothiazepine-5-acetate and 7.4 g of ethyl 2-bromo-7-phthalimidoheptanoate, and 0.85 g of triethylamine is added to the solution. After the mixture is heated at 80°–100° C. for 2 days, the mixture is concentrated under reduced pressure, diluted with 100 ml of water and extracted with 200 ml of ethyl acetate. The ethyl acetate layer is dried over anhydrous magnesium sulfate and concentrated under reduced pressure. The resulting oily substance is separated and purified by silicagel column chromatography (hexane:ethyl acetate=2:1) to give from the first fraction 1.0 g of tert-butyl 3(R)-[1(R)-ethoxycarbonyl6-phthalimidohexyl]amino-4-oxo-2,3,4,5-tetrahydro-1,5-benzothiazepine-5-acetate as a colorless oil.

$IR\nu_{max}^{neat}cm^{-1}$: 3320(NH); 1770, 1730, 1710, 1680 (C=O).

$[\alpha]_D$ −95° in methanol).

Mass spectrum (m/e): 609 (M+).

From the second fraction, 1.15 g of tert-butyl 3(R)-[1(S)-ethoxycarbonyl-6-phthalimidohexyl]amino-4-oxo-2,3,4,5-tetrahydro-1,5-benzothiazepine-5-acetate is obtained as a colorless oil.

$IR\nu_{max}^{neat}cm^{-1}$: 3320 (NH); 1770, 1740, 1700, 1670 (C=O).

$[\alpha]_D$ −125° (in methanol).

Mass spectrum (m/e): 609 (M+).

EXAMPLE 140

In 5 ml of 5 N hydrogen chloride-ethyl acetate solution is dissolved 0.12 g of tert-butyl 3(R)-[1(S)-ethoxycarbonyl-6-phthalimidohexyl]amino-4-oxo-2,3,4,5-tetrahydro-1,5-benzothiazepine -5-acetate, and the solution is left standing at room temperature for 1 hour. Petroleum ether (50 ml) is added to the solution and the deposited precipitate is dried under reduced pressure to give 0.1 g of 3(R)-[1(S)-ethoxycarbonyl-6-phthalimidohexyl]amino-4-oxo-2,3,4,5-tetrahydro-1,5-benzothiazepine-5-acetic acid hydrochloride as a colorless powder.

$[\alpha]_D - 109°$ (in methanol).

Elemental analysis for $C_{28}H_{31}N_3O_7S \cdot HCl \cdot H_2O$. Calcd.: C, 55.30; H, 5.64; N, 6.91. Found : C, 55.65; H, 5.72; N, 6.95.

EXAMPLE 141

In 100 ml of acetonitrile are dissolved 2.0 g of tert-butyl 3(R)-amino-4-oxo-2,3,4,5-tetrahydro-1,5-benzothiazepine-5-acetate and 3.0 g of ethyl 2-bromo-9-phthalimidononanoate, and 0.85 g of triethylamine is added to the solution. The mixture is heated at 80° C. for 3 days, concentrated under reduced pressure, diluted with 100 ml of water and extracted with 150 ml of ethyl acetate. The ethyl acetate layer is dried over anhydrous magnesium sulfate and concentrated under reduced pressure. The resulting oily substance is separated and purified by silicagel column chromatography (hexane:ethyl acetate=3:1 - 2:1) to give from the first fraction 0.9 g of tert-butyl 3(R)-[1(R)-ethoxycarbonyl-8-phthalimidooctyl]amino-4-oxo-2,3,4,5-tetrahydro-1,5-benzothiazepine-5-acetate as a colorless oil.

$IR\nu_{max}^{neat}cm^{-1}$: 3340 (NH); 1775, 1740, 1710, 1680 (C=O).

$[\alpha]_D - 111°$ (in methanol).

Mass spectrum (m/e): 637 (M+).

From the second fraction, 1.1 g of tert-butyl 3(R)[1(S)-ethoxycarbonyl-8-phthalimidooctyl]amino-4-oxo-2,3,4,5-tetrahydro-1,5-benzothiazepine-5-acetate is obtained as a colorless oil.

$IR\nu_{max}^{neat}cm^{-1}$: 3330 (NH); 1770, 1735, 1710, 1665 (C=O).

$[\alpha]_D - 117°$ (in methanol).

Mass spectrum (m/e): 637 (M+).

EXAMPLE 142

In 100 ml of acetonitrile are dissolved 1.7 g of tert-butyl 3(R)-amino-4-oxo-2,3,4,5-tetrahydro-1,5-benzothiazepine-5-acetate and 2.4 g of ethyl 2-bromo-10-phthalimidodecanoate, and 0.75 g of triethylamine is added to the solution. The mixture is heated at 80° C. for 3 days, concentrated under reduced pressure, diluted with 100 ml of water and extracted with 150 ml of ethyl acetate. The ethyl acetate layer is dried over anhydrous magnesium sulfate and concentrated under reduced pressure. The resulting oily substance is separated and purified by silicagel column chromatography (hexane:ethyl acetate=3:1 - 2:1) to give from the first fraction 0.9 g of tert-butyl 3(R)-[1(R)-ethoxycarbonyl-9-phthalimidononyl]amino-4-oxo-2,3,4,5-tetrahydro-1,5-benzothiazepine-5-acetate as a colorless oil.

$IR\nu_{max}^{neat}cm^{-1}$: 3330 (NH); 1770, 1740, 1715, 1680 (C=O).

$[\alpha]_D - 102°$ (in methanol).

Mass spectrum (m/e): 651 (M+).

From the second fraction, 0.95 g of tert-butyl 3(R)-[1(S)-ethoxycarbonyl-9-phthalimidononyl]amino-4-oxo-2,3,4,5-tetrahydro-1,5-benzothiazepine-5-acetate as a colorless oil.

$IR\nu_{max}^{neat}cm^{-1}$: 3330 (NH); 1770, 1740, 1710, 1670 (C=O).

$[\alpha]_D - 117°$ (in methanol).

Mass spectrum (m/e): 651 (M+).

EXAMPLE 143

In 5 ml of 5 N hydrogen chloride-ethyl acetate solution is dissolved 0.12 g of tert-butyl 3(R)-[1(S)-ethoxycarbonyl-8-phthalimidooctyl]amino-4-oxo-2,3,4,5-tetrahydro-1,5-benzothiazepine-5-acetate, and the solution is left standing at room temperature for 3 hours. Petroleum ether (70 ml) is added to the solution and the deposited precipitate is dried under reduced pressure to give 0.10 g of 3(R)-[1(S)-ethoxycarbonyl-8-phthalimidooctyl]amino-4-oxo-2,3,4,5-tetrahydro-1,5-benzothiazepine-5-acetic acid hydrochloride as a colorless powder.

$[\alpha]_D - 108°$ (in methanol).

Elemental analysis for $C_{30}H_{35}N_3O_7S \cdot HCl$. Calcd.: C, 58.29; H, 5.87; N, 6.80. Found : C, 57.98; H, 5.90; N, 6.60.

EXAMPLE 144

In 5 ml of 5 N hydrogen chloride-ethyl acetate solution is dissolved 0.1 g of 3(R)-[1(S)-ethoxycarbonyl-9-phthalimidononyl]amino-4-oxo-2,3,4,5-tetrahydro-1,5-benzothiazepine-5-acetate, and the solution is left standing at room temperature for 3 hours. Petroleum ether (50 ml) is added to the solution and the deposited precipitate is dried under reduced pressure to give 0.076 g of 3(R)-[1(S)-ethoxycarbonyl-9-phthalimidononyl]amino-4-oxo-2,3,4,5-tetrahydro-1,5-benzothiazepine-5acetic acid hydrochloride as a colorless powder.

$[\alpha]_D - 105°$ (in methanol).

Elemental analysis for $C_{31}H_{37}N_3O_7S \cdot HCl \cdot \frac{1}{2}H_2O$. Calcd.: C, 58.07; H, 6.13; N, 6.55. Found : C, 58.26; H, 6.31; N, 6.34.

EXAMPLE 145

In 10 ml of ethanol is dissolved 0.9 g of tert-butyl 3(R)-[1(S)-ethoxycarbonyl-8-phthalimidooctyl]amino-4-oxo-2,3,4,5-tetrahydro-1,5-benzothiazepine-5-acetate, and 0.35 g of hydrazine hydrate is added to the solution. After the mixture is left standing at room temperature overnight, the mixture is concentrated under reduced pressure, diluted with water and extracted four times with 50 ml of ethyl acetate. Water (50 ml) and 1.0 g of sodium bicarbonate are added to the ethyl acetate layer, and 0.46 g of di-tertbutyl dicarbonate is added to the resulting mixture with stirring. After the mixture is stirred at room temperature for 30 minutes, the ethyl acetate layer is dried over anhydrous magnesium sulfate and concentrated under reduced pressure. The residue is purified by silicagel column chromatography (hexane:ethyl acetate=2:1) to give 0.79 g of tert-butyl 3(R)-[8-tert-butoxycarbonylamino-1(S)-ethoxycarbonyloctyl]amino-4-oxo-2,3,4,5-tetrahydro-1,5-benzothiazepine-5-acetate as a colorless oil.

$IR\nu_{max}^{neat}cm^{-1}$: 1740, 1710, 1670 (C=O).

$[\alpha]_D - 133°$ (in methanol).

Mass spectrum (m/e): 607 (M+).

EXAMPLE 146

In 10 ml of 5 N hydrogen chloride-ethyl acetate solution is dissolved 0.72 g of tert-butyl 3(R)-[8-tert-butoxycarbonylamino-1(S)-ethoxycarbonyloctyl]amino-4-oxo-2,3,4,5-tetrahydro1,5-benzothiazepine-5-acetate, and the solution is left standing at room temperature for 3.5 hours. Ether (10 ml) is added to the solution and the deposited precipitate is dried under reduced pressure to give 0.50 g of 3(R)-[8-amino-1(S)-ethoxycarbonyloctyl]amino-4-oxo-2,3,4,5-tetrahydro-1,5-benzothiazepine-5-acetic acid dihydrochloride as a colorless powder.

$[\alpha]_D$ −125° (in methanol).

Mass spectrum (m/e): 451 (M+).

Elemental analysis for $C_{22}H_{33}N_3O_5S \cdot 2HCL \cdot \frac{1}{2}H_2O$. Calcd.: C, 49.44; H, 6.98; N, 7.86. Found : C, 49.39; H, 6.61; N, 7.73.

EXAMPLE 147

In 10 ml of 1N aqueous sodium hydroxide solution is dissolved 0.35 g of 3(R)-[8-amino-1(S)-ethoxycarbonyloctyl]-amino-4-oxo-2, 3,4,5-tetrahydro-1,5-benzothiazepine-5-acetic acid dihydrochloride, and the solution is left standing at room temperature for 30 minutes. Acetic acid (2.5 ml) is added to the solution and the resulting mixture is purified by Amberlite XAD-2 column chromatography (methanol:water=1:2). The eluate is concentrated under reduced pressure and lyophilized to give 0.24 g of 3(R)-[8-amino-1(S)-carboxyoctyl]-amino-4-oxo-2, 3,4,5-tetrahydro-1,5-benzothiazepine-5-acetic acid as a colorless powder.

$[\alpha]_D$ −141° (in methanol).

SIMS spectrum (m/e): 424 (MH+).

EXAMPLE 148

In a mixture of ethanol (40 ml) and water (30 ml) is dissolved S-(o-nitrophenyl)-L-cysteine (0.5g) with heating. After cooling to room temperature, ethyl 6-(1-benzyloxycarbonyl-4-piperidyl)-2-oxohexanoate (2.3 g) is added to the solution. A solution of sodium cyanoborohydride (0.38 g) in ethanol (50 ml) is added dropwise to the mixture over the period of two hours, and the reaction mixture is allowed to stand overnight. The reaction mixture is concentrated under reduced pressure, and ethyl acetate (100 ml) and 1% aqueous phosphoric acid solution (50 ml) are added to the residue, followed by extraction. The ethyl acetate layer is washed with 1% aqueous phosphoric acid solution (50 ml) and water (50 ml), to which hexane (100 ml) and saturated sodium hydrogencarbonate solution (50 ml) are added, followed by agitating. The deposited yellow oil is separated, weakly acidic with 10% hydrochloric acid and extracted with ethyl acetate (200 ml). The extract is dried over anhydrous magnesium sulfate and concentrated under reduced pressure. Ethyl ether is added to the residue to give 2(R)-[5-(1-benzyloxycarbonyl-4-piperidyl)-1-ethoxycarbonylpentyl]amino-3-(o-nitrophenyl)thiopropionic acid (0.6 g) as a yellow powder.

Elemental analysis for $C_{30}H_{39}N_3O_3S \cdot \frac{1}{2}H_2O$. Calcd.: C, 59.00; H, 6.60; N, 6.88. Found : C, 59.06; H, 6.58; N, 7.33.

NMR spectrum δ(DMSO-d6): 7.3–7.6, 7.4, 7.65–7.8, 8.1–8.3(9H, phenyl proton); 5.1(2H, methylene proton of the benzyl group).

EXAMPLE 149

In a mixture of acetic acid (4 ml) and water (2 ml) is dissolved 2(R)-[5-(1-benzyloxycarbonyl-4-piperidyl)-1ethoxycarbonylpentyl]amino-3-(o-nitrophenyl)thiopropionic acid (0.3 g), and powdered zinc (0.3 g) is added to the solution. The reaction mixture is stirred at room temperature for 1 hour, diluted with water (50 ml) and extracted with ethyl acetate (200 ml). The ethyl acetate layer is washed with water, dried over anhydrous magnesium sulfate and concentrated under reduced pressure. To the residue are added ethyl ether (30 ml) and 5N hydrogen chloride-ethyl acetate solution (0.5 ml). The deposited colorless powder is collected by filtration to give 3-(o-aminophenyl)thio-2(R)-[5-(1-benzyloxycarbonyl-4-piperidyl)-1-ethoxycarbonylpentyl]aminopropionic acid dihydrochloride (0.3 g).

NMR spectrum δ(DMSO-d6): 6.8–7.6, 7.4(9H, phenyl proton); 5.1(2H, methylene proton of the benzyl group).

Elemental analysis for $C_{30}H_{41}N_3O_6S \cdot 2HCl \cdot \frac{1}{2}H_2O$. Calcd.: C, 55.12; H, 6.78; N, 6.43. Found: C, 54.82; H, 6.84; N, 6.68.

EXAMPLE 150

In N,N-dimethylformamide (5 ml) is dissolved 3-(o-aminophenyl)thio-2(R)-[5-(1-benzyloxycarbonyl-4-piperidyl)-1-ethoxycarbonylpentyl]aminopropionic acid dihydrochloride (0.16 g), and diethyl phosphorocyanidate (0.3 ml) is added dropwise to the solution. To the mixture is added triethylamine (0.2 ml) and the reaction mixture is stirred under ice-cooling for 1 hour. The reaction mixture is diluted with water (100 ml) and extracted with ethyl acetate (50 ml). The extract is washed with water, dried over anhydrous magnesium sulfate and concentrated under reduced pressure. The residue is purified by silicagel column chromatography (hexane: acetone=2:1) to give 3(R)-[5-(1-benzyloxycarbonyl-4-piperidyl)-1-ethoxycarbonylpentyl]amino-2,3-dihydro-1,5(5H)-benzothiazepin-4-one (0.09 g) as a colorless oil.

IR $\nu_{max}^{neat}$ cm$^{-1}$:3230, 1730, 1700, 1680.

EXAMPLE 151

In 1.2l of 0.1M phosphate buffer (0.1M KH$_2$PO$_4$ 600 ml and 0.1M K$_2$HPO$_4$ 600 ml) are added ethyl 6-(1-benzyloxycarbonyl-4-piperidyl)-2-hydroxyhexanonate (40 g) and Lipase PN (200 mg: Wako Pure Chemicals, Japan), and the mixture is agitated at room temperature for 3.5 hours. The mixture is made acidic with conc. hydrochloric acid and extracted twice with a mixture of ethyl acetate and petroleum ether (2:1). The ethyl acetate layer is washed with saturated sodium hydrogencarbonate and water, dried over anhydrous magnesium sulfate and concentrated under reduced pressure to give R-isomer-rich ethyl 6-(1-benzyloxycarbonyl-4-piperidyl)-2-hydroxyhexanoate (14.6 g) as a colorless oil. The aqueous sodium hydrogencarbonate layer is extracted with ethyl ether, made acidic with conc. hydrochloric acid and extracted with ethyl acetate (500 ml). The ethyl acetate layer is washed with water, dried over anhydrous magnesium sulfate and concentrated under reduced pressure to give S-isomer-rich 6-(1-benzyloxycarbonyl-4-piperidyl)-2-hydroxyhexanoic acid (23.5 g).

In pyridine (30 ml) is dissolved R-isomer-rich ethyl 6-(1-benzyloxycarbonyl-4-piperidyl)-2-hydroxyhexanoate (7 g), and methanesulfonyl chloride (2.9 ml) is added dropwise, with stirring, under ice-cooling over the period of 5 minutes. The mixture is stirred under ice-cooling for 1.5 hours, and water (5 ml) is added dropwise to the mixture. The reaction mixture is stirred for 30 minutes, diluted with ethyl acetate (300 ml) and washed with 1N hydrochloric acid, saturated sodium hydrogencarbonate solution and water. The ethyl acetate layer is dried over anhydrous magnesium sulfate and concentrated under reduced pressure to give R-isomer-rich ethyl 6-(1-benzyloxycarbonyl-4-piperidyl)-2-methanesulfonyloxyhexanoate (8.2 g) as a pale yellow oil.

$[\alpha]_D + 15°$ (in methanol).

EXAMPLE 152

In toluene (50 ml) is dissolved S-isomer-rich 6-(1-benzyloxycarbonyl-4-piperidyl)-2-hydroxyhexanoic acid (3.6 g), and ethanol (10 ml) and p-toluenesulfonic acid (0.2 g) are added to the solution, followed by agitating at 90° C. for 1.5 hours. The mixture is diluted with ethyl acetate (100 ml), washed with saturated sodium hydrogencarbonate solution (100 ml) and water (100 ml), dried over anhydrous magnesium sulfate and concentrated under reduced pressure to give S-isomer-rich ethyl 6-(1-benzyloxycarbonyl-4-piperidyl)-2-hydroxyhexanoate (3.7 g) as an oil. This product (1.0 g) is dissolved in pyridine (5 ml), and methanesulfonyl chloride (0.4 ml) is added dropwise to the solution with stirring over the period of 5 minutes under ice-cooling. After stirring is continued for 15 minutes under ice-cooling, water (3 ml) is added to the mixture, followed by stirring for 30 minutes. Ethyl acetate (150 ml) is added to the mixture, and the resulting mixture is washed with 1N hydrochloric acid (50 ml ×2), saturated sodium hydrogencarbonate solution (50 ml) and water (50 ml). The ethyl acetate layer is dried over anhydrous magnesium sulfate and concentrated under reduced pressure to give S-isomer-rich 6-(1-benzyloxycarbonyl-4-piperidyl)-2-methanesulfonyloxyhexanoate [1.2 g : $[\alpha]_D - 16.6°$ (in methanol)] as a pale yellow oil. This product (1.2 g) and cesium propionate [prepared from cesium carbonate (0.47 g) and propionic acid (0.32 g)] are added to N,N-dimethylformamide (30 ml), and the mixture is stirred at 90° C. for 1 hour. After cooling, ethyl acetate (150 ml) is added to the mixture, and the mixture is washed with 0.1N hydrochloric acid (50 ml ×2), sodium hydrogencarbonate solution (50 ml) and water (50 ml), dried over anhydrous magnesium sulfate and concentrated under reduced pressure. The obtained oily product is purified by silica gel column chromatography (hexane-ethyl acetate=3:1) to give R-isomer-rich ethyl 6-(1-benzyloxycarbonyl-4-piperidyl)-2-propionyloxylhexanoate (1.07 g) as a colorless oil. This product (1.05 g) is dissolved in ethanol (10 ml), and 1N aqueous sodium hydroxide solution (10 ml) is added dropwise to the solution over the period of 5 minutes, followed by agitating for 30 minutes. The mixture is made acidic with conc. hydrochloric acid and extracted with ethyl acetate (100 ml). The ethyl acetate layer is washed with water, dried over anhydrous magnesium sulfate and concentrated under reduced pressure to give R-isomer-rich 6-(1-benzyloxycarbonyl-4-piperidyl)-2-hydroxyhexanoic acid as an oily product. This product is dissolved in toluene (30 ml), and ethanol (5 ml) and p-toluenesulfonic acid (0.1 g) are added to the solution, followed by stirring at 90° C. for 1.5 hours. Ethyl acetate (150 ml) is added to the mixture, and the resulting mixture is washed with saturated sodium hydrogencarbonate solution (50 ml) and water (50 ml), dried over anhydrous magnesium sulfate and concentrated under reduced pressure to give R-isomer-rich ethyl 6-(1-benzyloxycarbonyl-4-piperidyl)-2-hydroxyhexanoate (0.84 g) as a colorless oil. This product (0.3 g) is dissolved in pyridine (3 ml), and methanesulfonyl chloride (0.15 ml) is added dropwise to the solution with stirring under ice-cooling over the period of 2 minutes. The mixture is stirred for 1 hour under ice-cooling, and ethyl acetate (70 ml) is added to the mixture. The resulting mixture is washed with 1N hydrochloric acid (30 ml ×2), saturated sodium hydrogencarbonate solution (30 ml) and water (30 ml). The ethyl acetate layer is dried over anhydrous magnesium sulfate and concentrated under reduced pressure to give R-isomer-rich ethyl 6-(1-benzyloxycarbonyl-4-piperidyl)-2-methanesulfonyloxyhexanoate [0.35 g: $[\alpha]_D + 16.6°$ (in methanol)] as a colorless oil.

EXPERIMENT EXAMPLE 1

Experiment on Inhibition of Angiotensin I Converting Enzyme (ACE) by the Compounds of This Invention

[Experimental Method]

The experiment was conducted in accordance with a modification of the method described by Cushman et al. (Biochemical Pharmacology, Vol. 20, pp. 1637, 1971). Thus, using hippuryl-L-histidyl-L-leucine (HHL) as the substrate, the ACE inhibitory activity was determined in terms of percent inhibition on the amount of hippuric acid produced by ACE when the compound of the present invention was added. A solution of the compound of the present invention in 0.02 to 5% dimethylsulfoxide-100 mM borate-HCl buffer solution (pH 8.3, containing 300 mM sodium chloride) was added to 100 μl of ACE (protein concentration, 20 mg/ml) and 100 μl of 1.25 mM HHL. In this experiment, a borate-HCl buffer solution containing dimethylsulfoxide at a concentration equal to that of the test solution was used as a control. After warming the solution at 37° C. for 1 hour, 150 μl of 1N hydrochloric acid was added to the solution to terminate the reaction. After 0.8 ml of ethyl acetate was added, the solution was centrifuged at 11,500 rpm for 2 minutes. A 0.5 ml aliquot was separated from the ethyl acetate layer and dried at a temperature of not more than 40° C. under nitrogen gas streams. The residue was mixed thoroughly with 4.5 ml of distilled water, and the mixture was subjected to colorimetry at a wavelength of 228 nm.

[Test Results]

The test results obtained with regard to the compounds of the present invention are as shown in Table 15.

TABLE 15

| Example No. of test compound | Concentration (μM) | ACE inhibitory activity (%) |
| --- | --- | --- |
| 73 | 0.1 | 92 |
| 74 | 0.1 | 94 |
| 75 | 0.1 | 89 |
| 82 | 0.1 | 92 |
| 91 | 0.1 | 92 |
| 95 | 0.1 | 98 |
| 98 | 0.1 | 98 |
| 100 | 0.1 | 98 |

EXPERIMENT EXAMPLE 2

Effect of the Compounds of the Present Invention against Hypertensive Activity of Angiotensin I

[Experimental Method]

Male rats (Sprague-Awley) weighing 300 to 400 g which were fed under free access to drinking water and feed were used as experimental animals. The rats were anesthetized with intraperitoneal administration of pentobarbital sodium (50 mg/kg) on the day before the test day, and a polyethylene tube was inserted into each of the femoral artery for measurement of blood pressure and the femoral vein for injection of angiotensin I and II. And the tubes were fixed.

On the test day, an average blood pressure in the control phase was measured by an electric hemodynamometer (MPU-0.5-290-0-III model, manufactured by NEC-Sanei, Japan) and recorded by a polygraph (NEC-Sanei, Tupe 365, or Nippon Kohden Type RM-45), and thereafter, angiotensin I and then angiotensin II were injected through the femoral vein at a dose of 300 ng/kg and 100 ng/kg, respectively, to measure the hypertensive activity. Then, 300 μg/kg of the compound of the present invention was administered intravenously as an isotonic saline solution, and 5, 10, 30, 60, 90 and 120 minutes after the administration, angiotensin I and II were injected repeatedly to trace hypertensive reactions. In calculating the percent inhibition to the hypertensive activity of angiotensin I, the percent inhibitory value was corrected based on the variation with time in the hypertensive reaction by angiotensin II.

[Test Results]

The test results obtained with regard to the compounds of the present invention are as shown in Table 16.

TABLE 16

| Example No. of tested compound | Dose μg/kg (i.v.) | Inhibition against hypertensive reaction by angiotension I, % Length of time elapsed after the administration | | | | | |
|---|---|---|---|---|---|---|---|
| | | 5 min. | 10 min. | 30 min. | 60 min. | 90 min. | 120 min. |
| 90 | 300 | 100 | 100 | 100 | 90 | 67 | 62 |
| 95 | 300 | 96 | 94 | 99 | 89 | 96 | 91 |
| 98 | 300 | 100 | 100 | 100 | 100 | 95 | 79 |

PREPARATION EXAMPLE

The compounds (I) of the present invention can be used, for example, for the treatment of hypertension in the following formulation examples.

| 1. Tablets. | |
|---|---|
| (1) 3(R)—[1(S)—Carboxy-3-(4-piperidyl)propyl]-amino-4-oxo-2,3,4,5-tetrahydro-1,5-benzo-thiazepine-5-acetic acid | 10 g |
| (2) Lactose | 90 g |
| (3) Corn starch | 29 g |
| (4) Mangesium stearate | 1 g |
| | 130 g |

The ingredients (1) and (2) and 17 g of (3) are blended, and granulated together with a paste prepared from 7 g of the ingredient (3). Five g of the ingredient (3) and the ingredient (4) are added to the resulting granules, and the mixture is compressed by atabletting machine to prepare 1000 tablets of a diameter of 7 mm each containing 10 mg of the ingredient (1).

| 2. Injectable solution. | |
|---|---|
| (1) 3(R)—[1(S)—Carboxy-3-(4-piperidyl)propyl]-amino-4-oxo-2,3,4,5-tetrahydro-1,5-benzo-thiazepine-5-acetic acid | 10 g |
| (2) Sodium chloride | 9 g |

The ingredients (1) and (2) are dissolved in 1000 ml of distilled water, and cahrged into 1000 brown ampoules each containing 1 ml of the solution. The air in the ampoules is replaced with nitrogen gas, and the ampoules are sealed. The entire preparation steps are conducted under strile conditions.

What is claimed is:

1. A compound of the formula:

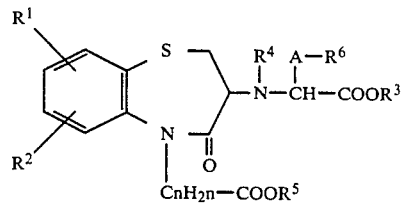

wherein $R^1$ and $R^2$ are independently hydrogen, halogen, trifluoromethyl, $C_{1-4}$ alkyl or $C_{1-4}$ alkoxy, or both jointly form tri- or tetramethylene, $R^3$ and $R^5$ are independently hydrogen, $C_{1-4}$ alkyl or phenyl-$C_{1-4}$ alkyl, $R^4$ is hydrogen or $C_{1-4}$ alkyl, $R^6$ is oxetanyl, thietanyl, azetidinyl, tetrahydrofuryl, tetrahydrothienyl, pyrrolidinyl, oxanyl, thianyl, piperidyl, oxepanyl, thiepanyl, perhydroazeipinyl, oxocanyl, thiocanyl, perhydroazocinyl, dioxanyl, dithianyl, piperazinyl, morpholinyl, perhydrothiazinyl, oxathianyl, perhydrodiazepinyl, oxathiepanyl, dioxepanyl, dithiepanyl, perhydrooxazepinyl, perhydrothiazepinyl, perhydrooxazocinyl, perhydrothiazocinyl, oxathiocanyl, perhydrodiazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydrobenzothienyl, 1,3-dihydrobenzothienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-bemzoxepinyl, 2,3,4,5-tetrahydro-1-benzothiapinyl, 1,3,4,5-tetrahydro-2-benzothiepinyl, 1,2,4,5-tetrahydro-3-benzothiepinyl, 2,3-dihydro-1,4-benzodioxinyl 2,3-dihydro-1,4-dithianaphthyl, 1,2,3,4-tetrahydroquinoxalinyl, 3,4-dihydro-2H-1,4 benzoxadinyl, 3,4-dihydro-2H-1,4-benzothiadinyl, 2,3-dihydro-1,4-benzoxathienyl, 3,4-dihydro-2H-1,5-benzoxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydroisoquinolyl, perhydro-1-thianaphthyl or perhydro-2-thianaphthyl, each of said groups being unsubstituted or substituted by $C_{1-4}$ alkyl, oxo, $C_{1-5}$ alkanoyl, benzoyl, phenyl-$C_{1-4}$ alkoxycarbonyl or $C_{1-4}$ alkoxycarbonyl, A is $C_{1-16}$ alkylene and the group $CnH_{2n}$ represents methylene, ethylene or ethylidene, or a pharmaceutically acceptable salt thereof.

2. A compound according to claim 1, wherein $R^6$ is oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiazinyl, oxathianyl, perhydrodiazepinyl, oxathiepanyl, dioxepanyl, dithiepanyl, perhydrooxazepinyl, perhydrothiazepinyl, perhydrooxazocinyl, perhydrothiazocinyl, oxathiocanyl, perhydrodiazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydrobenzothienyl, 1,3-dihydrobenzothienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiadinyl, 2,3-dihydro-1,4-benzoxathienyl, 3,4-dihydro-2H-1,5-benzoxepanyl, 2,3-dihydro-5H-1,4-benzodioxepinyl, 2,3,4,5-tetrahydro-1H-1,5-benzodiazepinyl, 2,3,4,5-tetrahydro-1H-1,4benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydroisoquinolyl, perhydro-1-thianaphthyl or perhydro-2-thianaphthyl, each of said groups being unsubstituted or substituted by one member selected from the group consisting of $C_{1-4}$ alkyl, oxo, $C_{1-5}$ alkanoyl, benzoyl, phenyl-$C_{1-4}$ alkoxycarbonyl and $C_{1-4}$ alkoxycarbonyl.

3. A compound according to claim 1, wherein $R^6$ is oxanyl, thianyl or piperidyl, each of said groups being unsubstituted or substituted by $C_{1-4}$ alkyl, oxo, $C_{1-5}$ alkanoyl, benzoyl, phenyl-$C_{1-4}$ alkoxycarbonyl or $C_{1-4}$ alkoxycarbonyl.

4. A compound according to claim 1, wherein $R^6$ is piperidyl being unsubstituted or substituted by $C_{1-4}$ alkyl, oxo, $C_{1-5}$ alkanoyl, benzoyl, phenyl-$C_{1-4}$ alkoxycarbonyl or $C_{1-4}$ alkoxycarbonyl.

5. A compound according to claim 1, wherein $R^1$ and $R^2$ are hydrogen.

6. A compound according to claim 1, wherein $R^3$ and $R^5$ are independently hydrogen or $C_{1-4}$ alkyl.

7. A compound according to claim 1, wherein $R^3$ and $R^5$ are hydrogen.

8. A compound according to claim 1, wherein $R^4$ is hydrogen.

9. A compound according to claim 4, wherein the piperidyl group is 4-piperidyl.

10. A compound according to claim 1, wherein $R^6$ is 4-piperidyl.

11. A compound according to claim 1, wherein the group $CnH_{2n}$ is methylene.

12. A compound according to claim 1, wherein A is $C_{2-9}$ alkylene.

13. A compound according to claim 1, wherein A is tetramethylene.

14. A compound according to claim 1, wherein $R^6$ is 1,3-dioxoisoindolinyl.

15. A compound of the formula

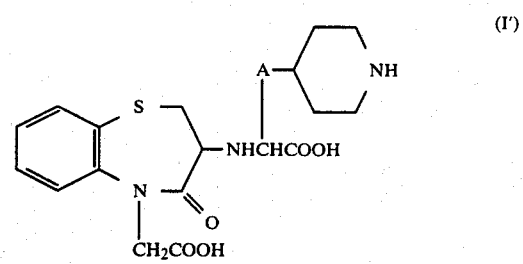

wherein A is $C_{2-9}$ alkylene, or a pharmaceutically acceptable salt thereof.

16. A compound according to claim 15, wherein A is $C_{2-6}$ alkylene.

17. A compound according to claim 15, wherein A is tetramethylene.

18. The compound according to claim 1, which is 3(R)-[1(S)-ethoxycarbonyl-7-phthalimidoheptyl]amino-4-oxo-2,3,4,5-tetrahydro-1,5-benzothiazepine-5-acetic acid.

19. The compound according to claim 1, which is 3(R)-[1(S)-ethoxycarbonyl-3-(3,4,5,6-tetrahydro-2H-pyran-4-yl)propyl]amino-4-oxo-2,3,4,5-tetrahydro-1,5-benzothiazepine5-acetic acid.

20. The compound according to claim 1, which is 3(R)-[1(S)-ethoxycarbonyl-3-(thian-4-yl)propyl]amino-4-oxo-2,3,4,5-tetrahydro-1,5-benzothiazepine-5-acetic acid.

21. The compound according to claim 1, which is 3(R)-[1(S)-carboxy-3-(4-piperidyl)propyl]amino-4-oxo-2,3,4,5-tetrahydro-1,5-benzothiazepine-5-acetic acid.

22. The compound according to claim 1, which is 3(R)[1(S)-carboxy-5-(4-piperidyl)pentyl]amino-4-oxo-2,3,4,5-tetrahydro-1,5-benzothiazepine-5-acetic acid.

23. The compound according to claim 1, which is 3(R)[1(S)-carboxy-6-(4-piperidyl)hexyl]amino-4-oxo-2,3,4,5-tetrahydro-1,5-benzothiazepine-5-acetic acid.

24. The compound according to claim 1, which is 3(R)[1(S)-carboxy-4-(4-piperidyl)butyl]amino-4-oxo-2,3,4,5-tetrahydro-1,5-benzothiazepine-5-acetic acid.

25. The compound according to claim 1, which is 3(R)[1(S)-ethoxycarbonyl-4-(4-piperadyl)butyl]amino-4-oxo2,3,4,5-tetrahydro-1,5-benzothiazepine-5-acetic acid.

26. A pharmaceutical composition suitable for prevention or treatment of hypertension which comprises, as an active ingredient, an effective antihypertensive amount of a compound of the formula:

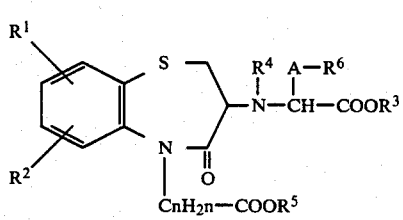

wherein

R$^1$ and R$^2$ are independently hydrogen, halogen, trifluoromethyl, C$_{1-4}$ alkyl or C$_{1-4}$ alkoxy, or both jointly form tri- or tetramethylene, R$^3$ and R$^5$ are independently hydrogen, C$_{1-4}$ alkyl or phenyl-C$_{1-4}$ alkyl, R$^4$ is hydrogen or C$_{1-4}$ alkyl, R$^6$ is oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiazinyl, oxathianyl, perhydrodiazepinyl, oxathiepanyl, dioxepanyl, dithiepanyl, perhydrooxazepinyl, perhydrothiazepinyl, perhydrooxazocinyl, perhydrothiazocinyl, oxathiocanyl, perhydrodiazocinyl, dithiocanyl, dioxocanyl, chromanyl, isochromanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisobenzofuryl, 2,3-dihydrobenzothienyl, 1,3-dihydrobenzothienyl, indolinyl, isoindolinyl, 2,3,4,5-tetrahydro-1(1H)-benzoazepinyl, 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2-benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiadinyl, 2,3-dihydro-1,4-benzoxathienyl, 3,4-dihydro-2H-1,5-benzoxepanyl, 2,3-dihydro-5H-1,4-benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro-5H-1,4-benzodithiepinyl, perhydroindolyl, perhydroisoindolyl, perhydroquinolyl, perhydroisoquinolyl, perhydro-1-thianaphthyl or perhydro-2-thianaphthyl, each of said groups being unsubstituted or substituted by C$_{1-4}$ alkoxycarbonyl or C$_{1-4}$ alkoxycarbonyl, A is C$_{1-16}$ alkylene and the group CnH$_{2n}$ represents methylene, ethylene or ethylidene, or a pharmaceutically acceptable salt thereof, and a pharmaceutically acceptable carrier, excipient or diluent therefor.

27. A method for prevention or treatment of hypertension in a mammal, which comprises administering to said mammal an effective antihypertensive amount of a compound of the formula:

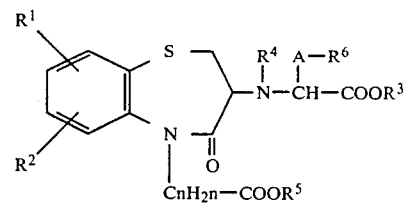

wherein

R$^1$ and R$^2$ are independently hydrogen, halogen, trifluoromethyl, C$_{1-4}$ alkyl or C$_{1-4}$ alkoxy, or both jointly from tri- or tetramethylene, R$^3$ and R$^5$ are independently hydrogen, C$_{1-4}$ alkyl or phenyl-C$_{1-4}$ alkyl, R$^4$ is hydrogen or C$_{1-4}$ alkyl, R$^6$ is oxetanyl, thietanyl, azetidinyl, tetrahydrofuryl, tetrahydrothienyl, pyrrolidinyl, oxanyl, thianyl, piperidyl, oxepanyl, thiepanyl, perhydroazepinyl, oxocanyl, thiocanyl, perhydroazocinyl, dioxanyl, dithianyl, piperazinyl, morpholinyl, perhydrothiazinyl, oxathianyl, perhydrodiazepinyl, oxathiepanyl, dioxepanyl, dithiepanyl, perhydrooxazepinyl, perhydrothiazepinyl, perhydrooxazocinyl, perhydrothiazocinyl, oxathiocanyl, perhydrodiazocinyl, dithiocanyl, dioxocanyl, chromanyl, isochormanyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, 2,3-dihydrobenzofuryl, 1,3-dihydroisopenzofuryl, 2,3-dihydrobenzothienyl, 1,3-dihydrobenzothienyl, indolinyl, isoindolinyl, 2,3,4,5-tetrahydro-1(1H)-benzoazepinyl 2,3,4,5-tetrahydro-3(1H)-benzoazepinyl, 2,3,4,5-tetrahydro-2(1H)-benzoazepinyl, 2,3,4,5-tetrahydro-1-benzoxepinyl, 1,3,4,5-tetrahydro-2benzoxepinyl, 1,2,4,5-tetrahydro-3-benzoxepinyl, 2,3,4,5-tetrahydro-1-benzothiepinyl, 1,3,4,5-tetrahydro-2-benzothiepinyl, 1,2,4,5-tetrahydro-3-benzothiepinyl, 2,3-dihydro-1,4-benzodioxinyl, 2,3-dihydro-1,4-dithianaphthyl, 1,2,3,4-tetrahydroquinoxalinyl, 3,4-dihydro-2H-1,4-benzoxadinyl, 3,4-dihydro-2H-1,4-benzothiadinyl, 2,3-dihydro-1,4-benzoxathienyl, 3,4-dihydro-2H-1,5-benzoxepanyl, 2,3-dihydro-5H-1,4benzodioxepinyl, 2,3,4,5-tetrahydro-1H-1,5-benzodiazepinyl, 2,3,4,5-tetrahydro-1H-1,4-benzodiazepinyl, 3,4-dihydro-2H-1,5-benzodithiepinyl, 2,3-dihydro 5H-1,4-benzodithiepinyl, perhydroindolyl, perhydroisoindolyl, perhydroquinolyl, perhydroisoquinolyl, perhydro-1-thianaphthyl or perhydro-2-thianaphthyl, each of said groups being unsubstituted or substituted by C$_{1-4}$ alkyl, oxo, C$_{1-5}$ alkanoyl, benzoyl, phenyl-C$_{1-4}$ alkoxycarbonyl or C$_{1-4}$ alkoxycarbonyl, A is C$_{1-16}$ alkylene and the group CnH$_{2n}$ represents methylene, ethylene or ethylidene, or a pharmaceutically acceptable salt thereof.

* * * * *